United States Patent
Jakobi et al.

(10) Patent No.: US 11,477,982 B2
(45) Date of Patent: Oct. 25, 2022

(54) 2-AMINO-5-OXYALKYL-PYRIMIDINE DERIVATIVES AND THEIR USE FOR CONTROLLING UNDESIRED PLANT GROWTH

(71) Applicants: Bayer CropScience Aktiengesellschaft, Monheim am Rhein (DE); Bayer Aktiengesellschaft, Leverkusen (DE)

(72) Inventors: Harald Jakobi, Frankfurt (DE); Estella Buscato Arsequell, Frankfurt am Main (DE); Klemens Minn, Hattersheim (DE); Uwe Doeller, Rodgau (DE); Hansjoerg Dietrich, Liederbach am Taunus (DE); Elmar Gatzweiler, Bad Nauheim (DE); Anu Bheemaiah Machettira, Frankfurt am Main (DE); Christopher Hugh Rosinger, Hofheim (DE); Dirk Schmutzler, Hattersheim (DE)

(73) Assignees: BAYER CROPSCIENCE AKTIENGESELLSCHAFT, Monheim am Rhein (DE); BAYER AKTIENGESELLSCHAFT, Leverkusen (DE)

( * ) Notice: Subject to any disclaimer, the term of this patent is extended or adjusted under 35 U.S.C. 154(b) by 267 days.

(21) Appl. No.: 16/494,485

(22) PCT Filed: Mar. 29, 2018

(86) PCT No.: PCT/EP2018/058081
§ 371 (c)(1),
(2) Date: Sep. 16, 2019

(87) PCT Pub. No.: WO2018/184978
PCT Pub. Date: Oct. 11, 2018

(65) Prior Publication Data
US 2020/0029565 A1    Jan. 30, 2020

(30) Foreign Application Priority Data
Apr. 5, 2017 (EP) .................................... 17164918

(51) Int. Cl.
*A01N 43/54* (2006.01)
*C07D 239/42* (2006.01)
*C07D 405/12* (2006.01)

(52) U.S. Cl.
CPC ........... *A01N 43/54* (2013.01); *C07D 239/42* (2013.01); *C07D 405/12* (2013.01)

(58) Field of Classification Search
CPC ..... A01N 43/54; C07D 239/42; C07D 405/12
See application file for complete search history.

(56) References Cited

U.S. PATENT DOCUMENTS

| | | | | |
|---|---|---|---|---|
| 6,069,114 A | * | 5/2000 | Lorenz | ................... A01N 43/68 504/232 |
| 8,329,717 B2 | | 12/2012 | Minn et al. | |
| 8,445,408 B2 | * | 5/2013 | Minn | ................... C07D 405/12 504/239 |
| 9,375,002 B2 | * | 6/2016 | Minn | ................... C07D 405/12 |
| 10,183,914 B2 | * | 1/2019 | Minn | ................... C07D 239/84 |
| 10,251,395 B2 | | 4/2019 | Jakobi et al. | |
| 10,806,142 B2 | * | 10/2020 | Minn | .................... A01N 43/54 |
| 2010/0167934 A1 | * | 7/2010 | Minn | .................... A01N 43/54 504/239 |
| 2010/0167935 A1 | * | 7/2010 | Minn | ................... C07D 239/50 504/239 |
| 2015/0094205 A1 | * | 4/2015 | Minn | ................... C07D 239/47 544/316 |
| 2017/0158644 A1 | * | 6/2017 | Minn | ................... C07D 239/42 |
| 2019/0082692 A1 | * | 3/2019 | Minn | ................... C07D 405/12 |
| 2019/0230927 A1 | * | 8/2019 | Jakobi | ................. C07D 249/14 |

FOREIGN PATENT DOCUMENTS

| | | |
|---|---|---|
| EP | 0523533 A1 | 1/1993 |
| WO | 2010/076009 A1 | 7/2010 |
| WO | 2010/076010 A1 | 7/2010 |
| WO | 2013/144187 A1 | 10/2013 |

(Continued)

OTHER PUBLICATIONS

PCT International Search Report for PCT/EP2018/058081, dated Jun. 19, 2018.

(Continued)

*Primary Examiner* — Alexander R Pagano
(74) *Attorney, Agent, or Firm* — McBee Moore & Vanik IP, LLC

(57) ABSTRACT

What are described are compounds of the general formula (I) and agrochemically acceptable salts thereof

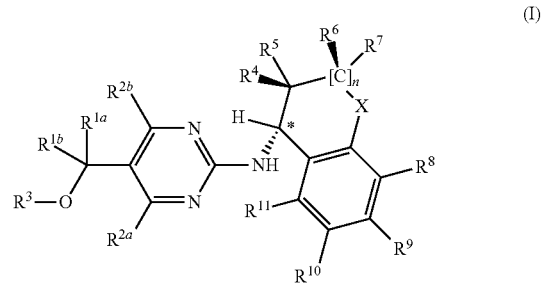

and their preparation and their use in the crop protection sector.

29 Claims, No Drawings

(56) References Cited

FOREIGN PATENT DOCUMENTS

| WO | 2016/001118 A1 | | 1/2016 | | |
|---|---|---|---|---|---|
| WO | 2017/016914 A1 | | 2/2017 | | |
| WO | WO-2017016914 A1 | * | 2/2017 | ........... | C07D 405/12 |
| WO | 2017/108656 A1 | | 6/2017 | | |
| WO | WO-2017220467 A1 | * | 12/2017 | ........... | A01N 43/707 |

OTHER PUBLICATIONS

Ciapetti et al., "Molecular Variations Based on Isosteric Replacements," The Practice of Medicinal Chemistry, 3rd edition, chapter 15, pp. 290-342 (2008).

* cited by examiner

2-AMINO-5-OXYALKYL-PYRIMIDINE DERIVATIVES AND THEIR USE FOR CONTROLLING UNDESIRED PLANT GROWTH

CROSS-REFERENCE TO RELATED APPLICATIONS

This application is the National Stage entry of International Application No. PCT/EP2018/058081, filed 29 Mar. 2018, which claims priority to European Patent Application No. 17164918.9, filed 5 Apr. 2017.

BACKGROUND

Field

The invention relates to the technical field of crop protection compositions, particularly to that of herbicides for selective control of broad-leaved weeds and weed grasses in crops of useful plants and in the ornamental garden sector and for general control of broad-leaved weeds and weed grasses in areas of the environment where plant growth is disruptive.

More particularly, the invention relates to substituted 2-amino-5-oxyalkylpyrimidine derivatives, to processes for their preparation and to their use for control of harmful plants.

The compounds of the formula (I) according to the invention have, in the 5 position of the pyrimidine, an oxyalkyl group and, in the 2-position of the pyrimidine, a partially hydrogenated bicyclic substituent attached via an amine to the aromatic system in the alpha position, where the pyrimidine may also be substituted in the 4 position and 6 position and the oxyalkyl group via the alkyl radical together with the substituent in the adjacent position may form a ring.

Description of Related Art

The herbicidal action of diaminopyrimidines and also of monoaminopyrimidines is already known from the prior art.

2,4-Diaminopyrimidines and their use in the field of crop protection are disclosed, for example, by the documents EP 0523533 A1, WO 2010/076009 A1 and WO 2010/076010 A1. 2,4-Diaminopyrimidines with a bicyclic radical which have (1R,2S) configuration on the bridged and adjacent carbon atoms and at the same time feature herbicidal efficacy are known from US 2010/0167934 A1.

Further diaminopyrimidines, namely substituted furano-/thienocycloalkylamino-2-pyrimidine derivatives, are disclosed in the document WO 2017/016914 A1. The pyrimidine ring of these furano-/thienocycloalkylamino-2-pyrimidine derivatives may, in addition to the amino substituent in the 2-position, have additional amino radicals in the 4-, 5- or in the 6-position. With the compounds covered by claim 1, the subject matter of the present application differs from the compounds known from WO 2017/016914 A1 by a condensed phenyl ring. Instead, the compounds known from WO 2017/016914 A1 have a condensed thiophene ring. The improvement in herbicidal activity effected by this difference is summarized by the comparative data in Tables 4a and 4b.

Monoaminopyrimidine derivatives having herbicidal action, namely 5-aminopyrimidine derivatives, are disclosed, for example, in document WO 2013/144187 A1. Other monoaminopyrimidine derivatives having herbicidal action, namely 2-amino-5-ketopyrimidine derivatives, are disclosed in document WO 2016/001118 A1. The improvement in herbicidal activity effected by the compounds according to the invention is demonstrated by the comparative data summarized in Tables 3a and 3b.

Further 2-aminopyrimidine derivatives, namely 2-amino-5-ketoximepyrimidine derivatives, are subject matter of the not yet laid-open application with the application number PCT/EP2016/081655. After its disclosure, this application will be a document according to Art. 54 (3) EPC with regard to the present application.

However, the use of the known pyrimidine derivatives as selective herbicides for control of harmful plants or as plant growth regulators in various crops of useful plants frequently entails an application rate that incurs high costs or results in unwanted damage to the useful plants. Moreover, in many cases, the use of the active compounds is uneconomic owing to comparatively high production costs.

It is therefore desirable to provide alternative chemical active ingredients based on pyrimidine derivatives which can be used as herbicides or plant growth regulators and which are associated with certain advantages compared to systems known from the prior art.

SUMMARY

It is an object of the present invention to provide alternative pyrimidine derivatives which can be used as herbicides or plant growth regulators, having satisfactory herbicidal action and a broad spectrum of activity against harmful plants and/or having high selectivity in crops of useful plants.

Moreover, compared to the pyrimidine derivatives known from the prior art, the alternative pyrimidine derivatives display a better profile of properties, particularly better herbicidal activity against harmful plants, a broader spectrum of harmful plants and/or higher selectivity in crops of useful plants.

The object is achieved by means of specifically substituted 2-amino-5-oxyalkylpyrimidine derivatives of the formula (I) as claimed in claim 1, which, in particular owing to the substitution in the 5-position of the pyrimidine ring, can advantageously be used as herbicides and also as plant growth regulators. The substitution in the 5-position of the pyrimidine ring relates to the group which comprises the radicals $R^3$—O—C, $R^{1a}$ and $R^{1b}$.

Accordingly, the present invention provides compounds of the formula (I)

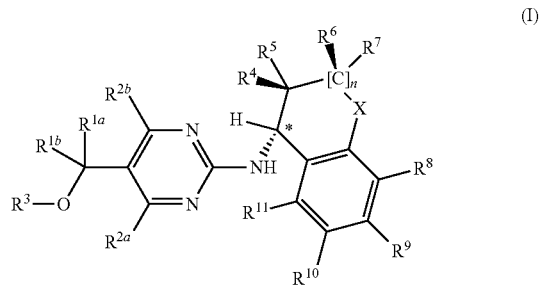

and the agrochemically acceptable salts thereof in which $R^{1a}$ is selected from the group consisting of
hydrogen, cyano, C(O)OH, C(O)NH$_2$;
($C_1$-$C_6$)-alkyl, ($C_1$-$C_6$)-haloalkyl, ($C_1$-$C_6$)-alkylcarbonyl-($C_1$-$C_4$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl, ($C_2$-$C_6$)-alkenyl, ($C_2$-$C_6$)-haloalkenyl;

($C_2$-$C_6$)-alkynyl, ($C_2$-$C_6$)-haloalkynyl;

($C_6$-$C_{14}$)-aryl which may in each case be substituted in the aryl moiety by halogen, ($C_1$-$C_6$)-alkyl and/or ($C_1$-$C_6$)-haloalkyl;

pyridyl which may in each case be substituted by halogen, ($C_1$-$C_6$)-alkyl and/or ($C_1$-$C_6$)-haloalkyl;

thienyl which may in each case be substituted by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;

hydroxy-($C_1$-$C_6$)-alkyl, amino-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-allyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl;

$R^{1b}$ is selected from the group consisting of cyano, C(O)OH, C(O)NH$_2$;

($C_1$-$C_6$)-alkyl, ($C_1$-$C_6$)-haloalkyl, ($C_1$-$C_6$)-alkylcarbonyl-($C_1$-$C_4$)-alkyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl;

($C_2$-$C_6$)-alkynyl, ($C_2$-$C_6$)-haloalkynyl;

($C_6$-$C_{14}$)-aryl which may be substituted in the aryl moiety in each case by halogen, ($C_1$-$C_6$)-alkyl and/or ($C_1$-$C_6$)-haloalkyl;

pyridyl which may in each case be substituted by halogen, ($C_1$-$C_6$)-alkyl and/or ($C_1$-$C_6$)-haloalkyl;

thienyl which may in each case be substituted by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;

hydroxy-($C_1$-$C_6$)-alkyl, amino-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl;

where, if $R^{1a}$ does not represent hydrogen, $R^{1a}$ is attached to $R^{1b}$ via a bond so that, together with the carbon to which these two radicals are attached, a saturated or unsaturated 3- to 7-membered carbo- or heterocycle is formed which is unsubstituted or is substituted with one or more substituents selected from the group consisting of ($C_1$-$C_6$)-alkyl, ($C_1$-$C_6$)-haloalkyl, ($C_3$-$C_8$)-cycloalkyl, spiro-($C_3$-$C_6$)-cycloalkyl;

$R^{2a}$ and $R^{2b}$ are in each case independently of one another selected from the group consisting of hydrogen, halogen, hydroxyl, cyano, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_1$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

aminocarbonyl-($C_1$-$C_6$)-alkyl, di-($C_1$-$C_6$)-alkylaminocarbonyl-($C_1$-$C_6$)-alkyl;

N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which is unsubstituted or mono- or polysubstituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_3$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_6$)-cycloalkenylthio and ($C_3$-$C_6$)-alkynylthio;

$R^3$ is selected from the group consisting of hydrogen;

($C_1$-$C_6$)-alkylcarbonyl, ($C_1$-$C_6$)-haloalkylcarbonyl;

($C_2$-$C_6$)-alkenylcarbonyl, ($C_2$-$C_6$)-haloalkenylcarbonyl;

($C_2$-$C_6$)-alkynylcarbonyl, ($C_2$-$C_6$)-haloalkynylcarbonyl;

($C_6$-$C_{14}$)-arylcarbonyl which may in each case be substituted in the aryl moiety by halogen, ($C_1$-$C_6$)-alkyl and/or ($C_1$-$C_6$)-haloalkyl;

aminocarbonyl, [($C_1$-$C_6$)-alkylamino]carbonyl, [di-($C_1$-$C_6$)-alkylamino]carbonyl;

($C_1$-$C_6$)-alkoxycarbonyl, ($C_2$-$C_6$)-alkenyloxycarbonyl, ($C_2$-$C_6$)-alkynyloxycarbonyl;

($C_1$-$C_6$)-trialkylsilyl;

($C_1$-$C_6$)-alkylsulfonyl, ($C_1$-$C_6$)-haloalkylsulfonyl;

($C_6$-$C_{14}$)-arylsulfonyl which may in each case be substituted in the aryl moiety by halogen, ($C_1$-$C_6$)-alkyl and/or ($C_1$-$C_6$)-haloalkyl;

($C_1$-$C_6$)-alkyl, ($C_1$-$C_6$)-haloalkyl, ($C_1$-$C_6$)-alkylcarbonyl-($C_1$-$C_4$)-alkyl;

($C_2$-$C_6$)-alkenyl, ($C_2$-$C_6$)-haloalkenyl;

($C_2$-$C_6$)-alkynyl, ($C_2$-$C_6$)-haloalkynyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_6$-$C_{14}$)-aryl which may be substituted in the aryl moiety in each case by halogen, ($C_1$-$C_6$)-alkyl and/or ($C_1$-$C_6$)-haloalkyl;

($C_2$-$C_{14}$)-Het-aryl which may in each case be substituted in the Het-aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be mono- or polysubstituted in the cycloalkyl radical by ($C_1$-$C_6$)-alkyl and/or halogen;

($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl-($C_1$-$C_6$)-alkyl, ($C_3$-$C_8$)-cycloalkenyl-($C_1$-$C_6$)-haloalkyl, hydroxy-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl;

$R^4$ and $R^5$ are each independently of one another selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or the radicals $R^4$ and $R^5$ together with the carbon atom to which they are attached form a three- to seven-membered ring;

$R^6$ and $R^7$ are each independently of one another selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the radicals $R^6$ and $R^7$ together form a ($C_1$-$C_7$)-alkylene group which may contain one or more oxygen and/or sulfur atoms, where the ($C_1$-$C_7$)-alkylene group may be mono- or polysubstituted by halogen and the respective halogen substituents may be identical or different;

n represents the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-dialkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)- alkynyloxycarbonyl, $(C_2-C_6)$-haloalkynyloxycarbonyl, $(C_6-C_{14})$-aryl and nitro, where the radicals $R^9$ and $R^{10}$ may be linked via an —O—CH$_2$—O— group to form a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl.

DETAILED DESCRIPTION OF A PREFERRED EMBODIMENT

The 2-amino-5-oxyalkylpyrimidine derivatives of the formula (I) according to the invention differ from the diaminopyrimidine derivatives known from the prior art (e.g. the herbicides having a 2,4-diaminopyrimidine structure known from the documents EP 0523533 A1, WO 2010/076009 A1 and WO 2010/076010 A1) in the number of the amino groups directly attached to a ring atom of the pyrimidine ring. The comparative data of Tables 1 and 2 below relate to the diaminopyrimidine derivatives known from WO 2010/076010 A1.

Thus, in the monoaminopyrimidines of the formula (I) according to the invention, the two radicals $R^{2a}$ and $R^{2b}$ do not represent an amino group, i.e. $R^{2a}$ and $R^{2b}$ are not attached to the pyrimidine ring via a nitrogen atom. The 2-amino-5-oxyalkylpyrimidines according to the invention are substituted by only one amino group, and this amino group connects the pyrimidine ring and the bicyclic substituent to one another.

By contrast, the inventive 2-amino-5-oxyalkylpyrimidines of the formula (I) of the present invention differ from the already known pyrimidines having only one amino substituent (monoaminopyrimidines) (e.g. from document WO 2013/144187 A1) in that the amino group is arranged in the 2 position, i.e. between the two nitrogen atoms that form part of the pyrimidine ring, and not in the 5 position.

The amino group in the 2 position of the pyridine, in the inventive monoaminopyrimidines of the formula (I), has a partly hydrogenated bicyclic substituent, said partly hydrogenated bicyclic substituent being bonded to the amine in the alpha position to the aromatic system.

The abovementioned 2-amino-5-ketopyrimidine derivatives disclosed in document WO 2016/001118 A1, and the 2-amino-5-ketoximepyrimidine derivatives which are subject matter of the not yet laid-open application mentioned above having the application number PCT/EP2016/081655 have the same number and position of the amino group at the pyrimidine ring as the monoaminopyrimidines of the formula (I) according to the invention.

However, the monoaminopyrimidines of the formula (I) according to the invention differ from the two 2-aminopyrimine derivatives mentioned above in that they have no keto group (carbonyl group) or no ketooxime structural element in position 5. That is to say that the group of structural elements in the 5 position of the compounds according to the invention which comprises the radicals $R^3$—O—C, $R^{1a}$ and $R^{1b}$ and together form an oxyalkyl group are distinguished in that they have no carbonyl and no ketooxime structural element. The comparative data of Tables 3 and 4 below relate to the monoaminopyrimidine derivatives known from WO 2016/001118 A1.

The surprisingly good herbicidal activity of the compounds according to the invention in comparison to the analogous diaminopyrimidines from WO 2010/076010 A1 and in comparison to the monoaminopyrimidines known from WO 2016/001118 A1 is confirmed by the comparative pairs compared in the 4 tables below.

TABLE 1

Comparison of the pre-emergence herbicidal activity of compounds according to the invention with compounds from WO 2010/076010 A1

| Example No. or Application No. | Dosage [g/ha] | Herbicidal action against [%] | | | | | | |
|---|---|---|---|---|---|---|---|---|
| | | ALOMY | AVEFA | CYPES | ECHCG | LOLRI | SETVI | ABUTH |
| 1.4 | 320 | 100 | 100 | 100 | | | | 100 |
| | 80 | 90 | 80 | 80 | 100 | 100 | 100 | 100 |
| WO 2010/076010 A1 | 320 | 60 | 10 | 70 | | | | 60 |
| | 80 | 30 | 10 | 60 | 30 | 40 | 30 | 20 |

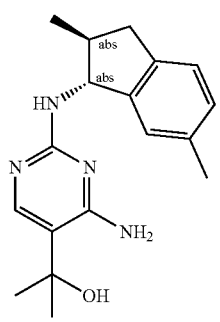

TABLE 1-continued

| Example No. or Application No. | Dosage [g/ha] | | | | | | |
|---|---|---|---|---|---|---|---|
| 1.6 | 320 | 100 | 100 | | | | 100 |
|  | 80 | 100 | 80 | 100 | 100 | 100 | 90 |
| WO 2010/076010 A1 (structure: 2-methyl-indanyl-NH-pyrimidine-NH2 with C(CH3)2OH) | 320 | 60 | 10 | | | | 60 |
|  | 80 | 30 | 10 | 30 | 40 | 30 | 20 |
| 1.7 | 320 |  | 90 |  |  |  |  |
|  | 80 |  | 70 |  |  |  |  |
| WO 2010/076010 A1 (structure: 2-methyl-indanyl-NH-pyrimidine-NH2 with CH(CH3)OH, &1) | 320 |  | 60 |  |  |  |  |
|  | 80 |  | 20 |  |  |  |  |

Comparison of the pre-emergence herbicidal activity of compounds according to the invention with compounds from WO 2010/076010 A1

| Example No. or Application No. | Dosage [g/ha] | Herbicidal action against [%] | | | | | |
|---|---|---|---|---|---|---|---|
|  |  | AMARE | PHBPU | POLCO | STEME | VIOTR | HORMU |
| 1.4 | 320 |  | 100 |  |  |  |  |
|  |  | 100 | 80 | 100 |  |  | 90 |
| WO 2010/076010 A1 |  |  | 0 |  |  |  |  |
|  |  | 40 | 0 | 0 |  |  | 20 |

TABLE 1-continued

| Example No. or Application No. | Dosage [g/ha] | | | | | |
|---|---|---|---|---|---|---|
| 1.6 | 320 | | 100 | | | |
|  | 80 | 100 | 80 | 100 | | 100 |
| WO 2010/076010 A1 *(structure: 2-((1S,2S)-2-methyl-6-methyl-indan-1-ylamino)-5-(2-hydroxypropan-2-yl)pyrimidin-4-amine)* | | | 0 | | | |
|  |  | 40 | 0 | 0 | | 20 |
| 1.7 | 320 | | 80 | | | 100 |
|  | 80 | | | | | |
| WO 2010/076010 A1 *(structure: 2-((1S,2S)-2-methyl-6-methyl-indan-1-ylamino)-5-(1-hydroxyethyl)pyrimidin-4-amine)* | 320 | | | | | |
|  | 80 | | 20 | | | 20 |

TABLE 2

Comparison of the post-emergence herbicidal activity of compounds according to the invention with compounds from WO 2010/076010 A1

| Example No. or Application No. | Dosage [g/ha] | Herbicidal action against [%] | | | | | | |
|---|---|---|---|---|---|---|---|---|
| | | ALOMY | AVEFA | ECHCG | LOLRI | SETVI | ABUTH | AMARE |
| 1.4 | 320 | 70 | 50 | 90 | 90 | 80 | | 100 |
|  | 80 | 20 | 20 | 30 | 60 | | 60 | |
| *(WO 2010/076010 A1 comparison structure)* | 320 | 10 | 0 | 10 | 0 | 30 | | 70 |
|  | 80 | 0 | 0 | 0 | 0 | | 30 | |

TABLE 2-continued

| Ex. | Dose | | | | | | | |
|---|---|---|---|---|---|---|---|---|
| 1.6 | 320 | 100 | 100 | 100 | 100 | 100 | | 100 |
|  | 80 | 90 | | 100 | 40 | 90 | 80 | 100 |
| (structure A) | 320 | 10 | 0 | 10 | 0 | 30 | | 70 |
|  | 80 | 0 | | 0 | 0 | 0 | 30 | 60 |
| 1.7 | 320 | 100 | | | 100 | | 80 | |
|  | 80 | 80 | | 20 | 100 | 100 | 60 | |
|  | 320 | 70 | | | 70 | | 60 | |
|  | 80 | 0 | | 0 | 30 | 60 | 10 | |
| 1.2 | 320 | | 80 | | | | 80 | |
|  | 80 | | 60 | 40 | | 90 | | 100 |
|  | 320 | | 50 | | | | 60 | |
|  | 80 | | 0 | 0 | | 60 | | 80 |

Structure A (shown with Example 1.6):
Indane with two methyl groups (abs, abs stereochemistry) linked via HN to 2-aminopyrimidine bearing 4-NH₂ and 5-C(CH₃)₂OH substituent.

Structure (shown with Example 1.2):
Similar indane-HN-pyrimidine, with 5-CH(CH₃)OH (&1 stereocenter) and 4-NH₂.

Comparison of the post-emergence herbicidal activity of compounds according to the invention with compounds from WO 2010/076010 A1

| Example No. or Application No. | Dosage [g/ha] | Herbicidal action against [%] | | | | | | |
|---|---|---|---|---|---|---|---|---|
| | | MATIN | PHBPU | POLCO | STEME | VIOTR | VERPE | HORMU |
| 1.4 | 320 | 80 | 100 | 90 | 90 | | | |
|  | 80 | 40 | | 70 | 60 | 90 | | |
| (structure B) | 320 | 60 | 50 | 0 | 0 | | | |
|  | 80 | 0 | | 0 | 0 | 60 | | |

Structure B: indane (abs, abs) with methyl substituent on ring, linked via HN to pyrimidine bearing 4-NH₂ and 5-C(CH₃)₂OH.

TABLE 2-continued

| Cmpd | | | | | | | |
|---|---|---|---|---|---|---|---|
| 1.6 | 320 | | 100 | 80 | 100 | | |
| | 80 | 20 | | | 100 | 90 | |
| | 320 | | 50 | 0 | 0 | | |
| | 80 | 0 | | | 0 | 60 | |
| 1.7 | 320 | | 100 | 80 | | | 100 |
| | 80 | | 60 | 80 | | | 40 |
| | 320 | | 80 | 60 | | | 20 |
| | 80 | | 20 | 60 | | | 0 |
| 1.2 | 320 | | | 90 | | | |
| | 80 | 40 | | 90 | 90 | | |
| | 320 | | | 60 | | | |
| | 80 | 20 | | 60 | 70 | | |

The herbicidal effects compared in Table 1 (pre-emergence method) and in Table 2 (post-emergence method) confirm the good activity profile of the compounds 1.4 and 1.6 and also 1.7 and 1.2 according to the invention in comparison to comparative compounds known from the prior art.

In the 4 position of the pyrimidine, the comparative compounds according to the invention are either unsubstituted (4-H) or substituted by a substituent different from amino, e.g. by methyl (4-Me).

In contrast, the diaminopyrimidines already known from WO 2010/076010 A1 have an additional amino group in the 4 position of the pyrimidine.

The compounds according to the invention are distinguished by a surprisingly good activity profile.

TABLE 3a

Comparison of the pre-emergence herbicidal activity of compounds according to the invention with compounds from WO 2016/001118 A1

| Example No. or Application No. | Dosage [g/ha] | ALOMY | AVEFA | CYPES | ECHCG | LOLRI | SETVI | ABUTH |
|---|---|---|---|---|---|---|---|---|
| 1.6 | 320 | | 100 | | | | | 100 |
|  | 80 | | 80 | | | | | 90 |
| 1.26 from WO 2016/001118 A1 | 320 | | 70 | | | | | 0 |
|  | 80 | | 60 | | | | | 0 |
| 1.7 | 320 | | 90 | | | | | 100 |
|  | 80 | | | | | | | 90 |
| 1.26 from WO 2016/001118 A1 | 320 | | 70 | | | | | 0 |
|  | 80 | | | | | | | 0 |
| 1.8 | 320 | 100 | 100 | 70 | 100 | | 100 | 100 |
| 1.2 from WO 2016/001118 A1 | 320 | 20 | 0 | 0 | 80 | | 70 | 20 |

| Example No. or Application No. | Dosage [g/ha] | AMARE | PHBPU | POLCO | STEME | VIOTR | HORMU |
|---|---|---|---|---|---|---|---|
| 1.6 | 320 | 100 | | | | | |
|  | 80 | 80 | | | | | |
| 1.26 from WO 2016/001118 A1 | 320 | 60 | | | | | |
|  | 80 | 30 | | | | | |
| 1.7 | 320 | 80 | | | | | |
|  | 80 | 80 | | | | | |
| 1.26 from WO 2016/001118 A1 | 320 | 60 | | | | | |
|  | 80 | 30 | | | | | |
| 1.8 | 320 | 100 | 100 | 100 | 100 | | |
| 1.2 from WO 2016/001118 A1 | 320 | 0 | 80 | 70 | 50 | | |

TABLE 3b

Comparison of the post-emergence herbicidal activity of compounds according to the invention with compounds from WO 2016/001118 A1

| Example No. or Application No. | Dosage [g/ha] | ALOMY | AVEFA | ECHCG | LOLRI | SETVI | ABUTH | AMARE | MATIN |
|---|---|---|---|---|---|---|---|---|---|
| 1.6 | 320 | | 100 | | | | 90 | | |
|  | 80 | 90 | | | | 90 | 80 | 100 | |
| 1.26 from WO 2016/001118 A1 | 320 | | 80 | | | | 70 | | |
|  | 80 | 20 | | | | 60 | 50 | 80 | |
| 1.7 | 320 | | | | | | | | 90 |
|  | 80 | 80 | | | | 100 | | | |
| 1.26 from WO 2016/001118 A1 | 320 | | | | | | | | 50 |
|  | 80 | 20 | | | | 60 | | | |
| 1.8 | 320 | 70 | 100 | 100 | 100 | 100 | 90 | 100 | 100 |
| 1.2 from WO 2016/001118 A1 | 320 | 20 | 20 | 40 | | 0 | 20 | 80 | 30 |

| Example No. or Application No. | Dosage [g/ha] | PHBPU | POLCO | STEME | VIOTR | VERPE | HORMU |
|---|---|---|---|---|---|---|---|
| 1.6 | 320 | | | 100 | | | |
|  | 80 | | | 100 | | | |
| 1.26 from WO 2016/001118 A1 | 320 | | | 70 | | | |
|  | 80 | | | 50 | | | |
| 1.7 | 320 | | | 100 | | | |
|  | 80 | | | | | | |
| 1.26 from WO 2016/001118 A1 | 320 | | | 70 | | | |
|  | 80 | | | | | | |
| 1.8 | 320 | 80 | 90 | 100 | 90 | | |
| 1.2 from WO 2016/001118 A1 | 320 | 30 | 30 | 0 | 0 | | |

The herbicidal effects compared in Table 3a (pre-emergence method) and in Table 3b (post-emergence method) confirm the good activity profile of the compounds 1.6, 1.7 and 1.8 according to the invention in comparison to comparative compounds known from the prior art.

The comparative compounds according to the invention have a hydroxyalkyl radical in the 5 position of the pyrimidine (5-hydroxyalkyl).

In contrast, the monoaminopyrimidines already known from WO 2016/001118 A1 have a keto group in the 5 position of the pyrimidine (5-ketopyrimidine).

The compounds according to the invention are distinguished by a surprisingly good activity profile.

As well as a good profile of efficacy and/or good crop plant compatibility, the compounds of the formula (I) are notable for their inexpensive preparation, since the substances of the invention can be prepared from inexpensive and readily available precursors by inexpensive processes. It is therefore possible to dispense with the use of intermediates that are costly and difficult to obtain.

There follows a description of preferred, particularly preferred and very particularly preferred definitions of each of the individual substituents. The other substituents of the general formula (I) which are not specified hereinafter have the definition given above. The same also applies to the running number n, meaning that the running number n in the embodiments which follow is 0, 1 or 2.

TABLE 4a

Comparison of the pre-emergence herbicidal activity of compounds according to the invention with compounds from WO 2017/016914 A1

| Example No. or Application No. | Example No. | Dosage (g of a.i./ha) | ALOMY | ECHCG | LOLRI | SETVI | ABUTH | PHBPU | POLCO |
|---|---|---|---|---|---|---|---|---|---|
| compound according to the invention | 1.52 | 20 | 90 | 100 | 60 | 100 | 100 | 100 | 100 |
| WO 2017/016914 A1 | [structure] | 20 | 30 | 30 | 0 | 80 | 80 | 0 | 20 |
| compound according to the invention | 1.48 | 20 | 70 | 80 | 90 | 100 | 90 | 70 | 100 |
| WO 2017/016914 A1 | [structure] | 20 | 0 | 0 | 0 | 20 | 0 | 0 | 20 |

TABLE 4b

Comparison of the pre-emergence herbicidal activity of compounds according to the invention with compounds from WO 2017/016914 A1

| Example No. or Application No. | Example No. | Dosage (g of a.i./ha) | Herbicidal efficacy against | | | | | | |
|---|---|---|---|---|---|---|---|---|---|
| | | | ALOMY | ECHCG | SETVI | AMARE | MATIN | STEME | HORMU |
| compound according to the invention | 1.52 | 80 | 90 | 70 | 80 | 80 | 70 | 90 | 90 |
| WO 2017/016914 A1 | [structure] | 80 | 20 | 30 | 20 | 20 | 20 | 30 | 10 |
| compound according to the invention | 1.48 | 80 | 50 | 90 | 70 | 80 | 70 | 80 | 20 |
| WO 2017/016914 A1 | [structure] | 80 | 10 | 40 | 20 | 30 | 20 | 20 | 0 |

The herbicidal effects compared in Table 4a (pre-emergence method) and in Table 4b (post-emergence method) confirm the unexpected good activity profile of the compounds 1.48 and 1.52 according to the invention in comparison to comparative compounds known from WO 2017/016914 A1.

A first embodiment of the present invention encompasses compounds of the general formula (I) in which $R^{1a}$ is preferably selected from the group consisting of
hydrogen, cyano;
($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl;
($C_3$-$C_8$)-cycloalkyl which may be unsubstituted or mono- or polysubstituted in the cycloalkyl radical by ($C_1$-$C_6$)-alkyl and/or halogen;

$R^{1a}$ is particularly preferably selected from the group consisting of
hydrogen;
($C_1$-$C_3$)-alkyl, ($C_1$-$C_3$)-haloalkyl, ($C_2$-$C_3$)-alkenyl, ($C_2$-$C_3$)-alkynyl;

$R^{1a}$ very particularly preferably represents hydrogen, $CH_3$, $CH_2CH_3$, $CF_3$, $C(H)=CH_2$ or $C\equiv CH$;

$R^{1a}$ most preferably represents hydrogen, $CH_3$ or $CH_2CH_3$.

A second embodiment of the present invention encompasses compounds of the general formula (I) in which $R^{1b}$ is preferably selected from the group consisting of
cyano, C(O)OH, C(O)$NH_2$;
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_2$-$C_6$)-alkenyl, ($C_2$-$C_6$)-haloalkenyl;
($C_2$-$C_6$)-alkynyl, ($C_2$-$C_6$)-haloalkynyl;
($C_6$-$C_{14}$)-aryl which may be substituted in the aryl moiety in each case by halogen, ($C_1$-$C_6$)-alkyl and/or ($C_1$-$C_6$)-haloalkyl;
pyridyl which may in each case be substituted by halogen, ($C_1$-$C_6$)-alkyl and/or ($C_1$-$C_6$)-haloalkyl;
thienyl which may in each case be substituted by halogen, ($C_1$-$C_6$)-alkyl and/or ($C_1$-$C_6$)-haloalkyl;
($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;
($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;
cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl;

$R^{1b}$ is particularly preferably selected from the group consisting of
cyano;
$(C_1-C_4)$-alkyl, $(C_1-C_4)$-haloalkyl;
$(C_1-C_3)$-alkoxycarbonylmethyl, $(C_2-C_4)$-alkenyl, $(C_2-C_4)$-haloalkenyl;
$(C_2-C_4)$-alkynyl, $(C_2-C_4)$-haloalkynyl;
phenyl which may be substituted in the aryl moiety by halogen and/or methyl;
$CH_2$-phenyl (benzyl) which may be substituted in the aryl moiety by halogen and/or methyl;
$(C_1-C_6)$-cycloalkyl which may be unsubstituted or mono- or polysubstituted in the cycloalkyl radical by methyl and/or halogen;
$R^{1b}$ very particularly preferably represents cyano, $CH_3$, $CH_2CH_3$, $CH_2CH(CH_3)_2$, $CF_3$, $(C_1-C_2)$-alkoxycarbonylmethyl, $C(H)=CH_2$, $CH=C(CH_3)_2$, $(CH_2)_2CH=CH_2$, $C=CH$, $C=CCH_3$, phenyl, $CH_2$-phenyl (benzyl) or cyclopropyl.
$R^{1b}$ is most preferably selected from the group consisting of cyano, $CH_3$, $CH_2CH_3$, $CF_3$, $C(H)=CH_2$, $C=CH$ and $C=CCH_3$;

A third embodiment of the present invention encompasses compounds of the general formula (I) in which
if $R^{1a}$ does not represent hydrogen, $R^{1a}$ is preferably linked to $R^{1b}$ via a bond so that, together with the carbon to which these two radicals are attached, a saturated 3- to 6-membered carbocycle is formed which is unsubstituted or substituted by one or more substituents selected from the group consisting of methyl, trifluoromethyl, cyclopropyl;
if $R^{1a}$ does not represent hydrogen, $R^{1a}$ is particularly preferably linked to $R^{1b}$ via a bond so that, together with the carbon to which these two radicals are attached, a saturated 3- to 6-membered carbocycle is formed which is unsubstituted or substituted by one or more methyl groups, with an unsubstituted 3- to 6-membered carbocycle in which the ring elements are each formed by $CH_2$ units being particularly preferred;
if $R^{1a}$ does not represent hydrogen, $R^{1a}$ is very particularly preferably linked to $R^{1b}$ via a bond so that, together with the carbon to which these two radicals are attached, a saturated 3-membered carbocycle is formed which is unsubstituted or substituted by a methyl group;
if $R^{1a}$ does not represent hydrogen, RIB is most preferably linked to $R^{1b}$ via a bond so that, together with the carbon to which these two radicals are attached, a saturated 3-membered carbocycle is formed which is unsubstituted;

A fourth embodiment of the present invention encompasses compounds of the general formula (I) in which
$R^{2a}$ and $R^{2b}$ are each independently of one another preferably selected from the group consisting of hydrogen, $(C_1-C_6)$-alkyl, $(C_1-C_6)$-haloalkyl, $(C_1-C_6)$-alkoxy, $(C_1-C_6)$-alkoxy-$(C_1-C_6)$-alkyl, $(C_3-C_8)$-cycloalkyl, $(C_3-C_8)$-cycloalkyl-$(C_1-C_6)$-alkyl and $(C_3-C_8)$-cycloalkyl-$(C_1-C_6)$-haloalkyl, where the cycloalkyl radical is in each case unsubstituted or is substituted by $(C_1-C_6)$-alkyl and/or halogen;
$R^{2a}$ and $R^{2b}$ are each independently of one another particularly preferably selected from the group consisting of hydrogen, $(C_1-C_6)$-alkyl, $(C_1-C_6)$-haloalkyl, $(C_1-C_3)$-alkoxy, $(C_1-C_3)$-alkoxy-$(C_1-C_3)$-alkyl and $(C_3-C_6)$-cycloalkyl;
$R^{2a}$ and $R^{2b}$ are each independently of one another very particularly preferably selected from the group consisting of hydrogen, $CH_3$, $CH_2CH_3$, $CH(CH_3)_2$, $CF_3$, $CF_2H$, $CF_2Cl$, $CH(CH_3)F$, $C(CH_3)_2F$, cyclopropyl and $CH_2OCH_3$;

$R^{2a}$ and $R^{2b}$ most preferably each independently of one another are selected from the group consisting of hydrogen, $CH_3$, $CH(CH_3)F$ and $CF_2H$; where the combination $R^{2a}$ selected from the group consisting of hydrogen, $CH_3$, $CH(CH_3)F$ and $CF_2H$ and $R^{2b}$ representing hydrogen is given utmost preference.

A fifth embodiment of the present invention encompasses compounds of the general formula (I) in which
$R^3$ is preferably selected from the group consisting of
hydrogen;
$(C_1-C_3)$-alkylcarbonyl, $(C_1-C_3)$-haloalkylcarbonyl;
phenylcarbonyl which may in each case be substituted in the aryl moiety by halogen and/or methyl;
$(C_1-C_6)$-alkyl, $(C_1-C_6)$-haloalkyl;
$(C_2-C_6)$-alkenyl, $CH(CH_3)(C_2-C_3)$-alkenyl, $(C_2-C_6)$-haloalkenyl;
$(C_2-C_6)$-alkynyl, $CH(CH_3)(C_2-C_3)$-alkynyl, $(C_2-C_6)$-haloalkynyl;
$(C_1-C_3)$-alkoxycarbonyl-$(C_1-C_3)$-alkyl;
phenyl-$(C_1-C_3)$-alkyl which may in each case be substituted in the aryl moiety by halogen and/or methyl;
$(C_1-C_3)$-alkoxy-$(C_1-C_3)$-alkyl;
$(C_6-C_{14})$-aryl which may in each case be substituted in the aryl moiety by halogen;
$(C_1-C_3)$-trialkylsilyl;
$R^3$ is particularly preferably selected from the group consisting of
hydrogen;
$(C_1-C_4)$-alkylcarbonyl;
phenylcarbonyl (benzoyl)
$(C_1-C_3)$-alkyl;
$CH_2(C_2-C_3)$-alkenyl, $CH(CH_3)(C_2-C_3)$-alkenyl;
$CH_2(C_2-C_3)$-alkinyl, $CH(CH_3)(C_2-C_3)$-alkinyl;
$(C_1-C_3)$-alkoxycarbonylmethyl;
$CH_2$-phenyl (benzyl);
$CH_2$(4-F-phenyl);
$Si(CH_3)_3$,
where
$R^3$ is particularly preferably selected from the group consisting of
hydrogen;
$(C_1-C_3)$-alkyl,
$CH_2(C_2-C_3)$-alkenyl,
$CH_2(C_2-C_3)$-alkynyl,
$CH(CH_3)(C_2-C_3)$-alkenyl,
$CH(CH_3)(C_2-C_3)$-alkynyl,
$(C_1-C_2)$-alkoxycarbonylmethyl,
$R^3$ is most preferably selected from the group consisting of
hydrogen
$CH_3$, $CH_2CH_3$,
$CH_2CH=CH_2$, $CH_2C(CH_3)=CH_2$, $CH_2CH=CHCH_3$,
$CH_2C=CH$, $CH_2C=CCH_3$,
$CH(CH_3)CH=CH_2$,
$CH(CH_3)C=CH$ and
$CH_2C(O)OCH_3$, where
$R^3$ in the group mentioned above again particularly preferably represents hydrogen or $CH_3$, and
$R^3$ with utmost preference represents hydrogen.

A sixth embodiment of the present invention encompasses compounds of the general formula (I) in which
$R^4$ and $R^5$ are preferably each independently of one another selected from the group consisting of hydrogen, hydroxy, $(C_1-C_6)$-alkyl, $(C_1-C_6)$-alkylphenyl and $(C_1-C_6)$-alkoxy;
$R^4$ and $R^5$ are particularly preferably each independently of one another selected from the group consisting of hydrogen, $(C_1-C_6)$-alkyl and $(C_1-C_6)$-alkoxy;

$R^4$ and $R^5$ are very particularly preferably each independently of one another selected from the group consisting of hydrogen, $(C_1-C_3)$-alkyl, $(C_1-C_6)$-alkoxy $R^4$ and $R^5$ each independently of one another most preferably represent hydrogen or methyl.

In this sixth embodiment, it is especially preferable for at least one of the $R^4$ and $R^5$ radicals to represent hydrogen. In other words, when in each case at least one of the $R^4$ and $R^5$ radicals represents hydrogen and the other $R^4$ and $R^5$ radical does not represent hydrogen, namely especially $(C_1-C_6)$-alkyl, preferably methyl ($CH_3$).

A seventh embodiment of the present invention encompasses compounds of the general formula (I) in which $R^6$ and $R^7$ are preferably independently of one another selected from the group consisting of hydrogen, $(C_1-C_6)$-alkyl and $(C_6-C_{14})$-aryl;

$R^6$ and $R^7$ are particularly preferably independently of one another selected from the group consisting of hydrogen, methyl and phenyl;

$R^6$ and $R^7$ very particularly preferably each represent hydrogen or methyl;

$R^6$ and $R^7$ most preferably represent hydrogen.

An eighth embodiment of the present invention encompasses compounds of the general formula (I) in which $R^8$ is preferably selected from the group consisting of hydrogen, halogen, cyano, C(O)OH, $(C_1-C_6)$-alkyl, $(C_1-C_6)$-alkoxy, $(C_1-C_6)$-alkyloxycarbonyl and $(C_6-C_{14})$-aryl;

$R^8$ is particularly preferably selected from the group consisting of hydrogen, halogen, cyano, C(O)OH, $(C_1-C_3)$-alkyl, $(C_1-C_3)$-alkoxy, $(C_1-C_3)$-alkyloxycarbonyl and $(C_6-C_8)$-aryl;

$R^8$ is very particularly preferably selected from the group consisting of hydrogen, fluorine, chlorine, $CH_3$, methoxycarbonyl and phenyl;

$R^8$ most preferably represents hydrogen or $CH_3$.

A ninth embodiment of the present invention encompasses compounds of the general formula (I) in which $R^9$ is preferably selected from the group consisting of hydrogen, halogen, $(C_1-C_6)$-alkyl and $(C_1-C_6)$-alkoxy;

$R^9$ is particularly preferably selected from the group consisting of hydrogen, chlorine, fluorine and $(C_1-C_3)$-alkoxy;

$R^9$ is very particularly preferably selected from the group consisting of hydrogen, fluorine, chlorine and methoxy;

$R^9$ most preferably represents hydrogen.

A tenth embodiment of the present invention encompasses compounds of the general formula (I) in which $R^{10}$ is preferably selected from the group consisting of hydrogen, halogen, cyano, aminocarbonyl, hydroxycarbonyl, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl;

$R^{10}$ is particularly preferably selected from the group consisting of hydrogen, fluorine, chlorine, bromine, iodine, cyano, methoxy ($OCH_3$), $(C_1-C_3)$-alkyl, $(C_1-C_3)$-haloalkyl, $(C_1-C_3)$-alkoxy, $(C_2-C_4)$-alkenyl, $(C_2-C_4)$-alkynyl, $(C_1-C_3)$-alkyl-$(C_2-C_4)$-alkynyl, hydroxy-$(C_1-C_4)$-alkyl-$(C_2-C_4)$-alkynyl, $(C_1-C_3)$-alkoxy-$(C_2-C_4)$-alkynyl and phenyl-$(C_2-C_4)$-alkynyl;

$R^{10}$ is very particularly preferably selected from the group consisting of hydrogen, fluorine, chlorine, bromine, iodine, cyano, methyl, C≡CH and C≡$CCH_3$.

$R^{10}$ most preferably represents hydrogen or $CH_3$.

An eleventh embodiment of the present invention encompasses compounds of the general formula (I) in which $R^{11}$ is preferably selected from the group consisting of hydrogen and $(C_1-C_6)$-alkyl;

$R^{11}$ is particularly preferably selected from the group consisting of hydrogen and $(C_1-C_4)$-alkyl;

$R^{11}$ very particularly preferably represents hydrogen or methyl;

$R^{11}$ most preferably represents hydrogen.

A twelfth embodiment of the present invention encompasses compounds of the general formula (I) in which X is preferably selected from the group consisting of a chemical bond, $CH_2$, O, S, carbonyl, NH, CH($C_1-C_6$)-alkyl, N($C_1-C_6$)-alkyl, $OCH_2$ and $SCH_2$, where in the two last-mentioned groups the carbon atom is attached to the aromatic moiety and the heteroatom O or S is attached to the partially hydrogenated moiety of the amine;

X is particularly preferably selected from the group consisting of a chemical bond, $CH_2$, O, S, $CHCH_3$, $NCH_3$, $OCH_2$ and $SCH_2$, where in the two last-mentioned groups the carbon atom is attached to the aromatic moiety and the heteroatom O or S is attached to the partially hydrogenated moiety of the amine; and in which X most preferably represents a chemical bond, $CH_2$ or O.

In the context of the present invention, it is possible to combine the individual preferred, more preferred and even more preferred definitions of the substituents $R^{1a}$ to $R^{11}$ and X with one another as desired, where the running number n is 0, 1 or 2.

This means that the present invention encompasses compounds of the general formula (I) in which, for example, the substituent $R^{1a}$ has a preferred definition and the substituents $R^{1b}$ to $R^{14}$ have the general definition or else the substituent $R^{2a}$ has a preferred definition, the substituent $R^3$ has a particularly preferred or very particularly preferred definition and the remaining substituents have a general definition.

Three of these combinations of the definitions given above for the substituents $R^{1a}$ to $R^{11}$ and X are illustrated by way of example hereinafter and each are disclosed as further embodiments:

combination of the definitions each referred to above as being particularly preferred for the substituents $R^1$ to $R^{11}$ and X (thirteenth embodiment), combination of the definitions each referred to above as being very particularly preferred for the substituents $R^1$ to $R^{11}$ and X (fourteenth embodiment), and combination of the definitions each referred to above as being most preferred for the substituents $R^1$ to $R^{11}$ and X (fifteenth embodiment), and The aforementioned further embodiments that are based on the preferred combinations of the substituents are disclosed explicitly hereinafter for reasons of clarity:

A thirteenth embodiment of the present invention encompasses compounds of the general formula (I) in which $R^{1a}$ is selected from the group consisting of hydrogen, $(C_1-C_3)$-alkyl, $(C_1-C_3)$-haloalkyl, $(C_2-C_3)$-alkenyl and $(C_2-C_3)$-alkynyl;

$R^{1b}$ is selected from the group consisting of cyano, $(C_1-C_4)$-alkyl, $(C_1-C_4)$-haloalkyl, $(C_1-C_3)$-alkoxycarbonylmethyl, $(C_2-C_4)$-alkenyl, $(C_2-C_4)$-haloalkenyl, $(C_2-C_4)$-alkynyl, $(C_2-C_4)$-haloalkynyl, phenyl, which may be substituted in the aryl moiety by halogen and/or methyl, $CH_2$-phenyl (benzyl), which may be substituted in the aryl moiety by halogen and/or methyl, and $(C_3-C_6)$-cycloalkyl, which may be unsubstituted or mono- or polysubstituted in the cycloalkyl radical by methyl and/or halogen, where, if $R^{1a}$ does not represent hydrogen, $R^{1a}$ is linked to $R^{1b}$ via a bond so that, together with the carbon to which these two radicals are attached, a saturated 3- to 6-membered carbocycle is formed which is unsubstituted or substituted by one or more methyl groups, with an unsubstituted 3- to 6-membered carbocycle in which the ring elements are each formed by $CH_2$ units being particularly preferred;

$R^{2a}$ and $R^{2b}$ are each independently of one another selected from the group consisting of hydrogen, $(C_1-C_6)$-alkyl, $(C_1-C_6)$-haloalkyl, $(C_1-C_3)$-alkoxy, $(C_1-C_3)$-alkoxy-$(C_1-C_3)$-alkyl and $(C_3-C_6)$-cycloalkyl;

$R^3$ is selected from the group consisting of hydrogen, $(C_1-C_4)$-alkylcarbonyl, phenylcarbonyl (benzoyl), $(C_1-C_3)$-alkyl, $CH_2(C_2-C_3)$-alkenyl, $CH(CH_3)(C_2-C_3)$-alkenyl, $CH_2(C_2-C_3)$-alkynyl, $CH(CH_3)(C_2-C_3)$-alkynyl, $(C_1-C_3)$-alkoxycarbonylmethyl, $CH_2$-phenyl (benzyl), $CH_2$(4-F-phenyl) and $Si(CH_3)_3$.

$R^4$ and $R^5$ are each independently of one another selected from the group consisting of hydrogen, hydroxy, $(C_1-C_6)$-alkyl, $(C_1-C_6)$-alkylphenyl and $(C_1-C_6)$-alkoxy;

$R^6$ and $R^7$ are independently of one another selected from the group consisting of hydrogen, methyl and phenyl;

$R^8$ is selected from the group consisting of hydrogen, halogen, cyano, C(O)OH, $(C_1-C_3)$-alkyl, $(C_1-C_3)$-alkoxy, $(C_1-C_3)$-alkyloxycarbonyl and $(C_6-C_8)$-aryl;

$R^9$ is selected from the group consisting of hydrogen, chlorine, fluorine and $(C_1-C_3)$-alkoxy;

$R^{10}$ is selected from the group consisting of hydrogen, fluorine, chlorine, bromine, iodine, cyano, methoxy ($OCH_3$), $(C_1-C_3)$-alkyl, $(C_1-C_3)$-haloalkyl, $(C_1-C_3)$-alkoxy, $(C_2-C_4)$-alkenyl, $(C_2-C_4)$-alkynyl, $(C_1-C_3)$-alkyl-$(C_2-C_4)$-alkynyl, hydroxy-$(C_1-C_3)$-alkyl-$(C_2-C_4)$-alkynyl, $(C_1-C_3)$-alkoxy-$(C_2-C_4)$-alkynyl and phenyl-$(C_2-C_4)$-alkynyl;

$R^{11}$ is selected from the group consisting of hydrogen and $(C_1-C_4)$-alkyl;

X represents a chemical bond or O, S, carbonyl, $CH_2$, NH, $CHCH_3$, $NCH_3$, $C(CH_3)_2$, $OCH_2$ and $SCH_2$, where in the two last-mentioned groups the carbon atom is attached to the aromatic moiety and the heteroatom O or S is attached to the partially hydrogenated moiety of the amine.

A fourteenth embodiment of the present invention encompasses compounds of the general formula (I) in which $R^{1a}$ is selected from the group consisting of hydrogen, $CH_3$, $CH_2CH_3$, $CF_3$, $C(H)=CH_2$ and $C\equiv CH$;

$R^{1b}$ is selected from the group consisting of cyano, $CH_3$, $CH_2CH_3$, $CH_2CH(CH_3)_2$, $CF_3$, $(C_1-C_2)$-alkoxycarbonylmethyl, $C(H)=CH_2$, $CH=C(CH_3)_2$, $(CH_2)_2CH=CH_2$, $C\equiv CH$, $C\equiv CCH_3$, phenyl, $CH_2$-phenyl (benzyl) and cyclopropyl, where, if $R^{1a}$ does not represent hydrogen, $R^{1a}$ is linked to $R^{1b}$ via a bond so that, together with the carbon to which these two radicals are attached, a saturated 3-membered carbocycle is formed which is unsubstituted or substituted by a methyl group;

$R^{2a}$ and $R^{2b}$ are each independently of one another very particularly preferably selected from the group consisting of hydrogen, $CH_3$, $CH_2CH_3$, $CH(CH_3)_2$, $CF_3$, $CF_2H$, $CF_2Cl$, $CH(CH_3)F$, $C(CH_3)_2F$, cyclopropyl and $CH_2OCH_3$;

$R^3$ is selected from the group consisting of hydrogen, $CH_3$, $CH_2CH_3$, $CH_2CHCH_2$, $CH_2C(CH_3)=CH_2$, $CH_2CH=CHCH_3$, $CH_2C\equiv CH$, $CH_2C\equiv CCH_3$, $CH(CH_3)CH=CH_2$, $CH(CH_3)C\equiv CH$ and $CH_2C(O)OCH_3$;

$R^4$ and $R^5$ are each independently of one another selected from the group consisting of hydrogen, $(C_1-C_6)$-alkyl and $(C_1-C_6)$-alkoxy;

$R^6$ and $R^7$ independently of one another represent hydrogen or methyl;

$R^8$ is selected from the group consisting of hydrogen, fluorine, chlorine, $CH_3$, methoxycarbonyl and phenyl, $R^9$ is selected from the group consisting of hydrogen, fluorine, chlorine and methoxy;

$R^{10}$ is selected from the group consisting of hydrogen, fluorine, chlorine, bromine, iodine, cyano, methyl, $C\equiv CH$ and $C\equiv CCH_3$;

$R^{11}$ represents hydrogen or methyl; and

X represents a chemical bond or O, S, $CH_2$, $CHCH_3$, $OCH_2$, $SCH_2$ and $NCH_3$, where in the two last-mentioned groups the carbon atom is attached to the aromatic moiety and the heteroatom O or S is attached to the partially hydrogenated moiety of the amine.

A fifteenth embodiment of the present invention encompasses compounds of the general formula (I) in which $R^{1a}$ is selected from the group consisting of hydrogen, $CH_3$ and $CH_2CH_3$;

$R^{1b}$ is selected from the group consisting of cyano, $CH_3$, $CH_2CH_3$, $CF_3$, $C(H)=CH_2$, $C\equiv CH$ and $C\equiv CCH_3$;

where, if $R^{1a}$ does not represent hydrogen, $R^{1a}$ is linked to $R^{1b}$ via a bond so that, together with the carbon to which these two radicals are attached, a saturated 3-membered carbocycle is formed which is unsubstituted;

$R^{2a}$ and $R^{2b}$ each independently of one another are selected from the group consisting of hydrogen, $CH_3$, $CH(CH_3)F$ and $CF_2H$;

$R^3$ is selected from the group consisting of hydrogen and $CH_3$;

$R^4$ and $R^5$ each independently of one another represent hydrogen or methyl;

$R^6$ and $R^7$ each represents hydrogen;

$R^8$ represents hydrogen or $CH_3$;

$R^9$ represents hydrogen;

$R^{10}$ represents hydrogen or $CH_3$;

$R^{11}$ represents hydrogen; and

X represents a chemical bond, $CH_2$ or O.

In the context of the present invention, the compound of the general formula (I) also includes compounds quaternized on a nitrogen atom by a) protonation, b) alkylation or c) oxidation. In this respect, particular mention should be made of the corresponding N-oxides.

The compounds of the formula (I) are capable of forming salts. Salts may be formed by the action of a base on those compounds of the formula (I) that bear an acidic hydrogen atom. Suitable bases are, for example, organic amines such as trialkylamines, morpholine, piperidine or pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula [NRR'R''R'''] in which R to R''' each independently of one another represent an organic radical, in particular alkyl, aryl, aralkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugated base of the acid as the anion.

Suitable substituents present in deprotonated form, such as, for example, sulfonic acids or carboxylic acids, may form inner salts with groups which for their part can be protonated, such as amino groups.

The compounds of the formula (I) and their salts are also referred to for short hereinafter as "compounds (I)" according to the invention or used in accordance with the invention.

In the general formula (I) and in all the other formulae of the present invention, the radicals alkyl, alkoxy, haloalkyl, haloalkoxy, alkylamino, alkylthio, haloalkylthio and the corresponding unsaturated and/or substituted radicals can in each case be straight-chain or branched in the carbon skeleton. Unless stated specifically, preference is given for these radicals to the lower carbon skeletons, for example those having 1 to 6 carbon atoms, in particular 1 to 4 carbon atoms, or in the case of unsaturated groups having 2 to 6 carbon atoms, in particular 2 to 4 carbon atoms. Alkyl radicals, both alone and in the composite definitions such as alkoxy, haloalkyl, etc., are, for example, methyl, ethyl, n-propyl or isopropyl, n-butyl, isobutyl, tert-butyl or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; where at least one double bond or triple bond is present, preferably one double bond or triple bond, respectively. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can be present in bi- or tricyclic form.

If haloalkyl groups and haloalkyl radicals of haloalkoxy, haloalkylthio, haloalkenyl, haloalkynyl inter alia are stated, the lower carbon skeletons of these radicals having, for example, 1 to 6 carbon atoms or 2 to 6 carbon atoms, in particular 1 to 4 carbon atoms or preferably 2 to 4 carbon atoms, and the corresponding unsaturated and/or substituted radicals are in each case straight-chain or branched in the carbon skeleton. Examples are difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, in particular 1 to 6 carbon atoms, or preferably 2 to 4 carbon atoms, and also the corresponding unsaturated and/or substituted radicals in the carbon skeleton which may in each case be straight-chain or branched. Examples are methylene, ethylene, n- and isopropylene and n-, s-, iso-, t-butylene.

Hydroxyalkyl groups in these radicals are the lower carbon skeletons, for example those having 1 to 6 carbon atoms, especially 1 to 4 carbon atoms, and also the corresponding unsaturated and/or substituted radicals in the carbon skeleton which may in each case be straight-chain or branched. Examples of these are 1,2-dihydroxyethyl and 3-hydroxypropyl.

Halogen is fluorine, chlorine, bromine or iodine. Haloalkyl, -alkenyl and -alkynyl are alkyl, alkenyl and alkynyl partly or fully substituted by halogen, preferably by fluorine, chlorine or bromine, especially by fluorine and/or chlorine, for example monohaloalkyl, perhaloalkyl, $CF_3$, $CF_2Cl$, $CHF_2$, $CH_2F$, $CF_3CF_2$, $CH_2FCHCl$, $CCl_3$, $CHCl_2$, $CH_2CH_2Cl$ haloalkoxy is, for example, $OCF_3$, $OCHF_2$, $OCH_2F$, $CF_3CF_2O$, $OCH_2CF_3$ and $OCH_2CH_2Cl$; the same correspondingly applies to haloalkenyl and other halogen-substituted radicals.

Aryl is a monocyclic, bicyclic or polycyclic aromatic system, for example phenyl or naphthyl, preferably phenyl.

Primarily for reasons of higher herbicidal activity, better selectivity and/or better preparability, compounds of the general formula (I) according to the invention or the agrochemical salts or quaternary N derivatives thereof that are of particular interest are those in which individual radicals have one of the preferred definitions already specified or specified below, or especially those in which one or more of the preferred definitions already specified or specified below occur in combination.

The abovementioned general or preferred radical definitions apply both to the end products of the general formula (I) and, correspondingly, to the starting materials and intermediates required in each case for the preparation. These radical definitions can be exchanged for one another, i.e. including between the given preferred ranges.

If tautomers are possible, the form described embraces all possible tautomeric structures. As shown below, when, for example $R^{2a}$ and/or $R^{2b}$=hydroxyl, the possible keto tautomers are likewise embraced.

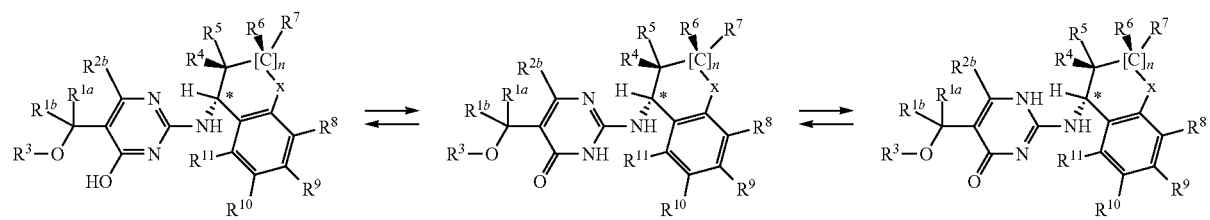

(I)

The present compounds of the general formula (I) have, at the bonding site to the aminopyrimidine, a chiral carbon atom which, in the structure shown below, is indicated by the marker (*):

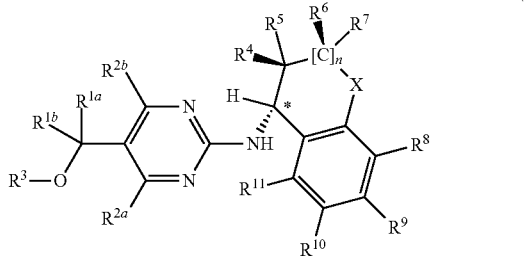

(I)

According to the rules of Cahn, Ingold and Prelog (CIP rules), this carbon atom can have either an (R) configuration or an (S) configuration.

The present invention encompasses compounds of the general formula (I) both with (S) and with (R) configuration, meaning that the present invention encompasses the compounds of the general formula (I) in which the carbon atom in question has (1) an (R) configuration; or
(2) an (S) configuration.

In addition, the scope of the present invention also encompasses (3) any mixtures of compounds of the general formula (I) having an (R) configuration (compounds of the general formula (I-(R)) with compounds of the general formula (I) having an (S) configuration (compounds of the general formula (I-S)), the present invention also encompassing a racemic mixture of the compounds of the general formula (I) having (R) and (S) configuration.

However, within the context of the present invention, preference is given particularly to compounds of the general formula (I) having (R) configuration with a selectivity of 60 to 100%, preferably 80 to 100%, especially 90 to 100%, very particularly 95 to 100%, where the particular (R) compound is present with an enantioselectivity of in each case more than 50% ee, preferably 60 to 100% ee, especially 80 to 100% ee, very particularly 90 to 100%/o ee, most preferably 95 to 100% ee, based on the total content of (R) compound in question.

Accordingly, the present invention relates especially to compounds of the general formula (I*) in which the stereochemical configuration on the carbon atom marked by (*) is present with a stereochemical purity of 60 to 100% (R), preferably 80 to 100% (R), especially 90 to 100% (R), very particularly 95 to 100% (R).

Taking into account the Cahn, Ingold and Prelog rule, at the carbon atom marked by (*) there may also be a situation in which, owing to the priority of the substituents in question, the (S) configuration is preferred at the carbon atom marked by (*). This is the case, for example, when the radicals $R^4$ and/or $R^5$ correspond to a $C_1$-$C_6$-alkoxy radical.

Accordingly, within the context of the present invention, preference is given especially to compounds of the general formula (I) whose spatial arrangement corresponds to that of the compounds of the general formula (I) where $R^4$ and $R^5$=hydrogen having the (R) configuration, with a selectivity of 60 to 100%, preferably 80 to 100%, especially 9) to 100%, very particularly 95 to 100%, where the respective (R)-analogous compound is present with an enantioselectivity of in each case more than 50% ee, preferably 60 to 100% ee, especially 80 to 100% ee, very particularly 90 to 100% ee, most preferably 95 to 100% ee, based on the total content of (R)-analogous compound in question. Accordingly, the present invention relates especially to compounds of the general formula (I) in which the stereochemical configuration on the carbon atom marked by (*) is present with a stereochemical purity of 60 to 100% (R or R analog), preferably 80 to 100% (R or R analog), especially 90 to 100% (R or R analog), very particularly 95 to 100% (R or R analog).

In particular, the compounds of the general formula (I) according to the invention may have further centers of chirality at the carbon atoms marked by () and (*):

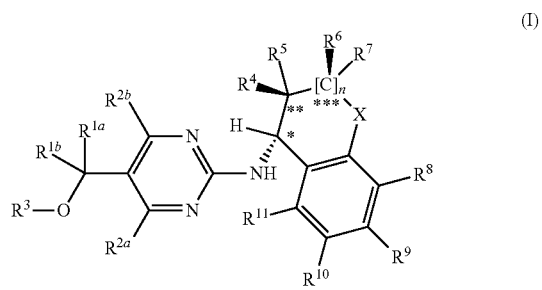

(I)

In the context of the present invention, any stereochemical configurations are possible at the carbon atoms marked by (*), () and (*):

| Configuration of carbon atom (*) | Configuration of carbon atom () | Configuration of carbon atom (*) |
|---|---|---|
| R | R | R |
| R | R | S |
| R | S | R |
| S | R | R |
| R | S | S |
| S | R | S |
| S | S | R |
| S | S | S |

In addition, depending on the respective radicals chosen, further stereoelements may be present in the compounds of the general formula (I) according to the invention.

If, for example, one or more alkenyl groups are present, diastereomers (Z and E isomers) may occur.

If, for example, one or more asymmetric carbon atoms are present, enantiomers and diastereomers may occur.

Corresponding stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention thus also relates to all stereoisomers which are encompassed by the general formula (I) but are not shown in their specific stereo form, and to mixtures thereof.

The possible combinations of the various substituents of the general formula (I) should be understood such that the general principles of the construction of chemical compounds have to be observed, i.e. the formula (I) does not encompass any compounds known by the person skilled in the art to be chemically impossible.

Examples of the compounds of the general formula (I) are shown below in tabular form.

Table 1 below specifies the substituents defined in general terms in formula (I). In this table:

"StNH" is the stereochemical arrangement at the carbon atom to which the nitrogen atom and the hydrogen atom are attached, "StR⁴R⁵" and "StR⁶R⁷" are analogously the carbon atoms to which the respective substituents are attached,
the bond of the substituents is on the left in each case,
if two binding sites are given for X, the left bond attaches to the aromatic ring and the right bond to the hydrogenated part of the bicyclic amine,
a hyphen "-" denotes a direct bond, and
if n=0, the table does not contain an entry in the corresponding field for $R^6$ and $R^7$.

TABLE 5

| No. | $R^{1a}$ | $R^{1b}$ | $R^{2a}$ | $R^{2b}$ | $R^3$ | St N H | $R^4$ | $R^5$ |
|---|---|---|---|---|---|---|---|---|
| 1.1 | H | $CH_3$ | H | H | H | rac | H | H |
| 1.2 | H | $CH_3$ | H | H | H | R | $CH_3$ | H |
| 1.3 | H | $CH_3$ | H | H | $CH_2$(4-F—Ph) | R | $CH_3$ | H |
| 1.4 | $CH_3$ | $CH_3$ | H | H | H | R | $CH_3$ | H |
| 1.5 | $CH_3$ | $CH_3$ | H | H | H | R | H | H |
| 1.6 | $CH_3$ | $CH_3$ | $CH_3$ | H | H | R | $CH_3$ | H |
| 1.7 | H | $CH_3$ | $CH_3$ | H | H | R | $CH_3$ | H |
| 1.8 | $CH_3$ | $CH_3$ | H | H | H | R | H | H |
| 1.9 | $CH_3$ | $CH_3$ | H | H | H | rac | H | H |
| 1.10 | $CH_2CH_3$ | $CH_2CH_3$ | H | H | H | R | $CH_3$ | H |
| 1.11 | $CH_3$ | $CF_3$ | H | H | H | R | $CH_3$ | H |
| 1.12 | $CH_3$ | $CH_3$ | $CH_3$ | H | H | R | H | H |
| 1.13 | H | $CH_3$ | $CH_3$ | H | H | R | H | H |
| 1.14 | $CH_3$ | $CH_2CH_3$ | H | H | H | R | $CH_3$ | H |
| 1.15 | $CH_3$ | C(H)=$CH_2$ | H | H | H | R | $CH_3$ | H |
| 1.16 | $CH_3$ | CN | H | H | $Si(CH_3)_3$ | R | $CH_3$ | H |
| 1.17 | $CH_3$ | $CH_3$ | $CHF_2$ | H | H | R | $CH_3$ | H |
| 1.18 | $CH_3$ | C≡CH | H | H | H | R | $CH_3$ | H |
| 1.19 | H | $CH_3$ | $CH(CH_3)F$ | H | H | R | $CH_3$ | H |
| 1.20 | $CH_3$ | cyclopropyl | H | H | H | R | $CH_3$ | H |
| 1.21 | $CH_3$ | Ph | H | H | H | R | $CH_3$ | H |
| 1.22 | $CH_3$ | C≡$CCH_3$ | H | H | H | R | $CH_3$ | H |
| 1.23 | $CH_3$ | $CH_3$ | $CH(CH_3)F$ | H | H | R | $CH_3$ | H |
| 1.24 | $CH_3$ | $CH_3$ | H | H | $CH_3$ | R | $CH_3$ | H |
| 1.25 | $CH_3$ | $CH_2CH(CH_3)_2$ | H | H | H | R | $CH_3$ | H |
| 1.26 | $CH_3$ | $CH_2Ph$ | H | H | H | R | $CH_3$ | H |
| 1.27 | $CH_3$ | CH=$C(CH_3)_2$ | H | H | H | R | $CH_3$ | H |
| 1.28 | $CH_3$ | $(CH_2)_2CH$=$CH_2$ | H | H | H | R | $CH_3$ | H |
| 1.29 | $CH_3$ | $CH_3$ | H | H | H | R | $CH_3$ | H |
| 1.30 | $CH_3$ | $CH_3$ | H | H | H | R | H | H |
| 1.31 | $CH_3$ | $CH_3$ | H | H | H | R | H | H |
| 1.32 | $CH_3$ | $CH_3$ | H | H | H | S | OH | H |
| 1.33 | $CH_3$ | $CH_3$ | H | H | H | S | $OCH_3$ | H |
| 1.34 | $CH_3$ | $CH_3$ | H | H | H | R | H | H |
| 1.35 | $CH_3$ | $CH_3$ | H | H | H | R | H | H |
| 1.36 | $CH_3$ | $CH_3$ | H | H | H | R | $CH_3$ | H |
| 1.37 | $CH_3$ | $CH_3$ | H | H | H | R | H | H |
| 1.38 | $CH_3$ | $CH_3$ | H | H | H | R | H | H |
| 1.39 | $CH_3$ | $CH_3$ | H | H | H | rac | H | H |
| 1.40 | $CH_3$ | $CH_3$ | H | H | H | rac | H | H |
| 1.41 | $CH_3$ | $CH_3$ | H | H | H | rac | H | H |
| 1.42 | $CH_3$ | $CH_3$ | H | H | H | R | H | H |
| 1.43 | $CH_3$ | $CH_3$ | H | H | H | rac | H | H |
| 1.44 | $CH_3$ | $CH_3$ | $CH_3$ | H | H | rac | H | H |
| 1.45 | H | $CH_3$ | $CH_3$ | H | H | S | OH | H |
| 1.46 | H | $CH_3$ | $CH_3$ | H | H | rac | H | H |
| 1.47 | H | $CH_3$ | $CH_3$ | H | H | R | H | H |
| 1.48 | H | $CH_3$ | $CH_3$ | H | H | R | H | H |
| 1.49 | H | $CH_3$ | $CH_3$ | H | H | R | H | H |
| 1.50 | H | $CH_3$ | $CH_3$ | H | H | R | H | H |
| 1.51 | $CH_3$ | $CH_3$ | $CH_3$ | H | H | R | $CH_3$ | H |
| 1.52 | $CH_3$ | $CH_3$ | $CH_3$ | H | H | rac | H | H |
| 1.53 | $CH_3$ | $CH_3$ | $CH_3$ | H | H | R | H | H |
| 1.54 | $CH_3$ | $CH_3$ | $CH_3$ | H | H | R | H | H |
| 1.55 | $CH_3$ | $CH_3$ | H | H | H | R | $CH_3$ | H |
| 1.56 | $CH_3$ | $CH_3$ | H | H | H | S | OH | H |
| 1.57 | $CH_3$ | $CH_3$ | $CH_3$ | H | H | R | H | H |
| 1.58 | $CH_2CH_3$ | $CF_3$ | H | H | H | R | $CH_3$ | H |
| 1.59 | $CH_3$ | $CH_3$ | H | H | H | rac | H | H |
| 1.60 | H | $CH_3$ | H | H | H | rac | H | H |
| 1.61 | $CH_3$ | 1-methylcyclopropyl | H | H | H | R | $CH_3$ | H |
| 1.62 | $CH_3$ | $CH_3$ | H | H | $CH_2CH_3$ | R | $CH_3$ | H |
| 1.63 | $CH_3$ | $CH_3$ | H | H | $CH_2C(CH_3)$=$CH_2$ | R | $CH_3$ | H |
| 1.64 | $CH_3$ | $CF_3$ | H | H | H | R | H | H |
| 1.65 | $CH_3$ | $CH_2C(O)OCH_3$ | H | H | H | R | $CH_3$ | H |
| 1.66 | $CH_3$ | $CH_3$ | H | H | $CH_2C(O)OCH_3$ | R | $CH_3$ | H |
| 1.67 | $CH_3$ | $CF_3$ | H | H | H | R | H | H |

TABLE 5-continued

| No. | | | | | | | | | |
|---|---|---|---|---|---|---|---|---|---|
| 1.68 | CH$_3$ | CF$_3$ | H | H | H | rac | H | H | |
| 1.69 | CH$_3$ | CF$_3$ | H | H | H | R | H | H | |
| 1.70 | CH$_3$ | CF$_3$ | H | H | H | rac | H | H | |
| 1.71 | CH$_3$ | CF$_3$ | H | H | H | S | OCH$_3$ | H | |
| 1.72 | CH$_3$ | CH$_3$ | H | H | CH$_2$C≡CH | R | CH$_3$ | H | |
| 1.73 | CH$_3$ | CH$_3$ | H | H | CH$_2$CH=CH$_2$ | R | CH$_3$ | H | |
| 1.74 | CF$_3$ | C≡CCH$_3$ | H | H | H | R | CH$_3$ | H | |
| 1.75 | CF$_3$ | C≡CH | H | H | H | R | CH$_3$ | H | |
| 1.76 | CH$_3$ | CH$_3$ | H | H | CH$_2$-cyclopropyl | R | CH$_3$ | H | |
| 1.77 | CH$_3$ | CH$_3$ | H | H | CH$_2$-phenyl | R | CH$_3$ | H | |
| 1.78 | H | CF$_3$ | H | H | CH$_3$ | R | CH$_3$ | H | |
| 1.79 | CH$_3$ | CF$_3$ | CH$_3$ | H | H | R | CH$_3$ | H | |
| 1.80 | H | CF$_3$ | H | H | H | R | CH$_3$ | H | |
| 1.81 | CH$_3$ | CF$_3$ | CH$_3$ | H | H | rac | H | H | |
| 1.82 | CH$_3$ | CH$_3$ | H | H | H | R | H | H | |
| 1.83 | CH$_3$ | CF$_3$ | CH$_3$ | H | H | R | H | H | |
| 1.84 | CH$_3$ | CF$_3$ | H | H | H | R | H | H | |
| 1.85 | CH$_3$ | CH$_3$ | H | H | CH$_2$CH=CH(CH$_3$) | R | CH$_3$ | H | |
| 1.86 | CH$_3$ | CH$_3$ | H | H | CH$_2$C≡CCH$_3$ | R | CH$_3$ | H | |
| 1.87 | CH$_3$ | CH$_3$ | H | H | CH(CH$_3$)C≡CH | R | CH$_3$ | H | |
| 1.88 | H | CH$_3$ | CH$_3$ | H | CH$_2$C(CH$_3$)=CH$_2$ | R | CH$_3$ | H | |
| 1.89 | CH$_3$ | CF$_3$ | CH$_3$ | H | H | R | H | H | |
| 1.90 | H | CH$_3$ | CH$_3$ | H | CH$_3$ | R | CH$_3$ | H | |
| 1.91 | H | CH$_3$ | CH$_3$ | H | CH$_2$CH=CH(CH$_3$) | R | CH$_3$ | H | |
| 1.92 | CH$_3$ | CF$_3$ | CH$_3$ | H | H | R | H | H | |
| 1.93 | CH$_3$ | CF$_3$ | CH$_3$ | H | H | rac | H | H | |
| 1.94 | CH$_3$ | CF$_3$ | CH$_3$ | H | H | R | H | H | |
| 1.95 | CH$_3$ | CF$_3$ | CH$_3$ | H | H | R | H | H | |
| 1.96 | CH$_3$ | CF$_3$ | CH$_3$ | H | H | R | H | H | |
| 1.97 | CH$_3$ | CH$_2$C(O)OCH$_3$ | CH$_3$ | H | H | R | CH$_3$ | H | |
| 1.98 | H | CH$_3$ | CH$_3$ | H | CH(CH$_3$)CH=CH$_2$ | R | CH$_3$ | H | |
| 1.99 | CH$_3$ | CH$_3$ | H | H | CH(CH$_3$)CH=CH$_2$ | R | CH$_3$ | H | |
| 1.100 | CH$_3$ | CH$_3$ | CH$_3$ | H | H | R | H | H | |
| 1.101 | CH$_3$ | CH$_3$ | H | H | H | R | H | H | |
| 1.102 | CH$_3$ | CH$_3$ | CH$_3$ | H | H | R | H | H | |
| 1.103 | CH$_3$ | CF$_3$ | H | H | H | R | H | H | |
| 1.104 | CH$_3$ | CF$_3$ | CH$_3$ | H | H | R | H | H | |
| 1.105 | CH$_3$ | CH$_3$ | H | H | H | R | H | H | |
| 1.106 | CH$_3$ | CH$_3$ | CH$_3$ | H | H | R | H | H | |
| 1.107 | CH$_3$ | CH$_3$ | H | H | H | R | H | H | |
| 1.108 | CH$_3$ | CF$_3$ | CH$_3$ | H | H | R | H | H | |
| 1.109 | CH$_3$ | CH$_3$ | H | H | H | R | H | H | |
| 1.110 | CH$_3$ | CH$_3$ | CH$_3$ | H | H | R | H | H | |
| 1.111 | CH$_3$ | CF$_3$ | H | H | H | R | H | H | |
| 1.112 | CH$_3$ | CF$_3$ | CH$_3$ | H | H | R | H | H | |
| 1.113 | CH$_3$ | CH$_3$ | H | H | H | R | H | H | |
| 1.114 | CH$_3$ | CH$_3$ | CH$_3$ | H | H | R | H | H | |
| 1.115 | CH$_3$ | CH$_3$ | H | H | H | R | H | H | |
| 1.116 | CH$_3$ | CF$_3$ | CH$_3$ | H | H | R | H | H | |
| 1.117 | CH$_3$ | CH$_3$ | H | H | H | R | H | H | |
| 1.118 | CH$_3$ | CH$_3$ | CH$_3$ | H | H | R | H | H | |
| 1.119 | CH$_3$ | CF$_3$ | H | H | H | R | H | H | |
| 1.120 | CH$_3$ | CF$_3$ | CH$_3$ | H | H | R | H | H | |

| No. | St | R$^4$ | R$^5$ | R$^6$ | R$^7$ | n | R$^8$ | R$^9$ | R$^{10}$ | R$^{11}$ | X |
|---|---|---|---|---|---|---|---|---|---|---|---|
| 1.1 | | | | H | H | 2 | H | H | H | H | — |
| 1.2 | S | | | H | H | 1 | H | H | CH$_3$ | H | — |
| 1.3 | S | | | H | H | 1 | H | H | CH$_3$ | H | — |
| 1.4 | S | | | H | H | 1 | H | H | CH$_3$ | H | — |
| 1.5 | | | | H | H | 1 | H | H | CH$_3$ | H | — |
| 1.6 | S | | | H | H | 1 | H | H | CH$_3$ | H | — |
| 1.7 | S | | | H | H | 1 | H | H | CH$_3$ | H | — |
| 1.8 | | | | H | H | 2 | H | H | H | H | — |
| 1.9 | | | | H | H | 1 | H | H | H | H | O |
| 1.10 | S | | | H | H | 1 | H | H | CH$_3$ | H | — |
| 1.11 | S | | | H | H | 1 | H | H | CH$_3$ | H | — |
| 1.12 | | | | H | H | 1 | H | H | CH$_3$ | H | — |
| 1.13 | | | | H | H | 1 | H | H | CH$_3$ | H | — |
| 1.14 | S | | | H | H | 1 | H | H | CH$_3$ | H | — |
| 1.15 | S | | | H | H | 1 | H | H | CH$_3$ | H | — |
| 1.16 | S | | | H | H | 1 | H | H | CH$_3$ | H | — |
| 1.17 | S | | | H | H | 1 | H | H | CH$_3$ | H | — |
| 1.18 | S | | | H | H | 1 | H | H | CH$_3$ | H | — |
| 1.19 | S | | | H | H | 1 | H | H | CH$_3$ | H | — |
| 1.20 | S | | | H | H | 1 | H | H | CH$_3$ | H | — |
| 1.21 | S | | | H | H | 1 | H | H | CH$_3$ | H | — |
| 1.22 | S | | | H | H | 1 | H | H | CH$_3$ | H | — |

TABLE 5-continued

| | | | | | | | | | |
|---|---|---|---|---|---|---|---|---|---|
| 1.23 | S | H | H | 1 | H | H | CH$_3$ | H | — |
| 1.24 | S | H | H | 1 | H | H | CH$_3$ | H | — |
| 1.25 | S | H | H | 1 | H | H | CH$_3$ | H | — |
| 1.26 | S | H | H | 1 | H | H | CH$_3$ | H | — |
| 1.27 | S | H | H | 1 | H | H | CH$_3$ | H | — |
| 1.28 | S | H | H | 1 | H | H | CH$_3$ | H | — |
| 1.29 | S | H | H | 1 | H | H | H | H | — |
| 1.30 | | H | H | 1 | H | H | H | H | — |
| 1.31 | | H | H | 1 | H | H | CH$_2$CH$_3$ | H | — |
| 1.32 | S | H | H | 1 | H | H | H | H | — |
| 1.33 | S | H | H | 1 | H | H | H | H | — |
| 1.34 | | H | H | 2 | OCH$_3$ | H | H | H | — |
| 1.35 | | H | H | 2 | H | H | CH$_3$ | H | — |
| 1.36 | S | H | H | 2 | H | H | CH$_2$CH$_3$ | H | — |
| 1.37 | | H | H | 2 | H | F | H | H | — |
| 1.38 | | H | H | 1 | H | H | CH$_3$ | H | O |
| 1.39 | | H | H | 1 | H | H | F | H | O |
| 1.40 | | | | 0 | H | H | H | H | O |
| 1.41 | | H | H | 2 | CH$_3$ | H | H | H | — |
| 1.42 | | H | H | 2 | CH$_3$ | H | H | H | — |
| 1.43 | | H | H | 2 | H | H | CH$_3$ | H | — |
| 1.44 | | H | H | 2 | OCH$_3$ | H | H | H | — |
| 1.45 | S | H | H | 1 | H | H | H | H | — |
| 1.46 | | H | H | 2 | OCH$_3$ | H | H | H | — |
| 1.47 | | H | H | 1 | H | H | H | H | — |
| 1.48 | | H | H | 2 | H | H | CH$_3$ | H | — |
| 1.49 | | H | H | 1 | H | H | CH$_3$ | H | O |
| 1.50 | | H | H | 1 | H | H | CH$_2$CH$_3$ | H | — |
| 1.51 | rac | H | H | 1 | H | H | H | H | — |
| 1.52 | | H | H | 2 | H | H | CH$_3$ | H | — |
| 1.53 | | H | H | 1 | H | H | CH$_3$ | H | O |
| 1.54 | | H | H | 1 | H | H | H | H | — |
| 1.55 | rac | H | H | 1 | H | H | H | H | — |
| 1.56 | S | H | H | 1 | H | H | H | H | — |
| 1.57 | | H | H | 1 | H | H | CH$_2$CH$_3$ | H | — |
| 1.58 | S | H | H | 1 | H | H | CH$_3$ | H | — |
| 1.59 | | H | H | 2 | OCH$_3$ | H | H | H | — |
| 1.60 | | H | H | 2 | CH$_3$ | | | | |
| 1.61 | S | H | H | 1 | H | H | CH$_3$ | H | — |
| 1.62 | S | H | H | 1 | H | H | CH$_3$ | H | — |
| 1.63 | S | H | H | 1 | H | H | CH$_3$ | H | — |
| 1.64 | | H | H | 1 | H | H | CH$_3$ | H | — |
| 1.65 | S | H | H | 1 | H | H | CH$_3$ | H | — |
| 1.66 | S | H | H | 1 | H | H | CH$_3$ | H | — |
| 1.67 | | H | H | 1 | H | H | H | H | — |
| 1.68 | | H | H | 2 | OCH$_3$ | H | H | H | — |
| 1.69 | | H | H | 2 | H | H | H | H | — |
| 1.70 | | H | H | 2 | CH$_3$ | H | H | H | — |
| 1.71 | rac | H | H | 1 | H | H | H | H | — |
| 1.72 | S | H | H | 1 | H | H | CH$_3$ | H | — |
| 1.73 | S | H | H | 1 | H | H | CH$_3$ | H | — |
| 1.74 | S | H | H | 1 | H | H | CH$_3$ | H | — |
| 1.75 | S | H | H | 1 | H | H | CH$_3$ | H | — |
| 1.76 | S | H | H | 1 | H | H | CH$_3$ | H | — |
| 1.77 | S | H | H | 1 | H | H | CH$_3$ | H | — |
| 1.78 | S | H | H | 1 | H | H | CH$_3$ | H | — |
| 1.79 | S | H | H | 1 | H | H | CH$_3$ | H | — |
| 1.80 | S | H | H | 1 | H | H | CH$_3$ | H | — |
| 1.81 | | H | H | 2 | OCH$_3$ | H | H | H | — |
| 1.82 | | H | H | 2 | C(O)OCH$_3$ | H | H | H | — |
| 1.83 | | H | H | 2 | C(O)OCH$_3$ | H | H | H | — |
| 1.84 | | H | H | 2 | C(O)OCH$_3$ | H | H | H | — |
| 1.85 | S | H | H | 1 | H | H | CH$_3$ | H | — |
| 1.86 | S | H | H | 1 | H | H | CH$_3$ | H | — |
| 1.87 | S | H | H | 1 | H | H | CH$_3$ | H | — |
| 1.88 | S | H | H | 1 | H | H | CH$_3$ | H | — |
| 1.89 | | H | H | 1 | H | H | CH$_3$ | H | — |
| 1.90 | S | H | H | 1 | H | H | CH$_3$ | H | — |
| 1.91 | S | H | H | 1 | H | H | CH$_3$ | H | — |
| 1.92 | | H | H | 2 | H | H | CH$_3$ | H | — |
| 1.93 | | H | H | 2 | CH$_3$ | H | H | H | — |
| 1.94 | | H | H | 2 | CH$_3$ | H | H | H | — |
| 1.95 | | H | H | 2 | H | H | H | H | — |
| 1.96 | | H | H | 1 | H | H | CH$_2$CH$_3$ | H | — |
| 1.97 | S | H | H | 1 | H | H | CH$_3$ | H | — |
| 1.98 | S | H | H | 1 | H | H | CH$_3$ | H | — |
| 1.99 | S | H | H | 1 | H | H | CH$_3$ | H | — |
| 1.100 | | H | H | 2 | CH$_3$ | H | H | H | — |
| 1.101 | | H | H | 2 | F | H | H | H | — |
| 1.102 | | H | H | 2 | F | H | H | H | — |

TABLE 5-continued

| | | | | | | | | |
|---|---|---|---|---|---|---|---|---|
| 1.103 | H | H | 2 | F | H | H | H | — |
| 1.104 | H | H | 2 | F | H | H | H | — |
| 1.105 | H | H | 2 | Cl | H | H | H | — |
| 1.106 | H | H | 2 | Cl | H | H | H | — |
| 1.107 | H | H | 2 | Cl | H | H | H | — |
| 1.108 | H | H | 2 | Cl | H | H | H | — |
| 1.109 | H | H | 2 | $CH_3$ | H | $CH_3$ | H | — |
| 1.110 | H | H | 2 | $CH_3$ | H | $CH_3$ | H | — |
| 1.111 | H | H | 2 | $CH_3$ | H | $CH_3$ | H | — |
| 1.112 | H | H | 2 | $CH_3$ | H | $CH_3$ | H | — |
| 1.113 | H | H | 2 | F | H | $CH_3$ | H | — |
| 1.114 | H | H | 2 | F | H | $CH_3$ | H | — |
| 1.115 | H | H | 2 | F | H | $CH_3$ | H | — |
| 1.116 | H | H | 2 | F | H | $CH_3$ | H | — |
| 1.117 | H | H | 2 | Cl | H | $CH_3$ | H | — |
| 1.118 | H | H | 2 | Cl | H | $CH_3$ | H | — |
| 1.119 | H | H | 2 | Cl | H | $CH_3$ | H | — |
| 1.120 | H | H | 2 | Cl | H | $CH_3$ | H | — |

The present invention further provides processes for preparing corresponding compounds of the general formula (I) and/or salts thereof and/or agrochemically acceptable quaternized nitrogen derivatives thereof

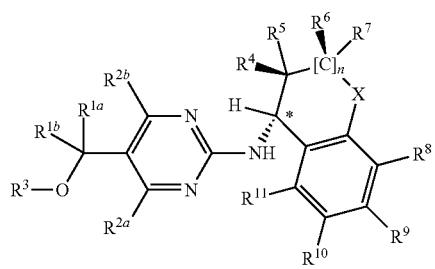

(I)

in which the radicals $R^{1a}$ to $R^{11}$ and also X and n have the above meanings, and where according to a first process (process (a))

a) a compound of the general formula (II)

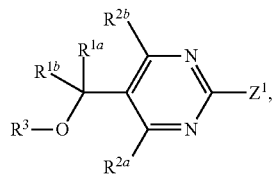

(II)

where $R^{1a}$, $R^{1b}$, $R^{2a}$, $R^{2b}$ and $R^3$ have the meaning given above and $Z^1$ represents an exchangeable radical or a leaving group, is reacted with an amine of the general formula (III) or an acid addition salt of the amine of the general formula (III)

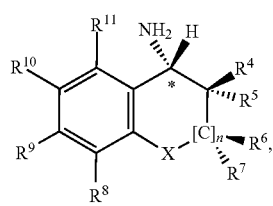

(III)

where the radicals $R^4$ to $R^{11}$, X and n have the above meaning.

The exchangeable radical $Z^1$ or the leaving group $Z^1$ represents fluorine, chlorine, bromine, iodine, a $(C_1-C_4)$-alkylsulfanyl or a $(C_1-C_4)$-alkylsulfinyl or a $(C_1-C_4)$-alkylsulfonyl, an unsubstituted phenyl-$(C_1-C_4)$-alkylsulfonyl or a phenyl-$(C_1-C_4)$-alkylsulfonyl which is mono- or polysubstituted by fluorine, chlorine, bromine or $(C_1-C_4)$-alkyl or $(C_1-C_4)$-alkoxy or represents a $(C_1-C_4)$-alkylphenylsulfonyl.

Particularly preferred exchangeable radicals $Z^1$ or leaving groups $Z^1$ are chlorine, methylsulfanyl, methylsulfinyl or methylsulfonyl.

If necessary, a $Z^1$ radical can be converted into another group of better exchangeability. For example, in the context of a two-stage one-pot method, $(C_1-C_4)$-alkylsulfanyl can be converted with an oxidizing agent such as m-chloroperbenzoic acid or Oxone® into $(C_1-C_4)$-alkylsulfinyl or $(C_1-C_4)$-alkylsulfonyl or mixtures thereof, and then reacted with an amine of the general formula (I) or an acid addition salt using an auxiliary base, for example triethylamine or potassium carbonate.

The reaction may optionally also be catalyzed by various auxiliaries, for example by the reagents potassium phosphate, copper(I) iodide and N,N-diethyl-2-hydroxybenzamides, or in the manner of the Buchwald-Hartwig coupling by special transition metal catalyst systems.

The compounds of the general formula (II) can be prepared by known processes, for example from the corresponding 5-ketopyrimidines. Thus, 5-ketopyrimidines of the general formula (IIa) described below of the [5-C(=O)—$R^{1b}$] type can be converted for example by reductive processes known from the literature into compounds of the formula (I) in which $R^{1a}$ and $R^3$ represent hydrogen. Preference is given to reduction with sodium tetrahydroborate. In addition, aldehydes or ketones of the general formula (IIb) described below, of the type [5-C(=O)—$R^{1a}$], can be converted, for example by reactions with carbon nucleophiles, into compounds of the formula (I). Such reactions of carbon nucleophiles at the C—O double bond, for example the aldol addition, the Grignard reaction or the Reformatzky reaction are well-known to the person skilled in the art from the literature.

The compounds of the general formula (II) can also be prepared, for example, from the corresponding 5-halopyrimidines, particularly preferably from the corresponding 5-bromopyrimidines or 5-iodopyrimidines, by known processes. Thus, the corresponding 5-halopyrimidines can be converted, for example, with ketones of the formula $R^{1a}C(O)R^{1b}$ and an organolithium compound, for example n-butyllithium, into compounds of the general formula (II) in which $R^3$ represents hydrogen.

If $R^3$ represents hydrogen, the hydrogen atom can be converted, for example by reactions of the alkylation or acylation type, into other molecules of the formula (II).

If $R^3$ represents hydrogen, the hydrogen atom can also be converted by reactions of the alkylation or acylation type into other molecules of the formula (I) only once the reaction with the amine of the general formula (III) has been carried out.

The amines of the general formula (III) or the acid addition salts thereof are commercially available, or the synthesis thereof is described in WO 2004/069814 A1.

In a further embodiment, the compounds of the general formula (I) and/or agrochemically acceptable salts thereof and/or agrochemically acceptable quaternized nitrogen derivatives thereof

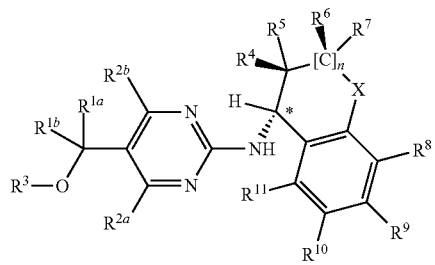

(I)

in which the radicals $R^{1a}$ to $R^{11}$ and also X and n have the above meanings, are prepared by a second process (b) in which initially
a compound of the general formula (IIa)

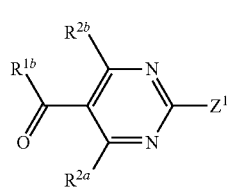

(IIa)

in which $R^{1b}$, $R^{2a}$ and $R^{2b}$ have the meaning given above and $Z^1$ represents an exchangeable radical or a leaving group,
is reacted with an amine of the general formula (III) or an acid addition salt of the amine of the general formula (III)

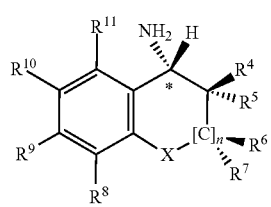

(III)

where the radicals $R^4$ to $R^{11}$, X and n have the above meaning, to give 2-amino-5-ketopyrimidine derivatives of the formula (Ia)

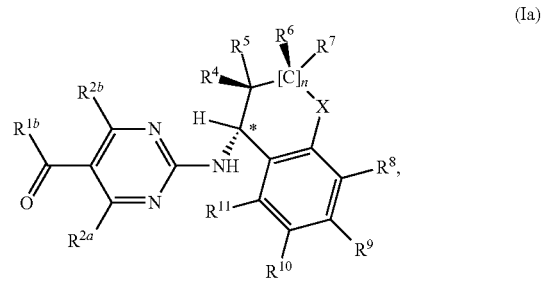

(Ia)

where the radicals $R^{1b}$ to $R^{11}$ and also X and n have the above meanings.

The exchangeable $Z^1$ radical or the leaving group $Z^1$ is fluorine, chlorine, bromine, iodine, a $(C_1-C_4)$-alkylsulfanyl or a $(C_1-C_4)$-alkylsulfinyl or a $(C_1-C_4)$-alkylsulfonyl, an unsubstituted or substituted phenyl-$(C_1-C_4)$-alkylsulfonyl or a $(C_1-C_4)$-alkylphenylsulfonyl.

Particularly preferred exchangeable radicals $Z^1$ or the leaving groups $Z^1$ are chlorine, methylsulfanyl, methylsulfinyl or methylsulfonyl.

If necessary, a $Z^1$ radical can be convened into another group of better exchangeability. For example, in the context of a two-stage one-pot method, $(C_1-C_4)$-alkylsulfanyl can be converted with an oxidizing agent such as m-chloroperbenzoic acid or Oxone® into $(C_1-C_4)$-alkylsulfinyl or $(C_1-C_4)$-alkylsulfonyl or mixtures thereof, and then reacted with an amine of the general formula (III) or an acid addition salt using an auxiliary base, for example triethylamine or potassium carbonate.

The reaction may optionally also be catalyzed by various auxiliaries, for example by the reagents potassium phosphate, copper(I) iodide and N,N-diethyl-2-hydroxybenzamides, or in the manner of the Buchwald-Hartwig coupling by special transition metal catalyst systems.

The compounds of the general formula (IIa) are commercially available or can be prepared by known processes, for example by processes described in document WO 2016/001118 A1.

The amines of the general formula (III) or the acid addition salt thereof are commercially available, or the synthesis thereof is described in WO 2004/069814 A1.

The 2-amino-5-ketopyrimidine derivatives of the formula (Ia) prepared in this way are then converted by reductive processes known from the literature into compounds of the formula (I) in which $R^{1a}$ and $R^3$ represents hydrogen. Preference is given to reduction with sodium tetrahydroborate.

In addition, the 2-amino-5-ketopyrimidine derivatives of the formula (Ia) prepared in this manner can be converted with carbon nucleophiles [of the type $(R^{1a})^-$] to give compounds of the formula (I) in which $R^3$ represents hydrogen. Such reactions suitable for introducing the radical $R^{1a}$, for example the aldol addition, the Grignard reaction (with $R^{1a}$MgHal) or the Reformatzky reaction are known to the person skilled in the art from the literature.

In the resulting compounds of the formula (I) in which $R^3$ represents hydrogen, the hydrogen atom ($R^3$=H) can be converted, for example, by reactions of the alkylation or acylation type into other molecules of the formula (I) where $R^3$ does not represent hydrogen.

Analogously to the processes described under b., it is alternatively also possible to employ aldehydes or ketones of the general formula (IIb) as starting materials for preparing compounds of the formula (I).

Here, aldehydes or ketones of the general formula (IIb)

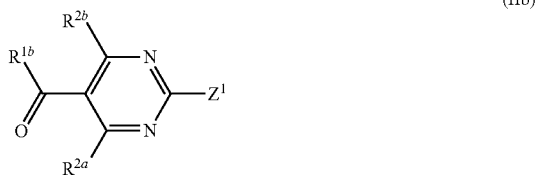

(IIb)

in which $R^{1a}$, $R^{2a}$ and $R^{2b}$ have the meaning given above and $Z^1$ represents an exchangeable radical or a leaving group, are reacted with an amine of the general formula (III) or an acid addition salt of the amine of the general formula (III)

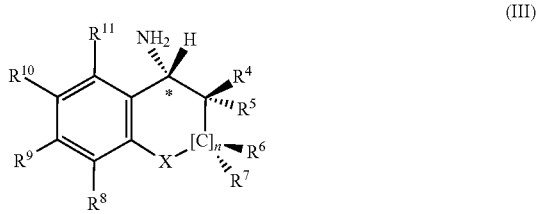

(III)

where the radicals $R^4$ to $R^{11}$, X and n have the above meaning, to give 2-amino-5-ketopyrimidine derivatives of the formula (Ib)

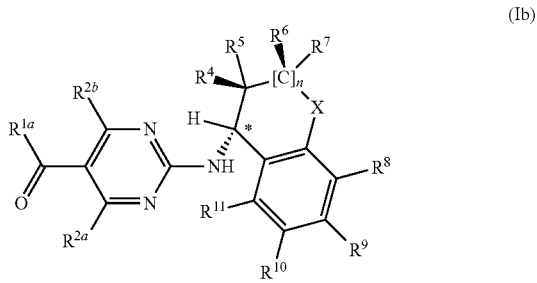

(Ib)

where the radicals $R^{1a}$ to $R^{11}$ and also X and n have the above meanings.

The exchangeable $Z^1$ radical or the leaving group $Z^1$ is fluorine, chlorine, bromine, iodine, a $(C_1-C_4)$-alkylsulfanyl or a $(C_1-C_4)$-alkylsulfinyl or a $(C_1-C_4)$-alkylsulfonyl, an unsubstituted or substituted phenyl-$(C_1-C_4)$-alkylsulfonyl or a $(C_1-C_4)$-alkylphenylsulfonyl.

Particularly preferred exchangeable radicals $Z^1$ or the leaving groups $Z^1$ are chlorine, methylsulfanyl, methylsulfinyl or methylsulfonyl.

If necessary, a $Z^1$ radical can be converted into another group of better exchangeability. For example, in the context of a two-stage one-pot method, $(C_1-C_4)$-alkylsulfanyl can be converted with an oxidizing agent such as m-chloroperbenzoic acid or Oxone® into $(C_1-C_4)$-alkylsulfinyl or $(C_1-C_4)$-alkylsulfonyl or mixtures thereof, and then reacted with an amine of the general formula (III) or an acid addition salt using an auxiliary base, for example triethylamine or potassium carbonate.

The reaction may optionally also be catalyzed by various auxiliaries, for example by the reagents potassium phosphate, copper(I) iodide and N,N-diethyl-2-hydroxybenzamides, or in the manner of the Buchwald-Hartwig coupling by special transition metal catalyst systems.

The compounds of the general formula (IIb) are commercially available or can be prepared by known processes, for example by processes described in document WO 2016/001118 A1.

The 2-amino-5-ketopyrimidine derivatives of the formula (Ib) prepared in this manner can then be converted by reactions known from the literature with carbon nucleophiles [of the type $(R^{1b})^-$] to give compounds of the formula (I) in which $R^3$ represents hydrogen. Such reactions, for example the aldol addition, the Grignard reaction (with $R^{1b}$MgHal) or the Reformatzky reaction are well-known to the person skilled in the art from the literature.

In the resulting compounds of the formula (I) in which $R^3$ represents hydrogen, the hydrogen atom (=$R^3$) can be converted, for example, by reactions of the alkylation or acylation type into other molecules of the formula (I) where $R^3$ does not represent hydrogen.

Alternatively, compounds of the general formula (I) can also be prepared by a third process (c) by initially converting a compound of the general formula (IIc)

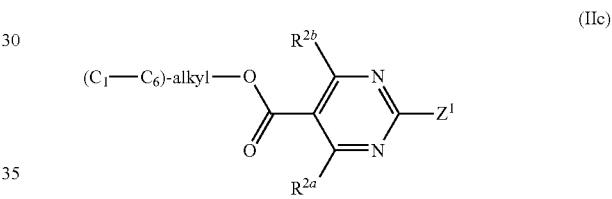

(IIc)

in which $R^{2a}$ and $R^{2b}$ have the meaning given above and $Z^1$ represents an exchangeable radical or a leaving group, analogously to the processes described under a, with an amine of the formula (III) or an acid addition salt of an amine of the formula (I) into an intermediate of the formula (Ic)

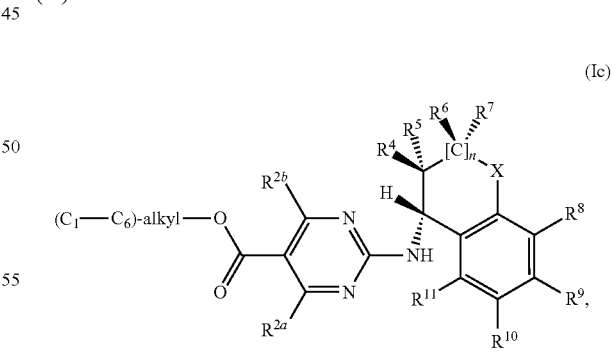

(Ic)

where the radicals $R^{2a}$ to $R^{11}$ and also X and n have the above meanings.

The resulting compounds of the general formula (Ic), in which $(C_1-C_6)$-alkyl is particularly preferably methyl or ethyl, can then be converted by processes described in the literature, particularly preferably by Grignard reaction, into compounds of the general formula (I) in which $R^{1a}$ and $R^{1b}$ have the same meaning. Thus, variant (c) represents an additional option for obtaining compounds of the formula (I) in which e.g. $R^{1a}$=CH$_3$ and $R^{1b}$=CH$_3$.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from Teledyne ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which in turn may be performed manually or in an automated manner.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

On account of the herbicidal property of the compounds of the general formula (I), the invention also further provides for the use of the compounds of the general formula (I) according to the invention as herbicides for control of harmful plants.

Herbicides are used in agriculturally utilized crops during various cultivation phases. Thus, the application of some products even takes place before or during sowing. Others are applied before the crop plant emerges, i.e. before the seedling breaks through the earth's surface (pre-emergence herbicides). Finally, post-emergence herbicides are used if either already the seed leaves or foliage leaves have been formed by the crop plant.

The compounds of the invention can be employed either pre-emergence or post-emergence, preference being given to pre-emergence use of the compounds of the invention.

The pre-emergence treatment includes both the treatment of the area under cultivation prior to sowing (ppi=pre plant incorporation) and the treatment of the sown areas of cultivation which do not yet sustain any growth.

The compounds of the formula (I) according to the invention and their salts, also referred to synonymously and collectively hereinafter as compounds of the formula (I), have excellent herbicidal efficacy against a broad spectrum of economically important monocotyledonous and dicotyledonous harmful plants. The active compounds also have good control over perennial weeds which are difficult to control and produce shoots from rhizomes, root stocks or other perennial organs. It does not matter here whether the substances are applied by the presowing method, the pre-emergence method or the post-emergence method.

Specific examples of some representatives of the monocotyledonous and dicotyledonous weed flora which can be controlled by the compounds of the general formula (I) according to the invention are mentioned hereinafter, without any intention that the enumeration is to impose a restriction to particular species.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual group and on the sides of the perennial species *Agropyron, Cynodon, Imperata* and Sorghum and also perennial *Cyperus* species are well controlled.

On the side of the dicotyledonous weed species, the activity spectrum extends, for example, to species such as *Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Anemisia* in the case of the perennial weeds. Moreover, herbicidal action is observed in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

If the compounds of the general formula (I) according to the invention are applied to the soil surface before germination, either the emergence of the weed seedlings is prevented completely or the weeds grow until they have reached the cotyledon stage, but then they stop growing and ultimately die completely after three to four weeks have passed.

If the active compounds of the general formula (I) are applied post-emergence to the green parts of the plants, growth likewise stops sharply very rapidly after the treatment, and the weed plants remain at the growth stage at the time of application or die completely after a certain time, such that competition by the weeds, which is harmful to the crop plants, is thus eliminated very early and in a lasting manner.

Although the compounds of the general formula (I) according to the invention have excellent herbicidal activity in respect of monocotyledonous and dicotyledonous weeds, crop plants of economically important crops, for example wheat, barley, rye, rice, corn, sugar beet, cotton, oilseed rape and soybean, are only damaged negligibly, if at all. This is why the present compounds are highly suitable for the selective control of unwanted plant growth in agriculturally useful plants.

In addition, the substances of the general formula (I) according to the invention have excellent growth regulatory properties in crop plants. They engage in the plant's own metabolism in a regulatory fashion and can therefore be employed for the influencing, in a targeted manner, of plant constituents and for facilitating harvesting, such as, for example, by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since this can reduce or completely prevent lodging.

The substances of the general formula (I) according to the invention can be employed in combination with further active compounds, plant growth regulators and/or safeners.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem 1, photosystem 11 or protoporphyrinogen oxidase, as are described in, for example, Weed Research 26 (1986) 441-445 or "The Pesticide Manual", 16th edition.

The British Crop Protection Council and the Royal Soc. of Chemistry, 2006 and the literature cited therein. Known herbicides or plant growth regulators which can be combined with the compounds according to the invention are, for example, the following active compounds, where said compounds are designated either with their "common name" in accordance with the International Organization for Standardization (ISO) or with the chemical name or with the code number. They always encompass all of the application forms such as, for example, acids, salts, esters and also all isomeric forms such as stereoisomers and optical isomers, even if not explicitly mentioned.

Examples of such herbicidal mixing partners are:

acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammonium sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfen- prop, chlorflurenol, chlorflurenol-methyl, chloridazon, chlorimuron, chlorimuron-ethyl, chlorophthalim, chlorotoluron, chlorthal-dimethyl, chlorsulfuron, 3-[5-chloro-4-(trifluoromethyl)pyridin-2-yl]-4-hydroxy-1-methylimidazolidin-2-one, cinidin, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamine, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat dibromide, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, florpyrauxifen, florpyrauxifen-benzyl, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, 4-hydroxy-1-methoxy-5-methyl-3-[4-(trifluoromethyl)pyridin-2-yl]imidazolidin-2-one, 4-hydroxy-1-methyl-3-[4-(trifluoromethyl)pyridin-2-yl]imidazolidin-2-one, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e.

3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium and -butotyl, mecoprop-P, mecoprop-P-butotyl, -dimethylammoniumn, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxotrione (lancotrione), oxyfluorfen, paraquat, paraquat dichloride, pebulate, pendimethalin, penoxsulam, pentachlorohenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrione, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazine, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline and the compounds below:

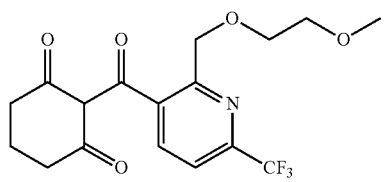

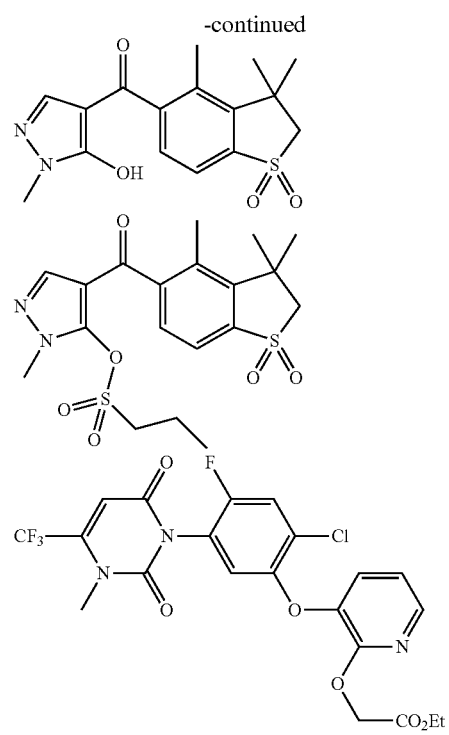

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenoxide mixture, 4-oxo-4[(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

The safeners are preferably selected from the group consisting of:

S1) Compounds of the formula (S1)

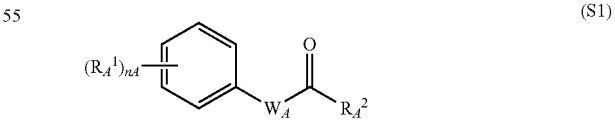

where the symbols and indices are defined as follows:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of ($W_A^1$) to ($W_A^4$),

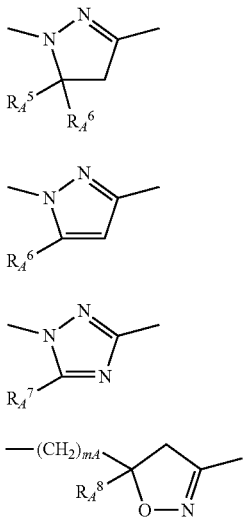

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of ($C_1$-$C_4$)-alkyl, ($C_1$-$C_4$)-alkoxy or optionally substituted phenyl, preferably a radical of the formula $OR_A^3$, $NHR_A^4$ or $N(CH_3)_2$, especially of the formula $OR_A^3$, $R_A^3$ is hydrogen or an unsubstituted or substituted aliphatic hydrocarbon radical preferably having a total of 1 to 18 carbon atoms;

$R_A^4$ is hydrogen, ($C_1$-$C_6$)-alkyl, ($C_1$-$C_6$)-alkoxy or substituted or unsubstituted phenyl;

$R_A^5$ is H, ($C_1$-$C_8$)-alkyl, ($C_1$-$C_8$)-haloalkyl, ($C_1$-$C_4$)-alkoxy-($C_1$-$C_8$)-alkyl, cyano or $COOR_A^9$, where $R_A^9$ is hydrogen, ($C_1$-$C_8$)-alkyl, ($C_1$-$C_8$)-haloalkyl, ($C_1$-$C_4$)-alkoxy-($C_1$-$C_4$)-alkyl, ($C_1$-$C_6$)-hydroxyalkyl, ($C_3$-$C_{12}$)-cycloalkyl or tri-($C_1$-$C_4$)-alkylsilyl;

$R_A^6$, $R_A^7$, $R_A^8$ are identical or different and are each hydrogen, ($C_1$-$C_8$)-alkyl, ($C_1$-$C_8$)-haloalkyl, ($C_3$-$C_2$)-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

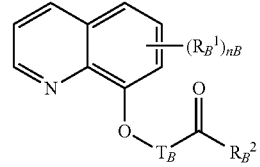

where the symbols and indices have the meanings below:

$R_B^1$ is halogen, ($C_1$-$C_4$)-alkyl, ($C_1$-$C_4$)-alkoxy, nitro or ($C_1$-$C_4$)-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of ($C_1$-$C_4$)-alkyl, ($C_1$-$C_4$)-alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbon radical preferably having a total of 1 to 18 carbon atoms;

$R_B^4$ is hydrogen, ($C_1$-$C_6$)-alkyl, ($C_1$-$C_6$)-alkoxy or substituted or unsubstituted phenyl;

$T_B$ is a ($C_1$ or $C_2$)-alkanediyl chain which is unsubstituted or substituted by one or two ($C_1$-$C_4$)-alkyl radicals or by [($C_1$-$C_3$)-alkoxy]carbonyl;

preferably:

a) compounds of the 8-quinolinoxyacetic acid type (S2$^a$), preferably
   1-methylhexyl (5-chloro-8-quinolinoxy)acetate ("cloquintocet-mexyl") (S2-1),
   (1,3-dimethylbut-1-yl) (5-chloro-8-quinolinoxy)acetate (S2-2),
   4-allyloxybutyl (5-chloro-8-quinolinoxy)acetate (S2-3),
   1-allyloxyprop-2-yl (5-chloro-8-quinolinoxy)acetate (S2-4), ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-O 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-O 582 198.

S3) Compounds of the formula (S3)

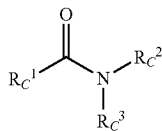

(S3)

where the symbols and indices are defined as follows:

$R_C^1$ is $(C_1$-$C_4)$-alkyl, $(C_1$-$C_4)$-haloalkyl, $(C_2$-$C_4)$-alkenyl, $(C_2$-$C_4)$-haloalkenyl, $(C_3$-$C_7)$-cycloalkyl, preferably dichloromethyl;

$R_C^2$, $R_C^3$ are identical or different and are hydrogen, $(C_1$-$C_4)$-alkyl, $(C_2$-$C_4)$-alkenyl, $(C_2$-$C_4)$-alkynyl, $(C_1$-$C_4)$-haloalkyl, $(C_2$-$C_4)$-haloalkenyl, $(C_1$-$C_4)$-alkylcarbamoyl-$(C_1$-$C_4)$-alkyl, $(C_2$-$C_4)$-alkenylcarbamoyl-$(C_1$-$C_4)$-alkyl, $(C_1$-$C_4)$-alkoxy-$(C_1$-$C_4)$-alkyl, dioxolanyl-$(C_1$-$C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9)

((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-acylsulfonamides of the formula (S4) and salts thereof,

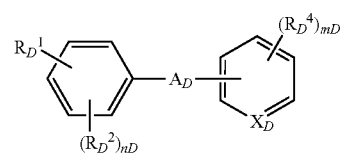

(S4)

in which the symbols and indices are defined as follows:

$A_D$ is $SO_2$—$NR_D^3$—CO or CO—$NR_D^3$—$SO_2$ $X_D$ is CH or N;

$R_D^1$ is CO—$NR_D^5R_D^6$ or NHCO—$R_D^7$;

$R_D^2$ is halogen, $(C_1$-$C_4)$-haloalkyl, $(C_1$-$C_4)$-haloalkoxy, nitro, $(C_1$-$C_4)$-alkyl, $(C_1$-$C_4)$-alkoxy, $(C_1$-$C_4)$-alkylsulfonyl, $(C_1$-$C_4)$-alkoxycarbonyl or $(C_1$-$C_4)$-alkylcarbonyl;

$R_D^3$ is hydrogen, $(C_1$-$C_4)$-alkyl, $(C_2$-$C_4)$-alkenyl or $(C_2$-$C_4)$-alkynyl;

$R_D^4$ is halogen, nitro, $(C_1$-$C_4)$-alkyl, $(C_1$-$C_4)$-haloalkyl, $(C_1$-$C_4)$-haloalkoxy, $(C_3$-$C_6)$-cycloalkyl, phenyl, $(C_1$-$C_4)$-alkoxy, cyano, $(C_1$-$C_4)$-alkylthio, $(C_1$-$C_4)$-alkylsulfinyl, $(C_1$-$C_4)$-alkylsulfonyl, $(C_1$-$C_4)$-alkoxycarbonyl or $(C_1$-$C_4)$-alkylcarbonyl;

$R_D^5$ is hydrogen, $(C_1$-$C_6)$-alkyl, $(C_3$-$C_6)$-cycloalkyl, $(C_2$-$C_6)$-alkenyl, $(C_2$-$C_6)$-alkynyl, $(C_5$-$C_6)$-cycloalkenyl, phenyl or 3- to 6-membered heterocyclyl containing $v_D$ heteroatoms from the group consisting of nitrogen, oxygen and sulfur, where the seven last-mentioned radicals are substituted by $v_D$ substituents from the group consisting of halogen, $(C_1$-$C_6)$-alkoxy, $(C_1$-$C_6)$-haloalkoxy, $(C_1$-$C_2)$-alkylsulfinyl, $(C_1$-$C_2)$-alkylsulfonyl, $(C_3$-$C_6)$-cycloalkyl, $(C_1$-$C_4)$-alkoxycarbonyl, $(C_1$-$C_4)$-alkylcarbonyl and phenyl and, in the case of cyclic radicals, also $(C_1$-$C_4)$-alkyl and $(C_1$-$C_4)$-haloalkyl;

$R_D^6$ is hydrogen, $(C_1$-$C_6)$-alkyl, $(C_2$-$C_6)$-alkenyl or $(C_2$-$C_6)$-alkynyl, where the three last-mentioned radicals are substituted by $v_D$ radicals from the group consisting of halogen, hydroxy, $(C_1$-$C_4)$-alkyl, $(C_1$-$C_4)$-alkoxy and $(C_1$-$C_4)$-alkylthio, or $R_D^5$ and $R_D^6$ together with the nitrogen atom carrying them form a pyrrolidinyl or piperidinyl radical;

$R_D^7$ is hydrogen, $(C_1$-$C_4)$-alkylamino, di-$(C_1$-$C_4)$-alkylamino, $(C_1$-$C_6)$-alkyl, $(C_3$-$C_6)$-cycloalkyl, where the 2 last-mentioned radicals are substituted by $v_D$ substituents from the group consisting of halogen, $(C_1$-$C_4)$-alkoxy, $(C_1$-$C_6)$-haloalkoxy and $(C_1$-$C_4)$-alkylthio and, in the case of cyclic radicals, also $(C_1$-$C_4)$-alkyl and $(C_1$-$C_4)$-haloalkyl $n_D$ is 0, 1 or 2;

$m_D$ is 1 or 2;

$v_D$ is 0, 1, 2 or 3;

among these, preference is given to compounds of the N-acylsulfonamide type, for example of the formula (S4$^3$) below, which are known, for example, from WO-A-97/45016

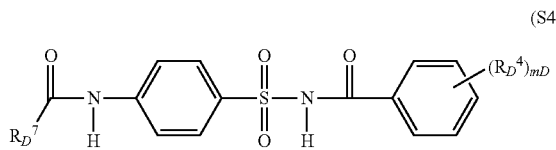

in which
$R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$;
$m_D$ is 1 or 2;
$v_D$ is 0, 1, 2 or 3;
and
acylsulfamoylbenzamides, for example of the formula (S4$^b$) below, which are known, for example, from WO-A-99/16744,

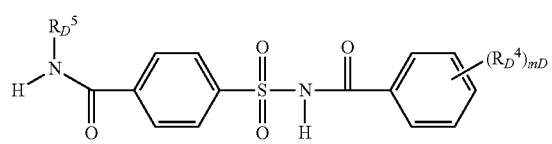

for example those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and
compounds of the N-acylsulfamoylphenylurea type, of the formula (S4$^c$), which are known, for example, from EP-A-365484,

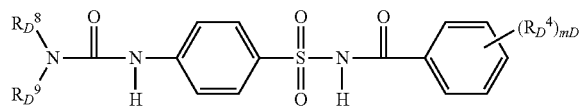

in which
$R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl,
$R_D^4$ is halogen, $(C_1-C_4)$-alkyl, $(C_1-C_4)$-alkoxy, $CF_3$
$m_D$ is 1 or 2;
for example
1-[4-(N-2-methoxybenzoylsulfamoyl)phenyl]-3-methylurea ("metcamifen", S4-6),
1-[4-(N-2-methoxybenzoylsulfamoyl)phenyl]-3,3-dimethylurea,
1-[4-(N-4,5-dimethylbenzoylsulfamoyl)phenyl]-3-methylurea,
and
N-phenylsulfonylterephthalamides of the formula (S4$^d$), which are known, for example, from CN 101838227,

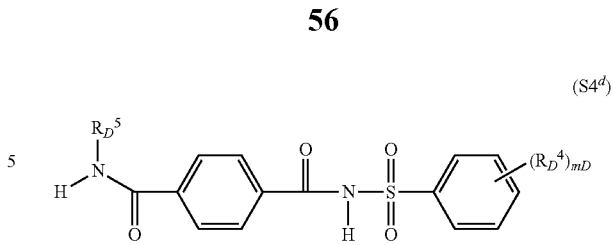

for example those in which
$R_D^4$ is halogen, $(C_1-C_4)$-alkyl, $(C_1-C_4)$-alkoxy, $CF_3$;
$m_D$ is 1 or 2;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, or $(C_5-C_6)$-cycloalkenyl.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example
1-methyl-3-(2-thienyl)-1,2-dihydroquinoxalin-2-one,
1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

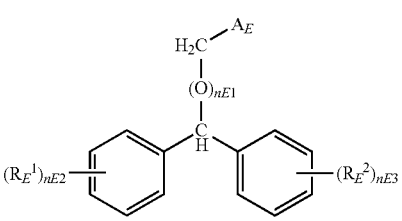

in which the symbols and indices are defined as follows:
$R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ are each independently of one another hydrogen, $(C_1-C_4)$-alkyl, $(C_2-C_6)$-alkenyl, $(C_2-C_6)$-alkynyl, cyanoalkyl, $(C_1-C_4)$-haloalkyl, phenyl, nitrophenyl, benzyl, halobenzyl, pyridinylalkyl and alkylammonium,
$n_E^1$ is 0 or 1
$n_E^2$, $n_E^3$ are each independently 0, 1 or 2,
preferably:
diphenylmethoxyacetic acid,
ethyl diphenylmethoxyacetate,
methyl diphenylmethoxyacetate (CAS reg. no. 41858-19-9) (S7-1).

S8) Compounds of the formula (S8), as described in WO-A-98/27049,

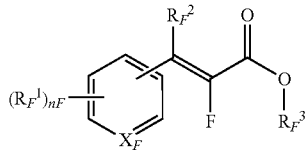

in which
X$_F$ is CH or N,
n$_F$ in the case that X$_F$=N is an integer from 0 to 4 and in the case that X$_F$=CH is an integer from 0 to 5,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy, nitro, (C$_1$-C$_4$)-alkylthio, (C$_1$-C$_4$)-alkylsulfonyl, (C$_1$-C$_4$)-alkoxycarbonyl, optionally substituted phenyl, optionally substituted phenoxy,
R$_F^2$ is hydrogen or (C$_1$-C$_4$)-alkyl,
R$_F^3$ is hydrogen, (C$_1$-C$_8$)-alkyl, (C$_2$-C$_4$)-alkenyl, (C$_2$-C$_4$)-alkynyl or a yl, where each of the carbon-containing radicals mentioned above is unsubstituted or substituted by one or more, preferably up to three, identical or different radicals from the group consisting of halogen and alkoxy, or salts thereof,
preferably compounds in which
X$_F$ is CH,
n$_F$ is an integer from 0 to 2,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy,
R$_F^2$ is hydrogen or (C$_1$-C$_4$)-alkyl,
R$_F^3$ is hydrogen, (C$_1$-C$_8$)-alkyl, (C$_2$-C$_4$)-alkenyl, (C$_2$-C$_4$)-alkynyl, or aryl, where each of the aforementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolyl-carbonyl)-2-quinolones (S9), for example
1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formula (S10$^a$) or (S10$^b$)
as described in WO-A-2007/023719 and WO-A-2007/023764

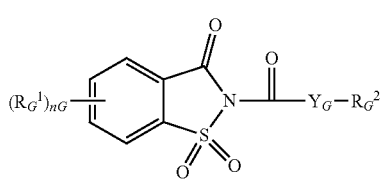

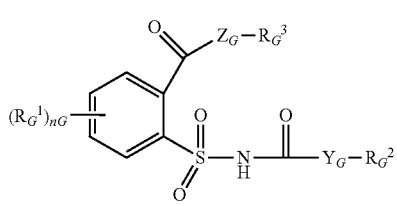

in which
R$_G^1$ is halogen, (C$_1$-C$_4$)-alkyl, methoxy, nitro, cyano, CF$_3$, OCF$_3$,
Y$_G$, Z$_G$ are each independently O or S,
n$_G$ is an integer from 0 to 4,
R$_G^2$ is (C$_1$-C$_{16}$)-alkyl, (C$_2$-C$_6$)-alkenyl, (C$_3$-C$_6$)-cycloalkyl, aryl; benzyl, halobenzyl,
R$_G^3$ is hydrogen or (C$_1$-C$_6$)-alkyl.

S11) Active compounds of the oxyimino compound type (S11), which are known as seed-dressing agents, for example
"oxabetrinil" ((Z)-1,3-dioxolan-2-ylmethoxyimino(phenyl)acetonitrile) (S11-1), which is known as a seed-dressing safener for millet/sorghum against metolachlor damage,
"fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and
"cyometrinil" or "CGA-43089" ((Z)-cyanomethoxyimino (phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as a seed-dressing safener for maize against thiocarbamate herbicide damage,
"fenclorim" (4,6-dichloro-2-phenylpyrimidine) (S13-2), which is known as a safener for pretilachlor in sown rice,
"flurazole" (benzyl 2-chloro-4-trifluoromethyl-1,3-thiazole-5-carboxylate) (S13-3), which is known as a seed-dressing safener for millet/sorghum against alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as a safener for maize against damage by imidazolinones,
"MG 191" (CAS Reg. No. 96420-72-3) (2-dichloromethyl-2-methyl-1,3-dioxolane) (S13-5) from Nitrokemia, which is known as a safener for maize,
"MG 838" (CAS Reg. No. 133993-74-5) (2-propenyl 1-oxa-4-azaspiro[4.5]decane-4-carbodithioate) (S13-6) from Nitrokemia,
"disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).

S14) Active compounds which, in addition to herbicidal action against harmful plants, also have safener action on crop plants such as rice, for example
"dimepiperate" or "MY 93" (S-1-methyl 1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as safener for rice against imazosulfuron herbicide damage,
"cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

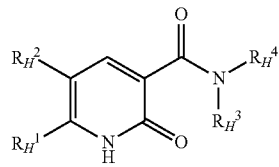

(S15)

as described in WO-A-2008/131861 and WO-A-2008/131860 in which $R_H^1$ is a $(C_1-C_6)$-haloalkyl radical and $R_H^2$ is hydrogen or halogen and $R_H^3$, $R_H^4$ are each independently of one another hydrogen, $(C_1-C_{16})$-alkyl, $(C_2-C_{16})$-alkenyl or $(C_2-C_{16})$-alkynyl, where each of the 3 latter radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring, where each of the 4 last-mentioned radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Preferred safeners are: cloquintocet-mexyl, cyprosulfamide, fenchlorazole-ethyl, isoxadifen-ethyl, mefenpyr-diethyl, fenclorim, cumyluron, S4-1 and 54-5, mecamifen, and particularly preferred safeners are: cloquintocet-mexyl, cyprosulfamide, isoxadifen-ethyl, mefenpyr-diethyl and metcamifen.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material. Other particular properties may be tolerance or resistance to abiotic stressors, for example heat, low temperatures, drought, salinity and ultraviolet radiation.

It is preferable to employ the compounds of the general formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferable to employ the compounds of the general formula (I) as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants.

Alternatively, novel plants with altered properties can be generated with the aid of recombinant methods (see, for example, EP 0221044, EP 0131624). For example, there have been descriptions in several cases of:

genetic modifications of crop plants for the purpose of modifying the starch synthesized in the plants (for example WO 92/011376, WO 92/014827, WO 91/019806), transgenic crop plants which are resistant to certain herbicides of the glufosinate type (cf., for example, EP 0242236, EP 0242246) or the glyphosate type (WO 92/000377) or the sulfonylurea type (EP 0257993, U.S. Pat. No. 5,013,659), transgenic crop plants, for example cotton, which is capable of producing Bacillus thuringiensis toxins (Bt toxins), which make the plants resistant to certain pests (EP 0142924, EP 0193259), transgenic crop plants having a modified fatty acid composition (WO 91/013972), genetically modified crop plants with novel constituents or secondary metabolites, for example novel phytoalexins, which bring about an increased disease resistance (EP 0309862, EP 0464461), genetically modified plants having reduced photorespiration, which have higher yields and higher stress tolerance (EP 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition Cold Spring Harbor Laboratory Press, Cold Spring Harbor, N.Y.; or Winnacker "Gene und Klone" [Genes and clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferable to use the compounds of the general formula (I) according to the invention in transgenic crops which are resistant to growth regulators, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active compounds.

When the active compounds of the general formula (I) according to the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the general formula (I) according to the invention as herbicides for control of harmful plants in transgenic crop plants.

The compounds of the general formula (I) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964, Schönfeldt, "Grenzflächenaktive Äthylenoxidaddukte [Interface-active ethylene oxide adducts]", Wiss. Verlagsgesell, Stuttgart 1976, Winnacker-Küchler, "Chemische Technologie [Chemical Technology]", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They can be produced, for example, by wet grinding by means of standard commercial bead mills and optionally the addition of surfactants, as have already been listed above, for example, for the other types of formulation.

Emulsions, for example oil-in-water emulsions (EW), can be produced, for example, by means of stirring, colloid mills and/or static mixers using aqueous organic solvents and optionally surfactants as already listed above, for example, for the other formulation types.

Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London; J. E. Browning, "Agglomeration", Chemical and Engineering 1967, pages 147 ff; "Perry's Chemical Engineer's Handbook", 5th Ed., McGraw Hill, N.Y. 1973, p. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1% to 99% by weight, especially 0.1% to 95% by weight of active compound of the formula (I).

In wettable powders, the active compound concentration is, for example, about 10% to 90% by weight, the remainder to 100% by weight consisting of customary formulation components. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

The compounds of the general formula (I) or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of tank mixes.

For application, the formulations in the commercial form are diluted if appropriate in a customary manner, for example with water in the case of wettable powders, emulsifiable concentrates, dispersions and water-dispersible granules. Dust-type preparations, granules for soil application or granules for scattering and sprayable solutions are not normally diluted further with other inert substances prior to application.

The required application rate of the compounds of the formula (I) and their salts varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha, more preferably in the range of from 0.01 to 1.5 kg/ha, particularly preferably in the range from 0.05 to 1 kg/ha g/ha. This applies both to the pre-emergence and the post-emergence application.

The present invention is illustrated in detail by the examples which follow, but these examples do not restrict the invention in any way.

A. Synthesis Examples 1-(2-{[(1R,2S)-2,6-Dimethyl-2,3-dihydro-1H-inden-1-yl]amino}-4-methylpyrimidin-5-yl)ethanol (Ex. 1.7)

1. At 0° C., 1.946 g (8.231 mmol) of meta-chloroperbenzoic acid dissolved in 40 ml of trichloromethane were added dropwise to a solution of 0.750 g (4.115 mmol) of 1-[4-methyl-2-(methylsulfanyl)pyrimidin-5-yl]ethanone in 35 ml of trichloromethane. The mixture was stirred at 20° C. for 1 h, and 2.290 g (22.634 mmol) of triethylamine and 0.730 g (4.527 mmol) of (1R,2S)-2,6-dimethylindan-1-amine dissolved in 10 ml of trichloromethane were added in succession. The mixture was stirred at 50° C. for 1.5 h, water and dichloromethane were added and the aqueous phase was extracted twice with dichloromethane. The combined organic phases were dried over sodium sulfate, the solvent was then removed under reduced pressure and the residue was taken up in acetonitrile. The insoluble residue (3-chlorobenzoic acid) was filtered off and the solvent was then removed under reduced pressure, giving, after purification of the residue by chromatography [start: ethyl acetate/n-heptane (5:95), over 25 min to ethyl acetate/n-heptane (30:70)], 0.853 g (70%) of 1-(2-{[(1R,2S)-2,6-dimethyl-2,3-dihydro-1H-inden-1-yl]amino}4-methylpyrimidin-5-yl)ethanone.

2. A little at a time, 0.327 g (8.633 mmol) of sodium tetrahydroborate was added to a solution of 0.850 g (2.878 mmol) of 1-(2-{[(1R,2S)-2,6-dimethyl-2,3-dihydro-1H-inden-1-yl]amino}-4-methylpyrimidin-5-yl)ethanone in 10 ml of ethanol, and the mixture was stirred at 0° C. for 2 h. The reaction mixture was acidified with 2 M hydrochloric acid and the solvent was removed under reduced pressure. Dichloromethane and water were added to the residue, aqueous sodium carbonate solution was added, the mixture was stirred at 20° C. for 5 min and the aqueous phase was extracted twice with dichloromethane. The combined organic phases were dried over sodium sulfate and the solvent was then removed under reduced pressure, giving, after purification of the residue by chromatography [start: ethyl acetate/n-heptane (5:95), over 15 min to ethyl acetate/n-heptane (35:65)], 0.715 g (84%) of 1-(2-{[(1R,2S)-2,6-dimethyl-2,3-dihydro-1H-inden-1-yl]amino}-4-methylpyrimidin-5-yl)ethanol (Ex. 1.7)

2-{2-[(1R)-1,2,3,4-Tetrahydronaphthalen-1-ylamino]pyrimidin-5-yl}propan-2-ol (Ex. 1.8)

1. At 0° C., 4.309 g (24.969 mmol) of meta-chloroperbenzoic acid dissolved in 35 ml of trichloromethane were added dropwise to a solution of 2.200 g (11.097 mmol) of ethyl 2-(methylsulfanyl)pyrimidine-5-carboxylate in 30 ml of trichloromethane. The mixture was stirred at 0-5° C. for 0.5 h, and 11.474 g (88.779 mmol) of N,N-diisopropylethylamine and 1.634 g (11.097 mmol) of (1R)-1,2,3,4-tetrahydronaphthalene-1-amine dissolved in 10 ml trichloromethane were added in succession. The mixture was stirred at 40° C. for 4 h, water and dichloromethane were added and the aqueous phase was extracted twice with dichloromethane. The combined organic phases were dried over sodium sulfate, the solvent was then removed under reduced pressure and the residue was taken up in acetonitrile. The insoluble residue (3-chlorobenzoic acid) was filtered off and the solvent was then removed under reduced pressure, giving 2.763 g (84%) of ethyl 2-[(1R)-1,2,3,4-tetrahydronaphthalen-1-ylamino]pyrimidine-5-carboxylate which was reacted further without further purification.

2. At 0° C. 2.396 ml (4.792 mmol) of methylmagnesium bromide (2 molar solution in 2-methyltetrahydrofuran) were added to a solution of 0.500 g (1.682 mmol) of ethyl 2-[(1R)-1,2,3,4-tetrahydronaphthalen-1-ylamino]pyrimidine-5-carboxylate in 7.5 ml of dry tetrahydrofuran, and the mixture was stirred at 55° C. under an atmosphere of nitrogen for 5 h. The reaction mixture was cooled to 0° C., about 30 ml of a solvent mixture of THF/water (4:1) were added dropwise and the mixture was extracted three times with ethyl acetate. The combined organic phases were dried over sodium sulfate and the solvent was then distilled off under reduced pressure, giving, after purification of the residue by chromatography [start: ethyl acetate/n-heptane (5:95), over 25 min to ethyl acetate/n-heptane (65:35)], 0.122 g (26%) of 2-{2-[(1R)-1,2,3,4-tetrahydronaphthalen-1-ylamino]pyrimidin-5-yl}propan-2-ol (Ex. 1.8)

2-(2-{[(1R,2S)-2,6-Dimethyl-2,3-dihydro-1H-inden-1-yl]amino}pyrimidin-5-yl)but-3-en-2-ol (Ex. 1.15)

1. In a microwave oven, a mixture of 1.000 g (6.387 mmol) of 1-(2-chloropyrimidin-5-yl)ethanone, 1.236 g (7.664 mmol) of (1R,2S)-2,6-dimethylindane-1-amine and 2.476 g (19.161 mmol) of N,N-diisopropylethylamine in 8.0 ml of 1,4-dioxane was heated at 140° C. for 45 min. After removal of the solvent under reduced pressure, water and dichloromethane were added to the mixture and the aqueous phase was extracted twice with dichloromethane. The combined organic phases were dried over sodium sulfate and the solvent was then distilled off under reduced pressure, giving, after purification of the residue by chromatography [start: ethyl acetate/n-heptane (5:95), over 25 min to ethyl acetate/n-heptane (50:50)], 1.630 g (85%) of 1-(2-{[(1R,2S)-2,6-dimethyl-2,3-dihydro-1H-inden-1-yl]amino}pyrimidin-5-yl)ethanone.

2. At 0° C., 0.260 g (0.924 mmol) of 1-(2-{[(1R,2S)-2,6-dimethyl-2,3-dihydro-1H-inden-1-yl]amino}pyrimidin-5-yl)ethanone in 4.5 ml of dry tetrahydrofuran was added to a solution of 1.617 ml (1.617 mmol) of bromo(vinyl)magnesium (1 molar solution in tetrahydrofuran), and the mixture was stirred at 20° C. under an atmosphere of nitrogen for 1.5 h. Saturated aqueous ammonium chloride solution was added dropwise to the mixture and the aqueous phase was then extracted three times with ethyl acetate. The combined organic phases were dried over sodium sulfate and the solvent was then distilled off under reduced pressure, giving, after purification of the residue by chromatography [start: ethyl acetate/n-heptane (5:95), over 30 min to ethyl acetate/n-heptane (50:50)], 0.066 g (23%) of 2-(2-{(1R,2S)-2,6-dimethyl-2,3-dihydro-1H-inden-1-ylamino}pyrimidin-5-yl)but-3-en-2-ol (Ex. 1.15).

NMR Data of Selected Examples

NMR Peak List Method

The 1H-NMR data of selected examples are noted in the form of 1H-NMR peak lists. For each signal peak, first the δ value in ppm and then the signal intensity in round brackets is listed. The δ value-signal intensity number pairs for different signal peaks are listed with separation from one another by semicolons.

The peak list for one example therefore takes the form of: $\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

1.2: $^1$H-NMR(400.0 MHz, CDCl3):
δ = 8.3259 (7.5); 8.0913 (0.8); 7.2590 (38.3); 7.0974 (1.9); 7.0785 (2.9); 7.0259 (7.1); 7.0071 (1.5); 5.4527 (0.9); 5.4308 (1.0); 5.2635 (1.3); 5.2415 (2.2); 5.2193 (1.0); 4.8503 (0.9); 4.8342 (2.8); 4.8180 (2.8); 4.8018 (0.9); 4.1470 (0.9); 4.1291 (2.8); 4.1113 (2.8); 4.0934 (0.9); 3.0769 (1.2); 3.0576 (1.3); 3.0383 (1.4); 3.0191 (1.5); 2.5584 (1.0); 2.5351 (1.2); 2.5198 (0.9); 2.4968 (1.1); 2.3328 (0.8); 2.3183 (0.9); 2.2893 (16.0); 2.2612 (1.0); 2.2387 (0.6); 2.0419 (12.4); 1.5489 (11.7); 1.5327 (11.5); 1.2872 (10.7); 1.2753 (4.8); 1.2704 (10.5); 1.2575 (7.1); 1.2396 (3.4); 0.0079 (0.6); −0.0002 (15.5); −0.0084 (0.6)
1.3: $^1$H-NMR(400.0 MHz, CDCl3):
δ = 8.2899 (10.0); 7.5168 (0.6); 7.3084 (3.1); 7.2947 (3.7); 7.2876 (4.2); 7.2795 (2.3); 7.2740 (4.0); 7.2580 (99.0); 7.1056 (2.5); 7.0869 (4.1); 7.0501 (7.3); 7.0343 (4.6); 7.0287 (8.3); 7.0122 (2.7); 7.0069 (3.6); 6.9940 (0.8); 5.3378 (0.8); 5.3161 (1.2); 5.2713 (1.8); 5.2504 (2.4); 5.2284 (1.0); 4.4600 (1.3); 4.4552 (1.3); 4.4308 (2.4); 4.4264 (2.4); 4.4118 (1.1); 4.3957 (3.3); 4.3794 (3.4); 4.3612 (3.8); 4.3312 (1.9); 3.0883 (1.4); 3.0691 (1.5); 3.0495 (1.6); 3.0305 (1.6); 2.5667 (1.1); 2.5441 (1.4); 2.5273 (1.0); 2.5051 (1.2); 2.3298 (0.8); 2.2973 (16.0); 2.2733 (1.2); 2.2536 (0.6); 1.5292 (10.6); 1.5277 (10.6); 1.5129 (10.5); 1.5114 (10.3); 1.3039 (8.9); 1.2984 (9.2); 1.2871 (8.8); 1.2816 (8.8); 1.2584 (1.0); 1.2470 (0.5); 0.0080 (1.3); −0.0002 (40.0); −0.0084 (1.4)
1.4: $^1$H-NMR(400.0 MHz, CDCl3):
δ = 8.4064 (5.1); 7.2606 (6.4); 7.0995 (1.8); 7.0807 (3.0); 7.0363 (3.7); 7.0262 (2.6); 7.0073 (1.4); 5.4388 (1.0); 5.4161 (1.2); 5.2591 (1.3); 5.2372 (2.1); 5.2151 (1.0); 3.0742 (1.2); 3.0551 (1.2); 3.0358 (1.4); 3.0167 (3.4); 2.5577 (0.9); 2.5347 (1.1); 2.5196 (0.8); 2.4965 (1.0); 2.3121 (0.6); 2.2902 (16.0); 2.2726 (1.2); 2.2552 (0.8); 1.7440 (1.1); 1.5875 (54.2); 1.2885 (12.2); 1.2717 (11.8); −0.0002 (1.8)
1.5: $^1$H-NMR(400.0 MHz, CDCl3):
δ = 8.4426 (2.2); 7.2594 (24.2); 7.1537 (0.7); 7.1483 (0.8); 7.1379 (0.7); 7.0637 (0.5); 2.3232 (3.7); 1.6676 (1.6); 1.5934 (16.0); 1.5707 (0.8); −0.0002 (9.0)
1.6: $^1$H-NMR(400.0 MHz, CDCl3):
δ = 8.2917 (1.5); 7.2593 (25.4); 7.0903 (0.8); 7.0713 (1.3); 7.0408 (1.5); 7.0174 (1.0); 6.9953 (0.7); 5.2488 (0.6); 3.0664 (0.5); 3.0473 (0.5); 3.0279 (0.6); 3.0087 (0.6); 2.6187 (14.9); 2.2879 (6.6); 2.2779 (0.6); 2.2753 (0.6); 2.2547 (0.6); 2.1690 (0.5); 1.6528 (16.0); 1.6080 (2.0); 1.2856 (6.0); 1.2758 (0.6); 1.2688 (6.0); 1.2581 (0.5); −0.0002 (9.8)
1.7: $^1$H-NMR(400.0 MHz, CDCl3):
δ = 8.3239 (1.5); 7.2592 (32.8); 7.0908 (1.0); 7.0720 (1.6); 7.0347 (1.7); 7.0180 (1.3); 6.9955 (0.8); 5.2617 (0.8); 5.2398 (0.5); 5.1639 (0.6); 5.0198 (0.5); 5.0103 (0.6); 5.0040 (0.6); 4.9940 (0.5); 3.0656 (0.6); 3.0463 (0.7); 3.0272 (0.7); 3.0079 (0.8); 2.5531 (0.5); 2.5293 (0.6); 2.4918 (0.5); 2.4155 (16.0); 2.2865 (8.2); 2.2525 (0.6); 1.6811 (1.1); 1.6714 (1.1); 1.5814 (0.6); 1.5475 (7.3); 1.5313 (7.2); 1.2854 (4.1); 1.2823 (4.4); 1.2686 (4.3); 1.2655 (4.6); 0.8817 (0.9); −0.0002 (11.7)
1.8: $^1$H-NMR(400.0 MHz, CDCl3):
δ = 8.4389 (16.0); 7.5181 (2.3); 7.3689 (3.2); 7.3514 (4.0); 7.3469 (3.9); 7.2593 (421.3); 7.2256 (0.8); 7.2085 (0.8); 7.1967 (1.6); 7.1830 (3.3); 7.1785 (3.8); 7.1656 (8.4); 7.1598 (8.6); 7.1468 (3.1); 7.1421 (4.1); 7.1241 (5.2); 7.1026 (2.5); 6.9953 (2.4); 5.3472 (1.7); 5.2770 (2.5); 5.2610 (2.0); 5.2400 (1.0); 2.8819 (0.9); 2.8548 (1.7); 2.8394 (2.8); 2.8173 (1.8); 2.8025 (2.5); 2.7861 (1.6); 2.7580 (0.9); 2.1457 (1.2); 2.1328 (1.2); 2.1225 (1.5); 2.1119 (2.3); 2.1001 (1.5); 2.0863 (1.1); 2.0433 (1.5); 1.9444 (1.4); 1.9227 (2.8); 1.9131 (3.9); 1.8967 (5.4); 1.8816 (5.0); 1.8655 (1.7); 1.6366 (10.2); 1.6188 (1.1); 1.5904 (135.9); 1.5478 (14.0); 1.2766 (0.5); 1.2583 (1.0); 1.2404 (0.6); 0.1461 (0.7); 0.0079 (4.4); −0.0002 (151.6); −0.0085 (5.2); −0.1501 (0.5)
1.9: $^1$H-NMR(400.0 MHz, CDCl3):
δ = 8.7708 (0.8); 8.4565 (16.0); 7.5180 (3.9); 7.3036 (2.6); 7.2849 (3.3); 7.2591 (698.5); 7.2091 (2.1); 7.1894 (2.3); 7.1702 (1.9); 6.9951 (3.8); 6.9158 (2.1); 6.9127 (2.3); 6.8939 (3.6); 6.8783 (1.7); 6.8753 (1.8); 6.8636 (3.5); 6.8431 (3.2); 5.3984 (0.8); 5.2983 (2.5); 5.2373 (0.9); 5.2243 (1.8); 5.2055 (1.6); 4.2966 (1.9); 4.2887 (1.8); 4.2825 (2.1); 4.2708 (2.8); 4.2627 (2.7); 4.2483 (2.1); 4.2409 (2.6); 4.2199 (0.9); 2.6554 (2.5); 2.5939 (2.5); 2.2976 (1.2); 2.2849 (1.5); 2.2753 (1.4); 2.2624 (1.8); 2.2502 (1.2); 2.2412 (1.0); 2.1859 (1.2); 2.1793 (1.5); 2.1717 (1.7); 2.1573 (1.2); 2.1438 (1.1); 2.1365 (0.9); 1.6336 (14.3); 1.5949 (80.0); 1.5332 (23.3); 1.2564 (0.8); 0.0080 (8.2); −0.0002 (248.6); −0.0085 (7.4); −0.1498 (0.9)
1.10: $^1$H-NMR(400.0 MHz, CDCl3):
δ = 8.3194 (5.5); 7.2591 (39.9); 7.1002 (1.1); 7.0812 (1.8); 7.0500 (2.1); 7.0277 (1.4); 7.0087 (0.8); 5.2657 (0.9); 5.2534 (1.2); 5.2336 (1.1); 3.0808 (0.7); 3.0616 (0.7); 3.0421 (0.8); 3.0230 (0.8); 2.5583 (0.5); 2.5353 (0.6); 2.4975 (0.6); 2.2920 (9.1); 1.8485 (0.8); 1.8420 (1.0); 1.8331 (1.9); 1.8294 (2.1); 1.8236 (3.3); 1.8143 (2.0); 1.8105 (2.1); 1.8052 (3.6); 1.7955 (0.7); 1.7918 (0.8); 1.7871 (1.3); 1.5997 (0.8); 1.5447 (3.4); 1.2940 (8.2); 1.2771 (8.1); 0.8816 (1.2); 0.8766 (7.5); 0.8581 (16.0); 0.8394 (6.8); −0.0002 (14.0)

1.11: $^1$H-NMR(400.0 MHz, CDCl3):
δ = 8.4453 (1.5); 7.2583 (54.3); 7.1059 (1.8); 7.0874 (3.0); 7.0393 (5.5); 7.0187 (1.4); 5.4997 (0.9); 5.4771 (1.1); 5.2767 (1.3); 5.2551 (2.1); 5.2331 (1.0); 3.0880 (1.2); 3.0688 (1.2); 3.0493 (1.4); 3.0302 (1.4); 2.5649 (2.7); 2.5409 (1.2); 2.5253 (0.8); 2.5030 (1.0); 2.3287 (0.5); 2.2985 (16.0); 2.2713 (0.9); 2.0432 (1.3); 1.7721 (12.4); 1.7700 (12.8); 1.5843 (7.2); 1.2903 (10.6); 1.2735 (10.6); 1.2582 (1.5); 0.8818 (1.4); 0.8641 (0.6); 0.0080 (0.6); −0.0002 (18.9); −0.0085 (0.6)

1.12: $^1$H-NMR(400.0 MHz, CDCl3):
δ = 8.2929 (1.0); 7.2587 (8.9); 7.1437 (2.0); 7.1238 (1.0); 7.0480 (0.8); 2.6410 (0.5); 2.6100 (7.8); 2.3129 (5.3); 1.6604 (0.7); 1.6417 (16.0); −0.0002 (3.2)

1.13: $^1$H-NMR(400.0 MHz, CDCl3):
δ = 8.3339 (2.0); 7.2593 (39.4); 7.1423 (2.8); 7.1377 (3.0); 7.1263 (2.5); 7.0518 (1.8); 7.0325 (1.2); 5.5874 (1.0); 5.5677 (1.0); 5.3694 (0.6); 5.0080 (1.4); 4.9919 (1.4); 2.9456 (0.7); 2.9371 (0.7); 2.9235 (0.7); 2.9155 (0.7); 2.8555 (1.0); 2.8355 (0.8); 2.8165 (0.5); 2.6824 (0.7); 2.6739 (0.8); 2.6698 (0.7); 2.6614 (0.6); 2.6509 (0.9); 2.6423 (0.8); 2.4191 (16.0); 2.3136 (12.2); 2.0426 (1.8); 1.8703 (1.0); 1.8681 (0.8); 1.8508 (1.1); 1.8488 (1.1); 1.8388 (1.0); 1.8366 (0.8); 1.8171 (0.9); 1.7497 (0.6); 1.5373 (10.6); 1.5210 (10.6); 1.4317 (1.2); 1.2759 (0.5); 1.2580 (1.2); 1.2401 (0.6); −0.0002 (13.8); −0.0084 (0.6)

1.14: $^1$H-NMR(400.0 MHz, CDCl3):
δ = 8.3714 (9.0); 7.2653 (0.5); 7.2645 (0.6); 7.2588 (57.8); 7.0991 (1.6); 7.0801 (2.7); 7.0430 (3.2); 7.0265 (2.2); 7.0077 (1.2); 5.2971 (1.1); 5.2819 (0.9); 5.2578 (1.5); 5.2372 (1.7); 5.2148 (0.7); 3.0774 (1.0); 3.0583 (1.1); 3.0389 (1.2); 3.0199 (1.3); 2.5585 (0.8); 2.5358 (1.0); 2.5201 (0.7); 2.4972 (0.9); 2.2914 (14.1); 2.2792 (1.0); 2.2763 (1.0); 2.2593 (0.7); 2.2563 (0.7); 1.8505 (1.4); 1.8318 (4.7); 1.8133 (5.2); 1.7948 (1.8); 1.6335 (2.5); 1.5498 (27.3); 1.2926 (10.9); 1.2758 (10.6); 0.9062 (7.1); 0.8877 (16.0); 0.8689 (6.6); 0.0080 (0.7); −0.0002 (23.3); −0.0085 (0.6)

1.15: $^1$H-NMR(400.0 MHz, CDCl3):
δ = 8.3960 (4.1); 7.2588 (33.1); 7.0972 (1.0); 7.0782 (1.6); 7.0313 (2.3); 7.0066 (0.8); 6.1721 (1.4); 6.1456 (1.5); 6.1289 (1.6); 6.1024 (1.6); 5.3624 (2.0); 5.3604 (2.0); 5.3193 (2.1); 5.3173 (2.1); 5.2913 (0.7); 5.2604 (0.9); 5.2391 (1.1); 5.2227 (2.2); 5.2206 (2.2); 5.1962 (2.0); 5.1942 (1.9); 3.0743 (0.7); 3.0551 (0.7); 3.0358 (0.8); 3.0167 (0.8); 2.5568 (0.6); 2.5335 (0.6); 2.4972 (1.0); 2.2906 (9.1); 2.2744 (0.6); 2.2713 (0.7); 1.8499 (3.0); 1.6648 (16.0); 1.2863 (7.6); 1.2695 (7.7); 0.8818 (0.9); −0.0002 (12.5); −0.0084 (0.6)

1.16: $^1$H-NMR(400.0 MHz, CDCl3):
δ = 7.2583 (10.9); 7.0910 (0.6); 7.0393 (0.5); 7.0252 (0.7); 2.2985 (2.9); 1.8975 (4.1); 1.2924 (2.4); 1.2756 (2.4); 0.8819 (0.5); 0.2552 (0.5); 0.2545 (0.5); 0.2470 (16.0); 0.2462 (15.8); 0.2390 (1.0); −0.0002 (3.9)

1.17: $^1$H-NMR(400.0 MHz, CDCl3):
δ = 8.3992 (0.6); 7.2657 (0.8); 7.2649 (0.9); 7.2641 (1.0); 7.2587 (88.9); 7.1005 (1.1); 7.0813 (1.8); 7.0543 (1.0); 7.0329 (1.4); 7.0127 (0.8); 6.9947 (0.5); 3.0900 (0.6); 3.0710 (0.7); 3.0513 (0.7); 3.0320 (0.7); 2.5613 (0.6); 2.5388 (0.7); 2.5004 (0.6); 2.3126 (0.7); 2.2965 (9.4); 2.2738 (0.5); 1.8843 (5.8); 1.6732 (16.0); 1.5391 (5.3); 1.2866 (7.1); 1.2697 (7.1); 0.8820 (0.6); 0.0079 (1.0); −0.0002 (33.4); −0.0085 (1.0)

1.18: $^1$H-NMR(400.0 MHz, CDCl3):
δ = 8.5833 (3.8); 7.5182 (0.9); 7.2698 (0.6); 7.2690 (0.6); 7.2682 (0.8); 7.2674 (0.9); 7.2666 (0.9); 7.2658 (1.1); 7.2650 (1.3); 7.2642 (1.6); 7.2633 (2.1); 7.2593 (147.4); 7.2561 (5.7); 7.2552 (4.5); 7.2544 (3.7); 7.2536 (3.1); 7.2528 (2.7); 7.2520 (2.3); 7.2512 (1.8); 7.2504 (1.6); 7.2496 (1.4); 7.2488 (1.3); 7.2480 (1.3); 7.2472 (1.2); 7.2464 (1.1); 7.2456 (1.0); 7.2448 (1.0); 7.2440 (0.9); 7.2432 (0.9); 7.2424 (0.8); 7.2416 (0.8); 7.2408 (0.8); 7.2400 (0.7); 7.2392 (0.7); 7.2384 (0.6); 7.2376 (0.6); 7.2368 (0.6); 7.2360 (0.6); 7.2352 (0.6); 7.2345 (0.6); 7.2337 (0.5); 7.2256 (0.6); 7.2241 (0.5); 7.2093 (0.6); 7.1029 (0.9); 7.0832 (1.7); 7.0317 (3.9); 7.0131 (0.9); 6.9953 (0.9); 5.2991 (0.7); 5.2789 (1.1); 5.2583 (1.2); 3.0819 (0.7); 3.0628 (0.8); 3.0436 (0.9); 3.0244 (0.9); 2.7281 (8.5); 2.5647 (0.6); 2.5418 (0.7); 2.5030 (0.6); 2.3370 (2.4); 2.2950 (9.1); 2.2619 (0.6); 1.8295 (16.0); 1.5415 (3.6); 1.2938 (6.3); 1.2915 (4.9); 1.2770 (6.5); 1.2747 (4.9); 0.8819 (1.3); 0.0080 (2.1); −0.0002 (79.7); −0.0085 (2.8)

1.19: $^1$H-NMR(400.0 MHz, CDCl3):
δ = 8.4958 (2.2); 7.2581 (32.0); 7.1024 (1.9); 7.0836 (3.2); 7.0448 (2.7); 7.0329 (2.8); 7.0135 (1.5); 5.8380 (0.8); 5.8343 (1.1); 5.8218 (0.8); 5.8180 (1.1); 5.7177 (0.8); 5.7140 (1.1); 5.7015 (0.8); 5.6977 (1.1); 5.3427 (0.7); 5.3214 (0.9); 5.2679 (1.3); 5.2469 (1.9); 5.2252 (0.9); 5.1900 (0.9); 3.0865 (1.2); 3.0673 (1.3); 3.0479 (1.4); 3.0287 (1.4); 2.5563 (1.0); 2.5340 (1.2); 2.5178 (0.9); 2.4955 (1.1); 2.3243 (0.7); 2.3219 (0.7); 2.2962 (16.0); 2.2684 (0.9); 2.2661 (0.8); 1.9444 (0.7); 1.9129 (1.1); 1.7319 (6.5); 1.7299 (4.2); 1.7157 (6.6); 1.7137 (4.2); 1.6705 (6.9); 1.6542 (6.6); 1.5920 (4.4); 1.5767 (5.6); 1.5586 (7.5); 1.5415 (4.1); 1.3039 (0.8); 1.2817 (8.2); 1.2772 (8.7); 1.2648 (10.1); 1.2605 (9.6); 0.8987 (1.5); 0.8817 (5.3); 0.8640 (2.0); −0.0002 (14.1)

1.20: $^1$H-NMR(400.0 MHz, CDCl3):
δ = 8.4658 (5.6); 7.2615 (39.0); 7.1028 (1.8); 7.0839 (3.0); 7.0458 (3.5); 7.0294 (2.4); 7.0105 (1.4); 7.0089 (1.4); 5.3335 (0.8); 5.3105 (1.4); 5.2616 (1.5); 5.2400 (2.0); 5.2177 (0.8); 3.0764 (1.2); 3.0573 (1.2); 3.0380 (1.4); 3.0189 (1.4); 2.5619 (0.9); 2.5387 (1.1); 2.5236 (0.8); 2.5004 (1.0); 2.3158 (0.5); 2.2940 (16.0); 2.2761 (1.3); 2.2590 (0.8); 2.2561 (0.7); 2.0471 (1.8); 1.5631 (3.0); 1.5052 (26.4); 1.2956 (14.5); 1.2788 (14.8); 1.2636 (5.0); 1.2602 (4.9); 1.2501 (2.3); 1.2426 (2.2); 1.2365 (1.2); 1.2290 (2.5); 1.2231 (0.9); 1.2155 (1.5); 1.2083 (1.5); 1.1946 (0.8); 0.8985 (2.4); 0.8816 (8.2); 0.8639 (3.2); 0.5906 (0.5); 0.5776 (0.6); 0.5739 (1.6); 0.5686 (2.1); 0.5632 (0.6); 0.5542 (0.8); 0.5524 (0.8); 0.5472 (1.8); 0.5435 (0.6); 0.5341 (2.2); 0.5133 (2.1); 0.5073 (1.0); 0.4874 (1.5); 0.4725 (0.7); 0.4659 (1.0); 0.4643 (1.0); 0.4576 (3.8); 0.4505 (1.5); 0.4486 (1.6); 0.4440 (3.8); 0.4335 (1.2); 0.4321 (1.3); 0.0079 (0.6); −0.0002 (21.5); −0.0085 (0.8)

1.21: ¹H-NMR(400.0 MHz, CDCl3):
δ = 8.3376 (2.5); 7.5178 (0.6); 7.4794 (2.0); 7.4758 (2.8); 7.4707 (0.9); 7.4609 (1.5); 7.4581 (3.2); 7.4562 (2.8); 7.4550 (3.0); 7.4498 (0.6); 7.3954 (0.5); 7.3931 (1.2); 7.3911 (1.9); 7.3864 (0.7); 7.3783 (0.6); 7.3730 (3.5); 7.3692 (1.8); 7.3574 (1.0); 7.3535 (1.8); 7.3104 (0.8); 7.3071 (1.6); 7.3037 (0.9); 7.2942 (0.7); 7.2887 (1.6); 7.2834 (0.5); 7.2739 (0.5); 7.2707 (0.9); 7.2673 (0.9); 7.2588 (112.3); 7.0915 (0.9); 7.0725 (1.6); 7.0232 (3.7); 7.0044 (0.8); 6.9949 (0.7); 5.2450 (0.7); 5.2233 (1.1); 5.2013 (0.6); 3.0742 (0.6); 3.0550 (0.7); 3.0359 (0.8); 3.0165 (0.8); 2.5465 (0.5); 2.5237 (0.6); 2.4859 (0.6); 2.2883 (8.7); 2.1441 (4.5); 1.9603 (16.0); 1.2730 (8.7); 1.2562 (8.4); 0.8818 (1.3); 0.0079 (1.5); −0.0002 (49.1); −0.0069 (0.7); −0.0085 (1.5)

1.22: ¹H-NMR(400.0 MHz, CDCl3):
δ = 8.5843 (1.0); 7.2594 (64.8); 7.1022 (0.7); 7.0820 (1.2); 7.0303 (2.6); 7.0133 (0.7); 5.2659 (0.9); 3.0689 (0.5); 3.0494 (0.6); 3.0303 (0.6); 2.3124 (0.6); 2.2945 (6.1); 2.2675 (1.3); 1.9191 (16.0); 1.7767 (9.9); 1.2932 (3.3); 1.2899 (3.5); 1.2764 (3.4); 1.2731 (3.6); 1.2622 (0.7); 0.8819 (1.0); 0.0080 (0.8); −0.0002 (28.0); −0.0085 (0.9)

1.23: ¹H-NMR(400.0 MHz, CDCl3):
δ = 8.3192 (0.8); 7.2583 (16.9); 7.0997 (0.8); 7.0804 (1.6); 7.0527 (0.8); 7.0269 (0.9); 7.0081 (0.5); 3.0882 (0.5); 3.0690 (0.6); 3.0496 (0.6); 3.0305 (0.6); 2.3131 (0.5); 2.3012 (3.8); 2.2888 (3.8); 1.7130 (1.8); 1.7097 (1.9); 1.6974 (2.2); 1.6941 (2.0); 1.6695 (16.0); 1.6519 (2.1); 1.6486 (2.1); 1.6362 (1.8); 1.6329 (1.9); 1.2985 (3.4); 1.2812 (5.4); 1.2636 (4.0); 0.8987 (0.6); 0.8818 (2.0); 0.8641 (0.7); −0.0002 (9.8)

1.24: ¹H-NMR(400.0 MHz, CDCl3):
δ = 8.3418 (4.4); 7.2590 (16.5); 7.1027 (0.8); 7.0838 (1.3); 7.0491 (1.5); 7.0307 (1.0); 7.0116 (0.6); 5.2640 (0.7); 5.2429 (0.9); 3.1205 (16.0); 3.0829 (0.5); 3.0639 (0.6); 3.0445 (0.6); 3.0253 (0.6); 2.2944 (6.8); 1.5281 (22.8); 1.2967 (6.1); 1.2799 (5.9); −0.0002 (8.8)

1.25: ¹H-NMR(400.0 MHz, CDCl3):
δ = 8.3854 (6.3); 7.5179 (0.5); 7.2688 (0.6); 7.2681 (0.6); 7.2590 (95.9); 7.0996 (2.1); 7.0806 (3.2); 7.0329 (4.1); 7.0297 (4.1); 7.0085 (1.6); 6.9950 (0.6); 5.4067 (0.5); 5.2654 (1.3); 5.2436 (2.2); 5.2218 (1.0); 3.0824 (1.3); 3.0633 (1.4); 3.0440 (1.5); 3.0249 (1.6); 2.5965 (0.6); 2.5936 (0.6); 2.5597 (1.1); 2.5369 (1.2); 2.5218 (0.9); 2.4985 (2.4); 2.3287 (0.6); 2.3225 (0.6); 2.3063 (1.8); 2.2882 (16.0); 2.2721 (1.0); 1.7697 (0.9); 1.7655 (0.6); 1.7495 (1.6); 1.7279 (4.3); 1.7219 (0.5); 1.7139 (3.4); 1.7097 (1.7); 1.7026 (0.8); 1.6936 (1.5); 1.6892 (2.0); 1.6855 (1.3); 1.6810 (1.2); 1.6739 (1.0); 1.6582 (0.7); 1.5957 (8.7); 1.5658 (24.8); 1.3113 (0.7); 1.3040 (1.0); 1.2929 (12.2); 1.2761 (12.1); 0.9444 (9.5); 0.9290 (9.0); 0.9147 (0.5); 0.8893 (10.7); 0.8818 (4.5); 0.8737 (8.9); 0.8642 (1.7); 0.0080 (1.3); 0.0056 (0.5); −0.0002 (40.4); −0.0066 (0.6); −0.0084 (1.3)

1.26: ¹H-NMR(400.0 MHz, CDCl3):
δ = 8.3208 (5.9); 7.5173 (1.0); 7.3207 (1.1); 7.3143 (1.5); 7.3102 (1.0); 7.2988 (4.8); 7.2950 (2.4); 7.2848 (2.8); 7.2807 (6.6); 7.2753 (4.8); 7.2712 (3.1); 7.2585 (187.5); 7.2406 (0.7); 7.2088 (0.8); 7.1146 (3.9); 7.1102 (4.2); 7.0952 (4.1); 7.0825 (3.3); 7.0309 (7.2); 7.0140 (1.6); 6.9944 (1.0); 5.2704 (1.3); 5.2484 (2.2); 5.2262 (1.1); 3.1007 (0.9); 3.0943 (0.9); 3.0858 (1.4); 3.0672 (4.0); 3.0610 (3.0); 3.0476 (1.7); 3.0352 (5.3); 3.0287 (2.0); 3.0018 (1.7); 2.5617 (1.0); 2.5405 (1.2); 2.5244 (0.9); 2.5004 (1.0); 2.3308 (0.7); 2.3035 (16.0); 2.2780 (0.8); 1.8251 (5.7); 1.8233 (5.6); 1.5628 (18.2); 1.2916 (10.1); 1.2760 (10.1); 0.8983 (0.5); 0.8819 (1.8); 0.8644 (0.7); 0.0080 (2.2); −0.0002 (76.9); −0.0085 (2.4)

1.27: ¹H-NMR(599.8 MHz, CDCl3):
δ = 8.3419 (4.5); 7.2576 (7.9); 7.0903 (7.2); 7.0777 (10.1); 7.0460 (11.0); 7.0342 (1.7); 7.0180 (8.1); 7.0052 (5.8); 5.6776 (0.5); 5.6621 (0.9); 5.6386 (9.2); 5.5846 (2.8); 5.5698 (4.0); 5.5560 (1.6); 5.2463 (4.2); 5.2318 (7.5); 5.2172 (3.9); 4.9608 (1.5); 4.9582 (2.1); 4.9555 (1.6); 4.7597 (1.9); 3.0594 (4.0); 3.0466 (4.3); 3.0338 (4.6); 3.0210 (4.6); 2.5497 (0.8); 2.5398 (2.5); 2.5251 (4.4); 2.5140 (3.3); 2.4989 (3.6); 2.4821 (2.4); 2.4596 (1.2); 2.3889 (0.3); 2.3193 (1.2); 2.3092 (2.2); 2.2973 (2.1); 2.2852 (50.0); 2.2714 (4.8); 2.2589 (3.2); 2.2451 (1.5); 2.2336 (0.6); 2.1784 (0.4); 2.1050 (0.4); 2.0674 (1.4); 2.0273 (0.6); 1.8556 (0.3); 1.7539 (37.1); 1.7523 (38.0); 1.7367 (0.8); 1.7106 (0.4); 1.7013 (0.5); 1.6449 (0.6); 1.6328 (6.9); 1.6224 (0.6); 1.6070 (40.7); 1.5967 (44.6); 1.5880 (2.4); 1.5819 (1.5); 1.5780 (1.2); 1.5413 (7.8); 1.5388 (8.1); 1.5202 (0.4); 1.5000 (0.4); 1.4889 (0.4); 1.3120 (0.6); 1.3004 (1.1); 1.2807 (27.5); 1.2695 (28.2); 1.2629 (8.0); 1.2196 (0.3); 1.1751 (0.4); 1.1522 (0.3); 1.0008 (0.5); 0.9681 (0.4); 0.9050 (0.8); 0.8930 (3.5); 0.8815 (6.8); 0.8695 (3.4); −0.0001 (1.6)

1.28: ¹H-NMR(400.0 MHz, CDCl3):
δ = 8.3562 (6.0); 7.2584 (35.2); 7.1006 (1.9); 7.0817 (3.1); 7.0465 (3.6); 7.0285 (2.4); 7.0095 (1.4); 7.0080 (1.4); 5.8705 (0.5); 5.8543 (1.1); 5.8451 (0.6); 5.8380 (0.6); 5.8286 (1.5); 5.8117 (1.6); 5.8022 (0.6); 5.7951 (0.6); 5.7860 (1.3); 5.7697 (0.6); 5.3736 (0.8); 5.3511 (1.1); 5.2597 (1.4); 5.2381 (2.1); 5.2160 (1.0); 5.0544 (0.8); 5.0503 (2.2); 5.0460 (2.3); 5.0419 (1.1); 5.0115 (0.7); 5.0074 (2.0); 5.0031 (2.1); 4.9990 (0.9); 4.9875 (0.9); 4.9844 (2.1); 4.9801 (1.9); 4.9768 (1.2); 4.9621 (0.9); 4.9589 (2.0); 4.9546 (1.8); 4.9514 (0.8); 3.0792 (1.2); 3.0601 (1.3); 3.0407 (1.4); 3.0216 (1.4); 2.5586 (1.0); 2.5361 (1.1); 2.5205 (0.8); 2.4977 (1.0); 2.3181 (0.6); 2.2924 (16.0); 2.2821 (1.4); 2.2786 (1.4); 2.2613 (0.9); 2.2590 (0.8); 2.1342 (0.7); 2.1314 (0.6); 2.1170 (0.9); 2.1136 (1.1); 2.0966 (1.2); 2.0931 (1.2); 2.0761 (1.1); 2.0732 (1.2); 2.0568 (1.0); 2.0536 (1.0); 2.0423 (0.7); 2.0357 (0.7); 1.9059 (4.0); 1.8849 (4.3); 1.8643 (1.8); 1.7589 (5.4); 1.5692 (23.9); 1.5350 (0.5); 1.2928 (13.2); 1.2760 (13.3); 1.2684 (2.4); 1.2655 (2.4); 0.8987 (1.1); 0.8818 (3.8); 0.8641 (1.5); −0.0002 (13.3)

1.30: ¹H-NMR(400.6 MHz, CDCl3):
δ = 8.4470 (16.0); 7.5189 (0.6); 7.3510 (2.6); 7.3498 (2.6); 7.3326 (3.6); 7.2830 (0.7); 7.2806 (0.8); 7.2766 (1.3); 7.2759 (1.3); 7.2711 (0.6); 7.2702 (0.6); 7.2694 (0.8); 7.2604 (107.4); 7.2485 (0.8); 7.2451 (4.1); 7.2438 (4.5); 7.2417 (3.6); 7.2403 (3.5); 7.2334 (0.6); 7.2261 (2.3); 7.2223 (3.8); 7.2168 (2.1); 7.2046 (2.6); 7.2019 (1.9); 7.1997 (2.1); 7.1876 (1.0); 7.1826 (0.8); 6.9968 (0.6); 5.6179 (0.9); 5.5986 (2.6); 5.5789 (2.8); 5.5597 (1.1); 5.3859 (1.4); 5.3648 (1.2); 3.1486 (0.5); 3.0496 (0.8); 3.0405 (0.9); 3.0278 (0.8); 3.0189 (0.9); 3.0099 (1.6); 3.0009 (1.8); 2.9882 (1.7); 2.9793 (1.8); 2.9391 (1.2); 2.9183 (2.6); 2.8984 (2.0); 2.8786 (1.3); 2.8585 (0.8); 2.7252 (1.3); 2.7162 (1.2); 2.7058 (1.6); 2.6979 (1.6); 2.6936 (1.6); 2.6875 (1.4); 2.6845 (1.5); 2.6785 (1.2); 2.6752 (1.8); 2.6742 (1.8); 2.6662 (1.7); 2.6558 (1.3); 2.6468 (1.1); 2.0686 (0.8); 2.0453 (1.2); 1.9253 (1.4); 1.9062 (1.5); 1.9039 (2.8); 1.8937 (1.3); 1.8849 (2.7); 1.8825 (1.6); 1.8746 (1.5); 1.8723 (2.6); 1.8634 (1.3); 1.8532 (2.6); 1.8509 (1.4); 1.8317 (1.1); 1.6626 (1.1); 1.6437 (0.9); 1.6321 (0.8); 1.6173 (1.1); 1.5939 (123.8); 1.2595 (1.0); 1.2555 (0.6); 0.0079 (2.0); −0.0002 (76.4); −0.0059 (0.9); −0.0068 (0.7); −0.0085 (2.3)

-continued 1.31: $^1$H-NMR(400.0 MHz, CDCl3):
δ = 8.4442 (7.4); 7.2592 (47.8); 7.1866 (2.0); 7.1768 (3.3); 7.1709 (2.7); 7.1685 (3.0); 7.0964 (2.1); 7.0771 (1.4); 5.5694 (1.3); 5.5498 (1.5); 5.5308 (0.7); 5.4296 (0.8); 5.4093 (0.7); 2.9725 (0.5); 2.9636 (0.9); 2.9550 (0.9); 2.9421 (0.9); 2.9334 (0.9); 2.8929 (0.6); 2.8725 (1.4); 2.8527 (1.1); 2.8333 (0.7); 2.7240 (0.6); 2.7152 (0.6); 2.7056 (0.8); 2.6969 (0.9); 2.6925 (0.9); 2.6865 (0.8); 2.6836 (0.8); 2.6776 (0.7); 2.6740 (1.0); 2.6653 (1.0); 2.6522 (1.4); 2.6460 (0.8); 2.6331 (3.8); 2.6141 (4.0); 2.5951 (1.5); 1.9134 (0.6); 1.8921 (1.3); 1.8819 (0.6); 1.8731 (1.3); 1.8605 (1.2); 1.8517 (0.7); 1.8414 (1.2); 1.8199 (0.6); 1.6796 (7.1); 1.5932 (53.5); 1.5442 (0.7); 1.2810 (0.6); 1.2648 (1.9); 1.2584 (1.4); 1.2301 (7.7); 1.2111 (16.0); 1.1921 (7.6); 0.8987 (0.9); 0.8818 (2.9); 0.8641 (1.2); 0.0080 (0.9); −0.0002 (26.4); −0.0085 (1.2)

1.38: $^1$H-NMR(400.0 MHz, CDCl3):
δ = 8.4647 (4.3); 7.5181 (1.4); 7.2592 (248.5); 7.2082 (0.9); 7.0902 (2.5); 7.0053 (1.4); 6.9952 (1.3); 6.9851 (1.6); 6.7629 (3.5); 6.7422 (2.9); 5.2052 (1.1); 4.2649 (1.2); 4.2503 (1.4); 4.2421 (2.1); 4.2349 (1.5); 4.2132 (1.6); 2.2677 (1.2); 2.2416 (16.0); 2.1696 (3.2); 2.1493 (1.1); 2.1423 (1.1); 2.1279 (1.0); 2.1144 (0.8); 1.6721 (4.6); 1.5984 (44.3); 1.5405 (2.0); 1.2643 (1.0); 0.8820 (1.2); 0.8635 (0.7); 0.0078 (5.2); −0.0002 (106.4); −0.0085 (4.3)

1.45: $^1$H-NMR(400.0 MHz, CDCl3):
δ = 8.3730 (2.9); 7.3054 (1.5); 7.2966 (4.2); 7.2838 (6.0); 7.2746 (2.4); 7.2599 (48.2); 5.1504 (1.1); 5.0301 (0.9); 5.0152 (0.9); 4.4956 (0.6); 4.4754 (1.3); 4.4581 (1.2); 4.4380 (0.6); 3.4008 (1.1); 3.3809 (1.1); 3.3613 (1.3); 3.3416 (1.2); 3.0108 (1.1); 2.9893 (1.0); 2.9716 (0.9); 2.9500 (0.8); 2.4650 (16.0); 2.0433 (2.0); 1.8384 (0.8); 1.5392 (8.3); 1.5230 (8.2); 1.2762 (0.6); 1.2584 (1.3); 1.2406 (0.6); −0.0002 (18.7); −0.0081 (0.9)

1.46: $^1$H-NMR(400.0 MHz, CDCl3):
δ = 8.3307 (0.6); 7.2676 (0.7); 7.2594 (66.3); 7.1358 (0.6); 7.1164 (1.4); 7.0967 (0.8); 6.9844 (1.0); 6.9650 (0.8); 6.7357 (1.2); 6.7173 (1.1); 5.0059 (0.5); 4.9965 (0.5); 4.9899 (0.5); 4.9805 (0.5); 3.8261 (16.0); 2.7101 (0.6); 2.6527 (0.6); 2.4185 (7.2); 2.0433 (1.0); 1.9062 (0.6); 1.8917 (0.8); 1.8797 (0.8); 1.8618 (1.1); 1.8452 (0.7); 1.6675 (0.7); 1.6584 (0.7); 1.5349 (6.9); 1.5186 (6.8); 0.0080 (0.9); −0.0002 (27.6); −0.0085 (0.8)

1.47: $^1$H-NMR(400.0 MHz, CDCl3):
δ = 8.3280 (1.8); 7.3384 (1.2); 7.3205 (1.5); 7.2594 (26.6); 7.2504 (1.6); 7.2464 (2.7); 7.2438 (2.7); 7.2296 (1.7); 7.2274 (1.5); 7.2117 (0.8); 7.2053 (1.2); 7.1998 (0.8); 7.1874 (1.1); 7.1827 (0.9); 5.6212 (0.9); 5.6015 (0.9); 5.0053 (0.9); 4.9892 (0.8); 4.1292 (0.5); 4.1114 (0.5); 2.9974 (0.7); 2.9885 (0.7); 2.9757 (0.7); 2.9669 (0.7); 2.9284 (0.5); 2.9079 (1.1); 2.8876 (0.8); 2.8687 (0.5); 2.6928 (0.7); 2.6839 (0.6); 2.6808 (0.5); 2.6720 (0.5); 2.6611 (0.7); 2.6522 (1.6); 2.4126 (1.5); 2.0424 (2.4); 1.8848 (0.9); 1.8826 (0.7); 1.8654 (0.6); 1.8632 (0.9); 1.8531 (0.8); 1.8509 (0.6); 1.8336 (0.6); 1.8315 (0.8); 1.7599 (0.8); 1.5337 (10.3); 1.5175 (10.2); 1.2757 (0.8); 1.2578 (1.5); 1.2399 (0.7); −0.0002 (11.1)

1.48: $^1$H-NMR(400.0 MHz, CDCl3):
δ = 8.3222 (1.7); 7.2591 (33.2); 7.1638 (2.8); 7.0122 (0.6); 6.9910 (7.1); 6.9867 (3.7); 5.2488 (1.0); 5.2338 (0.8); 5.0036 (0.9); 4.9948 (1.0); 4.9876 (1.0); 4.9787 (0.9); 2.7958 (0.7); 2.7797 (1.2); 2.7597 (0.8); 2.7443 (1.1); 2.7279 (0.7); 2.4074 (16.0); 2.2610 (15.2); 2.1015 (0.5); 2.0932 (0.6); 2.0819 (0.8); 2.0695 (0.6); 2.0426 (1.6); 1.9110 (0.7); 1.9048 (0.7); 1.8905 (1.2); 1.8839 (1.3); 1.8727 (1.5); 1.8681 (1.6); 1.8564 (1.3); 1.8485 (1.6); 1.8329 (0.8); 1.7305 (1.4); 1.5337 (12.3); 1.5175 (12.1); 1.2758 (0.5); 1.2580 (1.0); −0.0002 (13.8)

1.49: $^1$H-NMR(400.0 MHz, CDCl3):
δ = 8.3357 (1.7); 7.2597 (56.1); 7.0894 (1.8); 7.0872 (1.8); 6.9955 (0.5); 6.9917 (1.1); 6.9862 (1.0); 6.9709 (1.2); 6.9653 (1.1); 6.7497 (2.8); 6.7289 (2.4); 5.2014 (0.8); 5.1834 (0.7); 5.0178 (0.7); 5.0084 (0.8); 5.0016 (0.8); 4.9921 (0.7); 4.2544 (0.9); 4.2454 (0.8); 4.2394 (1.0); 4.2296 (1.5); 4.2217 (1.0); 4.2068 (0.9); 4.2001 (1.1); 2.4234 (16.0); 2.2627 (0.7); 2.2598 (0.6); 2.2534 (0.6); 2.2503 (0.8); 2.2469 (0.6); 2.2330 (13.0); 2.1354 (0.6); 2.1277 (0.6); 2.0432 (1.5); 1.6864 (1.2); 1.6770 (1.2); 1.5369 (8.6); 1.5207 (8.5); 1.2584 (1.1); 0.0079 (0.7); −0.0002 (23.4); −0.0085 (0.7)

1.50: $^1$H-NMR(400.0 MHz, CDCl3):
δ = 8.3483 (1.6); 7.2592 (66.5); 7.1679 (2.7); 7.1578 (2.3); 7.0856 (1.7); 7.0663 (1.1); 5.5936 (0.9); 5.5739 (0.9); 5.0203 (0.8); 5.0111 (0.8); 5.0040 (0.8); 4.9949 (0.8); 2.9557 (0.7); 2.9471 (0.7); 2.9340 (0.7); 2.9257 (0.7); 2.8849 (0.5); 2.8647 (1.1); 2.8445 (0.8); 2.8250 (0.6); 2.8205 (0.6); 2.6948 (0.7); 2.6862 (0.7); 2.6822 (0.6); 2.6736 (0.6); 2.6632 (0.8); 2.6545 (0.8); 2.6439 (1.4); 2.6355 (0.7); 2.6248 (3.1); 2.6058 (3.2); 2.5869 (1.1); 2.4309 (16.0); 2.0432 (2.3); 1.8810 (0.8); 1.8595 (0.8); 1.8496 (0.8); 1.8279 (0.7); 1.6879 (1.3); 1.6788 (1.3); 1.5421 (10.7); 1.5259 (10.6); 1.2762 (0.8); 1.2584 (1.5); 1.2405 (0.8); 1.2256 (6.4); 1.2066 (13.4); 1.1876 (6.1); 0.0080 (1.0); −0.0002 (28.1); −0.0085 (0.8)

1.44: $^1$H-NMR(400.0 MHz, CDCl3):
δ = 7.2592 (57.7); 7.1173 (0.9); 7.0975 (0.6); 6.9880 (0.7); 6.9685 (0.6); 6.7356 (0.7); 6.7173 (0.6); 3.8259 (9.0); 2.6305 (3.0); 2.1694 (1.0); 1.8646 (0.6); 1.6446 (16.0); 1.5773 (1.3); 0.8819 (0.5); 0.0079 (0.8); −0.0002 (24.9); −0.0085 (0.8)

1.51: $^1$H-NMR(400.0 MHz, CDCl3):
δ = 8.2974 (0.7); 8.2881 (1.0); 7.3018 (0.6); 7.2593 (30.6); 7.2397 (0.5); 7.2316 (0.8); 7.2280 (1.2); 7.2222 (1.5); 7.2182 (1.5); 7.2145 (1.0); 7.2135 (1.0); 7.2043 (1.2); 7.2009 (1.4); 7.1913 (1.8); 7.1891 (1.2); 2.6519 (0.5); 2.6427 (0.5); 2.6208 (6.7); 2.6157 (9.4); 2.6046 (0.7); 2.0428 (1.0); 1.6499 (14.1); 1.6471 (16.0); 1.6059 (0.6); 1.5992 (3.7); 1.5798 (0.8); 1.2993 (3.8); 1.2825 (4.0); 1.2759 (1.2); 1.2649 (1.9); 1.2581 (1.6); 0.9411 (3.9); 0.9234 (3.9); 0.8987 (1.1); 0.8818 (3.8); 0.8640 (1.4); −0.0002 (13.5)

1.43: $^1$H-NMR(400.0 MHz, CDCl3):
δ = 8.4476 (4.2); 7.5182 (0.7); 7.2593 (123.0); 7.1642 (3.2); 7.0265 (0.5); 7.0054 (8.4); 6.9953 (0.9); 5.2429 (1.0); 5.2218 (0.9); 2.8089 (0.8); 2.7931 (1.2); 2.7778 (0.6); 2.7672 (0.7); 2.7520 (1.1); 2.7360 (0.7); 2.2699 (16.0); 2.1696 (0.6); 2.1287 (0.5); 2.1123 (0.5); 2.1054 (0.8); 2.0947 (0.9); 2.0838 (0.6); 2.0668 (0.6); 2.0434 (0.9); 1.9337 (0.6); 1.9283 (0.8); 1.9196 (0.7); 1.9123 (1.3); 1.9057 (1.2); 1.8971 (1.8); 1.8916 (1.2); 1.8801 (1.7); 1.8745 (1.5); 1.8642 (1.2); 1.8590 (1.8); 1.8428 (0.8); 1.6687 (6.2); 1.6197 (1.4); 1.5936 (60.3); 1.2762 (0.5); 1.2643 (0.8); 1.2585 (1.0); 0.8818 (1.2); 0.0080 (1.8); −0.0002 (53.7); −0.0085 (1.5)

1.56: ¹H-NMR(400.0 MHz, CDCl3):
δ = 8.3309 (1.7); 7.5184 (0.8); 7.2944 (1.6); 7.2916 (1.5); 7.2901 (1.5); 7.2830 (3.0); 7.2781 (0.8); 7.2773 (0.8); 7.2765 (0.8); 7.2748 (1.1); 7.2741 (1.1); 7.2732 (1.2); 7.2717 (1.1); 7.2700 (1.4); 7.2693 (1.6); 7.2685 (1.6); 7.2678 (1.6); 7.2669 (1.7); 7.2661 (1.8); 7.2652 (2.1); 7.2595 (134.0); 7.2491 (0.6); 7.2483 (0.5); 7.2474 (0.5); 7.2371 (0.8); 6.9955 (0.8); 5.1205 (0.8); 5.1066 (0.6); 4.4671 (0.6); 4.4523 (0.6); 4.4507 (0.6); 4.4472 (0.5); 4.2003 (0.7); 4.1822 (1.0); 4.1640 (0.7); 3.4009 (0.5); 3.3615 (0.6); 3.3415 (0.6); 2.6620 (9.3); 2.3326 (3.4); 2.0433 (1.3); 1.6545 (16.0); 1.3064 (1.7); 1.2951 (0.7); 1.2886 (3.5); 1.2763 (0.8); 1.2708 (1.8); 1.2596 (2.3); 1.2540 (1.2); 1.2442 (1.9); 1.2406 (0.7); 0.8819 (1.0); 0.0080 (1.5); 0.0048 (0.6); 0.0040 (0.7); −0.0002 (52.0); −0.0066 (0.6); −0.0085 (1.4)
1.55: ¹H-NMR(400.0 MHz, CDCl3):
δ = 8.4466 (2.9); 7.2594 (62.0); 7.2447 (0.6); 7.2411 (0.9); 7.2346 (1.0); 7.2318 (1.3); 7.2279 (0.9); 7.2175 (0.9); 7.2144 (1.1); 7.2110 (1.2); 7.2017 (1.6); 3.0929 (0.5); 3.0737 (0.5); 1.6650 (2.1); 1.6006 (16.0); 1.5961 (13.2); 1.3051 (3.2); 1.2883 (3.2); 0.9503 (2.7); 0.9326 (2.7); 0.0080 (0.7); −0.0002 (25.4); −0.0085 (0.8)
1.54: ¹H-NMR(400.0 MHz, CDCl3):
δ = 8.3201 (0.6); 7.3278 (0.5); 7.2594 (41.4); 7.2522 (0.8); 7.2480 (1.0); 7.2451 (1.0); 7.2312 (0.6); 7.2289 (0.5); 7.2091 (0.6); 2.6314 (6.0); 1.6497 (16.0); 1.5842 (1.8); −0.0002 (16.5)
1.52: ¹H-NMR(400.0 MHz, CDCl3):
δ = 8.2949 (0.8); 7.2588 (11.7); 7.1748 (1.0); 6.9895 (2.2); 6.9848 (1.2); 5.2192 (0.9); 2.6062 (6.3); 2.2616 (4.9); 2.0424 (0.6); 1.8478 (0.6); 1.6414 (16.0); 1.6109 (1.5); 1.2755 (0.8); 1.2650 (1.6); 1.2580 (1.1); 0.8987 (0.8); 0.8818 (2.9); 0.8641 (1.1); −0.0002 (5.2)
1.53: ¹H-NMR(400.0 MHz, CDCl3):
δ = 7.5183 (0.5); 7.2594 (93.5); 7.0774 (0.9); 6.9953 (1.0); 6.9741 (0.6); 6.9686 (0.5); 6.7516 (1.4); 6.7308 (1.1); 4.2488 (0.8); 4.2419 (0.6); 4.2377 (0.5); 4.2213 (0.5); 2.6710 (2.7); 2.6593 (0.6); 2.2344 (6.4); 2.1697 (0.6); 1.6560 (16.0); 1.6143 (1.3); 1.5418 (0.8); 0.8819 (0.5); 0.0080 (1.2); −0.0002 (39.3); −0.0085 (1.2)
1.57: ¹H-NMR(400.0 MHz, CDCl3):
δ = 8.3163 (1.1); 7.2592 (40.2); 7.1771 (1.6); 7.1576 (0.8); 7.0841 (0.6); 2.6451 (0.6); 2.6234 (7.9); 2.6073 (1.2); 1.6505 (16.0); 1.5726 (1.3); 1.2269 (2.5); 1.2080 (5.5); 1.1889 (2.4); −0.0002 (15.1)
1.58: ¹H-NMR(400.0 MHz, CDCl3):
δ = 8.7714 (2.7); 8.4129 (2.4); 7.5177 (1.0); 7.2719 (0.5); 7.2663 (1.2); 7.2588 (192.9); 7.1406 (1.3); 7.1082 (1.8); 7.0898 (3.0); 7.0542 (3.4); 7.0401 (2.6); 7.0211 (1.4); 6.9948 (1.0); 5.4121 (0.8); 5.3898 (1.0); 5.2741 (1.3); 5.2529 (2.0); 5.2311 (1.0); 4.1303 (0.9); 4.1124 (0.9); 3.2093 (2.0); 3.0927 (1.1); 3.0738 (1.2); 3.0546 (1.4); 3.0352 (1.4); 2.9891 (0.5); 2.5662 (0.9); 2.5432 (1.1); 2.5258 (0.9); 2.5035 (1.1); 2.3330 (5.7); 2.3175 (1.1); 2.3012 (15.7); 2.2804 (1.0); 2.2649 (3.3); 2.2175 (0.7); 2.1989 (1.1); 2.1802 (1.4); 2.1619 (1.2); 2.1427 (0.6); 2.0662 (1.3); 2.0478 (1.7); 2.0435 (4.5); 2.0294 (1.2); 2.0107 (0.8); 2.0044 (1.3); 1.5553 (3.2); 1.3196 (5.4); 1.3028 (5.9); 1.2950 (16.0); 1.2781 (15.9); 1.2651 (3.0); 1.2584 (4.3); 1.2405 (1.6); 0.9450 (4.3); 0.9264 (8.3); 0.9076 (3.9); 0.8986 (2.2); 0.8963 (2.2); 0.8819 (6.6); 0.8774 (2.6); 0.8759 (2.5); 0.8641 (2.4); 0.8586 (1.1); 0.0079 (2.0); 0.0062 (0.6); 0.0054 (0.6); 0.0046 (0.8); −0.0002 (67.8); −0.0028 (3.3); −0.0052 (1.0); −0.0061 (0.7); −0.0069 (0.6); −0.0085 (2.0)
1.61: ¹H-NMR(400.0 MHz, CDCl3):
δ = 8.7360 (0.7); 8.4536 (10.6); 7.5178 (0.5); 7.2589 (95.1); 7.1008 (1.7); 7.0818 (2.7); 7.0494 (3.1); 7.0278 (2.2); 7.0088 (1.3); 6.9949 (0.6); 5.2436 (1.7); 5.2275 (3.2); 3.0807 (1.0); 3.0617 (1.1); 3.0422 (1.2); 3.0233 (1.2); 2.5611 (0.9); 2.5385 (1.0); 2.5224 (0.8); 2.5001 (0.9); 2.3339 (0.5); 2.3211 (0.6); 2.2934 (12.9); 2.2639 (0.7); 1.5566 (1.4); 1.5255 (14.9); 1.5238 (15.2); 1.5090 (2.1); 1.4860 (1.2); 1.3217 (0.6); 1.2984 (7.8); 1.2965 (8.2); 1.2816 (8.0); 1.2797 (8.3); 1.2648 (2.7); 1.0078 (16.0); 0.9310 (1.0); 0.9174 (1.1); 0.9052 (1.4); 0.8986 (1.7); 0.8936 (1.9); 0.8819 (5.0); 0.8641 (1.7); 0.7779 (0.7); 0.7662 (1.2); 0.7540 (1.3); 0.7421 (0.9); 0.7308 (0.6); 0.3963 (0.6); 0.3849 (0.8); 0.3735 (1.4); 0.3621 (1.6); 0.3508 (1.2); 0.3338 (1.6); 0.3243 (1.6); 0.3212 (1.6); 0.3109 (1.8); 0.3014 (0.8); 0.2983 (0.8); 0.2881 (0.7); 0.0080 (1.2); −0.0002 (36.2); −0.0086 (1.3)
1.60: ¹H-NMR(400.0 MHz, CDCl3):
δ = 8.3148 (5.3); 7.5179 (0.5); 7.2637 (9.3); 7.2590 (72.5); 7.2356 (1.4); 7.2255 (1.9); 7.2129 (1.6); 7.0989 (0.6); 7.0800 (4.0); 7.0667 (6.4); 5.4440 (0.8); 5.4213 (0.9); 5.2658 (1.1); 4.8215 (1.1); 4.8052 (1.1); 4.1299 (0.5); 4.1120 (0.6); 2.7316 (0.6); 2.6880 (1.2); 2.6522 (0.8); 2.6380 (1.2); 2.6212 (0.8); 2.2448 (16.0); 2.0886 (0.6); 2.0658 (1.0); 2.0537 (1.2); 2.0431 (1.9); 2.0254 (0.6); 1.9941 (0.5); 1.9669 (0.8); 1.9514 (1.1); 1.9294 (2.2); 1.9127 (2.5); 1.7238 (1.3); 1.5356 (11.1); 1.5193 (10.8); 1.2762 (1.0); 1.2584 (1.8); 1.2405 (0.8); 0.8817 (0.6); 0.0045 (3.5); −0.0002 (26.6); −0.0085 (0.9)
1.41: ¹H-NMR(400.0 MHz, CDCl3):
δ = 8.4375 (7.4); 7.5178 (1.0); 7.2590 (178.9); 7.2450 (1.3); 7.2358 (1.7); 7.2304 (0.8); 7.2218 (1.3); 7.0993 (0.5); 7.0807 (3.4); 7.0755 (2.8); 7.0666 (7.6); 6.9950 (1.0); 5.3459 (0.6); 5.2648 (1.0); 5.2446 (0.6); 2.6897 (1.0); 2.6748 (0.5); 2.6535 (0.6); 2.6388 (1.0); 2.6219 (0.7); 2.2451 (16.0); 2.0688 (0.7); 2.0577 (0.9); 2.0432 (0.9); 1.9719 (0.6); 1.9574 (0.8); 1.9417 (1.1); 1.9321 (1.6); 1.9272 (1.5); 1.9152 (2.2); 1.8989 (1.0); 1.8943 (0.9); 1.8891 (0.8); 1.6309 (9.3); 1.6235 (0.5); 1.5885 (56.3); 1.5437 (3.1); 0.0080 (2.3); −0.0002 (66.9); −0.0085 (2.0)
1.63: ¹H-NMR(400.0 MHz, CDCl3):
δ = 8.4402 (0.6); 8.3765 (16.0); 7.5181 (1.2); 7.2754 (0.5); 7.2738 (0.7); 7.2731 (0.7); 7.2714 (0.8); 7.2706 (0.9); 7.2699 (1.0); 7.2691 (1.1); 7.2682 (1.2); 7.2674 (1.4); 7.2666 (1.6); 7.2658 (1.9); 7.2592 (206.0); 7.1016 (1.6); 7.0830 (2.7); 7.0481 (3.0); 7.0301 (2.2); 7.0111 (1.2); 6.9952 (1.2); 5.2661 (0.6); 5.2431 (1.6); 5.2237 (2.5); 5.0354 (1.9); 5.0331 (2.4); 5.0301 (2.4); 5.0278 (2.0); 4.8654 (1.8); 4.8618 (2.3); 4.8600 (2.3); 4.8565 (1.8); 3.6658 (6.5); 3.0822 (1.1); 3.0628 (1.2); 3.0433 (1.2); 3.0244 (1.2); 2.5614 (0.8); 2.5390 (1.0); 2.5231 (0.7); 2.5005 (0.9); 2.3217 (0.6); 2.2943 (13.9); 2.2653 (0.7); 2.1159 (0.5); 2.1139 (0.7); 2.1123 (0.7); 2.1102 (0.6); 1.7272 (11.0); 1.7259 (11.2); 1.5953 (0.5); 1.5677 (45.8); 1.5426 (33.7); 1.2977 (13.6); 1.2808 (13.2); 0.0079 (3.3); 0.0063 (1.1); 0.0054 (1.2); 0.0046 (1.5); −0.0002 (108.8); −0.0051 (1.8); −0.0060 (1.4); −0.0068 (1.1); −0.0085 (3.1)
1.59: ¹H-NMR(400.0 MHz, CDCl3):
δ = 8.3390 (0.9); 7.2594 (13.0); 7.1483 (0.7); 7.1285 (1.6); 7.1086 (1.0); 6.9975 (1.4); 6.9781 (1.1); 6.7452 (1.3); 6.7256 (1.2); 3.8310 (16.0); 2.7131 (0.6); 2.6470 (0.6); 2.0300 (0.6); 1.9051 (0.5); 1.8897 (0.6); 1.8822 (0.7); 1.8783 (0.6); 1.8737 (0.8); 1.8646 (1.0); 1.8540 (1.0); 1.8471 (0.6); 1.7498 (1.4); 1.5607 (20.8); −0.0002 (5.5)

1.64: $^1$H-NMR(400.0 MHz, CDCl3):

δ = 8.4336 (1.0); 7.2659 (0.6); 7.2651 (0.6); 7.2643 (0.8); 7.2634 (0.9); 7.2626 (1.2); 7.2585 (67.0); 7.1628 (2.1); 7.1465 (4.8); 7.1453 (4.9); 7.0750 (2.2); 7.0733 (2.3); 7.0560 (1.4); 7.0539 (1.5); 5.6459 (0.6); 5.6267 (0.9); 5.5920 (0.9); 5.5738 (1.8); 5.5539 (1.4); 2.9710 (0.5); 2.9627 (0.8); 2.9538 (0.9); 2.9412 (0.8); 2.9323 (0.9); 2.8900 (0.6); 2.8700 (1.3); 2.8504 (1.0); 2.8311 (0.7); 2.7109 (0.8); 2.7018 (0.8); 2.6929 (1.0); 2.6915 (1.0); 2.6838 (1.0); 2.6823 (0.9); 2.6791 (1.0); 2.6734 (0.9); 2.6699 (0.9); 2.6641 (0.8); 2.6612 (1.0); 2.6597 (1.0); 2.6520 (1.0); 2.6417 (0.7); 2.6325 (0.6); 2.5831 (1.6); 2.3268 (16.0); 2.0434 (0.5); 1.9021 (0.5); 1.8994 (1.2); 1.8968 (0.9); 1.8889 (0.5); 1.8808 (0.9); 1.8782 (1.2); 1.8754 (0.6); 1.8704 (0.6); 1.8677 (1.1); 1.8650 (0.8); 1.8596 (0.5); 1.8570 (0.5); 1.8492 (0.8); 1.8465 (1.0); 1.7637 (12.7); 1.7613 (13.0); 1.5851 (2.6); 1.2648 (0.8); 0.8988 (0.5); 0.8818 (1.8); 0.8641 (0.7); 0.0079 (0.8); −0.0002 (26.6); −0.0085 (0.8)

1.62: $^1$H-NMR(400.0 MHz, CDCl3):

δ = 8.3508 (4.5); 7.2591 (25.0); 7.1019 (0.5); 7.0828 (0.9); 7.0498 (1.0); 7.0296 (0.7); 5.2495 (1.0); 5.2354 (0.6); 3.3086 (0.6); 3.2910 (2.2); 3.2735 (2.3); 3.2560 (0.7); 2.2948 (4.6); 1.5319 (16.0); 1.2977 (4.4); 1.2809 (4.3); 1.1911 (2.5); 1.1736 (5.5); 1.1561 (2.5); −0.0002 (9.9)

1.65: $^1$H-NMR(400.0 MHz, CDCl3):

δ = 8.4024 (2.7); 7.2594 (67.2); 7.1002 (1.1); 7.0804 (1.9); 7.0297 (5.0); 7.0120 (1.0); 5.2978 (1.7); 5.2612 (0.8); 5.2396 (1.3); 5.2175 (0.7); 4.3362 (2.5); 3.7029 (16.0); 3.7021 (15.9); 3.0858 (0.8); 3.0666 (0.9); 3.0472 (1.0); 3.0280 (1.0); 2.9383 (1.0); 2.9337 (1.0); 2.8978 (1.8); 2.8932 (1.8); 2.8065 (3.6); 2.7660 (2.0); 2.5580 (0.6); 2.5355 (0.8); 2.5205 (0.6); 2.4971 (0.7); 2.3130 (0.9); 2.2924 (10.8); 2.2786 (0.7); 1.5690 (10.7); 1.2849 (10.0); 1.2681 (9.9); 1.2583 (0.7); 0.8818 (0.8); 0.0080 (1.0); −0.0002 (28.2); −0.0085 (0.8)

1.66: $^1$H-NMR(400.0 MHz, CDCl3):

δ = 8.3830 (5.7); 7.2673 (0.5); 7.2665 (0.6); 7.2657 (0.7); 7.2649 (0.9); 7.2641 (1.1); 7.2600 (50.7); 7.2568 (1.2); 7.2559 (0.8); 7.2551 (0.6); 7.1047 (0.7); 7.0857 (1.1); 7.0431 (1.4); 7.0343 (1.0); 7.0155 (0.5); 5.2985 (2.2); 5.2607 (0.5); 5.2395 (0.7); 3.8994 (7.4); 3.7401 (14.3); 3.0279 (0.5); 2.2989 (5.7); 1.5899 (16.0); 1.2941 (5.4); 1.2773 (5.2); 0.0080 (0.7); −0.0002 (22.0); −0.0085 (0.6)

1.67: $^1$H-NMR(400.0 MHz, CDCl3):

δ = 8.4794 (1.9); 7.5179 (1.0); 7.3493 (2.1); 7.3316 (3.2); 7.3134 (0.6); 7.2834 (2.0); 7.2698 (6.4); 7.2660 (7.8); 7.2591 (191.8); 7.2364 (2.8); 7.2316 (3.8); 7.2252 (2.4); 7.2142 (2.8); 7.1966 (1.1); 6.9951 (1.0); 5.7521 (0.7); 5.6411 (0.9); 5.6223 (2.2); 5.6033 (2.0); 5.5842 (0.7); 3.0673 (0.6); 3.0575 (0.8); 3.0454 (0.8); 3.0355 (0.8); 3.0273 (3.3); 3.0180 (1.5); 3.0054 (1.4); 2.9958 (3.3); 2.9495 (1.2); 2.9289 (2.2); 2.9083 (1.7); 2.8886 (1.1); 2.8692 (0.7); 2.7273 (0.9); 2.7179 (1.0); 2.7080 (1.2); 2.6994 (1.2); 2.6953 (1.3); 2.6891 (1.1); 2.6858 (1.2); 2.6797 (1.1); 2.6763 (1.4); 2.6674 (1.3); 2.6572 (1.0); 2.6479 (0.8); 2.4983 (6.0); 2.4858 (3.5); 1.9573 (0.7); 1.9360 (1.6); 1.9244 (0.8); 1.9166 (1.5); 1.9040 (1.5); 1.8965 (1.0); 1.8848 (1.5); 1.8633 (0.8); 1.8152 (0.7); 1.7781 (15.6); 1.7757 (16.0); 0.1563 (0.9); 0.0080 (2.2); −0.0002 (73.0); −0.0085 (2.9)

1.68: $^1$H-NMR(400.6 MHz, MeOD):

δ = 8.4334 (0.8); 7.1453 (0.7); 7.1254 (1.5); 7.1055 (0.9); 6.9084 (1.1); 6.9069 (1.1); 6.8890 (1.0); 6.8874 (0.9); 6.8163 (1.3); 6.7962 (1.1); 5.5108 (0.5); 5.2390 (0.6); 4.8818 (30.4); 3.8338 (16.0); 3.3395 (3.8); 3.3354 (7.5); 3.3313 (11.4); 3.3272 (7.7); 3.3230 (3.8); 2.7210 (0.6); 2.6776 (0.6); 2.5048 (0.8); 1.9897 (0.8); 1.7240 (5.5)

1.72: $^1$H-NMR(400.0 MHz, CDCl3):

δ = 8.3848 (4.4); 7.5184 (0.8); 7.2595 (145.6); 7.1057 (0.6); 7.0867 (1.0); 7.0447 (1.2); 7.0344 (0.9); 6.9955 (0.8); 5.2631 (0.5); 5.2439 (0.6); 3.9393 (3.8); 3.9332 (3.8); 2.3930 (0.9); 2.3870 (1.9); 2.3808 (0.9); 2.2980 (5.0); 1.5905 (14.6); 1.5374 (16.0); 1.2970 (4.4); 1.2802 (4.3); 0.0080 (1.6); −0.0002 (57.0); −0.0085 (2.1)

1.69: $^1$H-NMR(400.0 MHz, CDCl3):

δ = 8.4628 (1.4); 7.5181 (1.2); 7.3879 (0.5); 7.3756 (0.6); 7.3594 (1.2); 7.3421 (1.2); 7.3385 (1.3); 7.3094 (0.6); 7.2592 (210.6); 7.2061 (0.6); 7.1932 (1.3); 7.1888 (1.4); 7.1757 (3.5); 7.1696 (3.8); 7.1566 (2.1); 7.1522 (1.5); 7.1315 (1.7); 7.1128 (0.8); 7.0893 (0.6); 6.9952 (1.2); 5.5015 (0.5); 5.2970 (0.7); 5.2791 (0.7); 2.8600 (0.6); 2.8442 (1.0); 2.8227 (0.8); 2.8074 (1.0); 2.7913 (0.9); 2.7757 (0.7); 2.7608 (0.7); 2.4946 (4.3); 2.3509 (2.8); 2.1362 (0.6); 2.1267 (0.6); 2.1154 (0.8); 2.1050 (0.7); 2.0897 (0.6); 1.9426 (0.9); 1.9359 (0.9); 1.9268 (1.1); 1.9105 (1.3); 1.8961 (1.6); 1.8852 (3.1); 1.8694 (0.7); 1.8456 (1.0); 1.8351 (1.2); 1.8223 (0.8); 1.7720 (8.6); 1.7697 (8.6); 1.5412 (16.0); 1.2583 (0.6); 0.0080 (2.8); −0.0002 (83.2); −0.0085 (3.0)

1.71: $^1$H-NMR(400.0 MHz, CDCl3):

δ = 8.4885 (3.3); 7.3280 (1.0); 7.3095 (1.3); 7.2584 (18.9); 7.2428 (2.5); 7.2398 (2.6); 7.2260 (1.7); 7.2051 (1.3); 7.1878 (0.9); 6.1458 (0.6); 6.1241 (0.6); 5.6742 (0.6); 5.6612 (0.7); 5.6524 (0.6); 5.6395 (0.6); 5.2957 (0.6); 4.2324 (0.8); 4.2276 (0.9); 4.2199 (1.2); 4.2151 (1.2); 4.2075 (0.8); 4.2027 (0.7); 3.4007 (0.9); 3.3843 (4.6); 3.3750 (16.0); 3.1585 (0.7); 3.1543 (0.7); 3.1174 (1.4); 3.1132 (1.4); 3.0386 (1.0); 3.0267 (1.0); 2.9974 (0.6); 2.9856 (0.5); 2.5060 (4.3); 1.7740 (6.9); 1.7722 (7.0); 1.2576 (1.0); −0.0002 (7.0)

1.70: $^1$H-NMR(400.0 MHz, CDCl3):

δ = 8.4651 (1.8); 7.5181 (1.5); 7.3077 (0.6); 7.2592 (262.8); 7.2348 (1.1); 7.2261 (1.7); 7.2126 (1.2); 7.2097 (1.1); 7.1097 (0.9); 7.1029 (1.0); 7.0900 (3.4); 7.0850 (3.4); 7.0760 (6.8); 7.0651 (0.9); 7.0443 (0.5); 6.9952 (1.6); 5.4931 (0.7); 5.4710 (0.8); 5.2982 (0.8); 5.2826 (0.9); 5.2625 (0.8); 3.0190 (0.8); 2.9342 (1.4); 2.7392 (0.6); 2.7113 (0.8); 2.6960 (1.2); 2.6814 (0.7); 2.6553 (2.9); 2.6414 (1.2); 2.6252 (0.9); 2.6145 (0.7); 2.5980 (0.7); 2.5850 (0.8); 2.3657 (1.3); 2.3496 (1.4); 2.2689 (1.0); 2.2477 (16.0); 2.2331 (1.6); 2.2149 (3.8); 2.0723 (0.9); 2.0613 (1.0); 2.0477 (0.8); 2.0315 (0.7); 2.0181 (0.6); 1.9537 (0.9); 1.9445 (1.3); 1.9397 (1.6); 1.9293 (2.2); 1.9180 (2.0); 1.9026 (1.5); 1.8835 (0.9); 1.8623 (0.9); 1.8347 (0.8); 1.7701 (9.6); 1.7682 (9.6); 1.5451 (9.8); 1.3441 (0.6); 1.3329 (0.6); 1.3261 (0.6); 1.2843 (1.1); 1.2557 (4.7); 0.8800 (0.8); 0.0079 (3.1); −0.0002 (101.2); −0.0085 (3.8)

1.73: $^1$H-NMR(400.0 MHz, CDCl3):

δ = 8.5035 (3.9); 7.2591 (33.2); 7.0974 (0.6); 7.0784 (0.8); 7.0058 (0.6); 6.7736 (0.9); 5.1087 (0.5); 5.1045 (0.6); 5.0656 (1.1); 5.0615 (1.1); 5.0398 (0.6); 5.0357 (0.5); 2.5337 (0.6); 2.2691 (4.3); 1.6276 (2.5); 1.6044 (16.0); 1.5420 (11.5); 1.2384 (2.8); 1.2225 (2.7); −0.0002 (12.5)

-continued 1.80: $^1$H-NMR(400.0 MHz, CDCl3):
δ = 8.3655 (1.7); 7.2585 (56.6); 7.1094 (1.8); 7.0892 (3.1); 7.0370 (4.8); 7.0230 (1.8); 5.4801 (0.8); 5.2785 (1.3); 5.2569 (2.2); 5.2348 (1.1); 4.9181 (1.5); 4.9016 (1.5); 4.8849 (0.5); 3.0899 (1.2); 3.0707 (1.3); 3.0516 (1.4); 3.0321 (1.5); 2.8298 (0.7); 2.5652 (1.0); 2.5429 (1.1); 2.5266 (0.8); 2.5047 (1.0); 2.3263 (0.6); 2.2993 (16.0); 2.2735 (0.9); 2.0435 (2.1); 1.5732 (3.2); 1.2898 (8.8); 1.2878 (9.0); 1.2730 (9.1); 1.2709 (9.4); 1.2585 (2.4); 1.2406 (0.8); 0.8988 (1.0); 0.8819 (3.1); 0.8642 (1.3); 0.0079 (0.6); −0.0002 (19.8); −0.0084 (0.8)

1.74: $^1$H-NMR(400.0 MHz, CDCl3):
δ = 8.5753 (1.2); 7.2586 (48.1); 7.1049 (1.4); 7.0857 (2.3); 7.0369 (5.3); 7.0180 (1.2); 5.4580 (0.7); 5.4394 (0.8); 5.2918 (1.1); 5.2699 (1.8); 5.2479 (0.8); 3.3592 (1.6); 3.0893 (1.0); 3.0701 (1.0); 3.0508 (1.1); 3.0314 (1.2); 2.5661 (0.8); 2.5440 (0.9); 2.5278 (0.7); 2.5052 (0.8); 2.2990 (11.4); 2.2750 (0.7); 1.9657 (16.0); 1.5765 (3.2); 1.2942 (6.4); 1.2894 (6.3); 1.2774 (6.5); 1.2726 (6.4); 0.8987 (0.7); 0.8818 (2.2); 0.8641 (0.9); 0.0079 (0.6); −0.0002 (18.0); −0.0085 (0.6)

1.75: $^1$H-NMR(400.0 MHz, CDCl3):
δ = 8.5878 (1.2); 7.5177 (0.6); 7.2588 (95.9); 7.1096 (1.6); 7.0895 (2.9); 7.0402 (7.0); 7.0233 (1.6); 6.9949 (0.6); 5.4866 (0.8); 5.4643 (1.0); 5.2951 (1.3); 5.2738 (2.1); 5.2516 (1.0); 3.4218 (1.8); 3.0947 (1.2); 3.0754 (1.3); 3.0561 (1.4); 3.0369 (1.4); 2.8691 (8.1); 2.5686 (1.0); 2.5464 (1.2); 2.5310 (0.8); 2.5082 (1.0); 2.3197 (1.1); 2.3018 (16.0); 2.2823 (0.9); 1.5616 (3.8); 1.2939 (8.7); 1.2906 (7.5); 1.2771 (8.8); 1.2738 (7.5); 0.8987 (0.6); 0.8818 (2.0); 0.8641 (0.8); 0.0079 (1.2); −0.0002 (37.3); −0.0085 (1.5)

1.78: $^1$H-NMR(400.0 MHz, CDCl3):
δ = 8.3203 (2.8); 7.5178 (0.7); 7.2589 (122.1); 7.1112 (1.6); 7.0921 (2.8); 7.0451 (5.9); 7.0253 (1.4); 6.9948 (0.7); 5.4578 (0.8); 5.4344 (1.1); 5.2816 (1.3); 5.2601 (2.0); 5.2378 (1.0); 4.3960 (0.8); 4.3795 (2.6); 4.3631 (2.7); 4.3466 (0.9); 3.4804 (12.8); 3.4768 (12.0); 3.0960 (1.1); 3.0769 (1.2); 3.0580 (1.3); 3.0386 (1.4); 2.5698 (0.9); 2.5472 (1.1); 2.5331 (0.8); 2.5089 (1.0); 2.3396 (0.5); 2.3194 (1.0); 2.3031 (16.0); 2.2832 (0.9); 1.5509 (10.1); 1.2973 (7.8); 1.2945 (8.3); 1.2805 (7.6); 1.2777 (8.0); 0.0080 (1.5); −0.0002 (44.6); −0.0085 (1.6)

1.77: $^1$H-NMR(400.0 MHz, CDCl3):
δ = 8.4334 (5.4); 7.3338 (5.0); 7.3227 (8.4); 7.2780 (0.6); 7.2662 (0.9); 7.2576 (28.4); 7.2488 (0.6); 7.1028 (0.8); 7.0838 (1.2); 7.0570 (1.5); 7.0305 (1.0); 7.0111 (0.6); 5.2669 (1.0); 5.2472 (0.8); 4.3115 (5.9); 3.0650 (0.5); 3.0457 (0.6); 3.0265 (0.6); 2.2935 (6.5); 1.6348 (16.0); 1.5671 (1.1); 3.3017 (5.4); 1.2849 (5.3); −0.0002 (10.7)

1.76: $^1$H-NMR(400.0 MHz, CDCl3):
δ = 8.3649 (5.8); 7.2593 (31.7); 7.1015 (0.6); 7.0826 (1.0); 7.0466 (1.2); 7.0296 (0.8); 5.2423 (1.0); 5.2313 (3.3); 3.0828 (0.5); 3.0596 (1.5); 3.0520 (3.3); 3.0425 (1.8); 3.0350 (1.3); 3.0243 (0.5); 2.2954 (5.4); 1.5640 (1.3); 1.5354 (16.0); 1.2976 (4.7); 1.2808 (4.6); 0.5322 (1.1); 0.5290 (1.2); 0.5238 (0.6); 0.5177 (0.6); 0.5121 (1.2); 0.5089 (1.1); 0.1409 (1.4); 0.1381 (1.3); 0.1289 (1.2); 0.1260 (1.4); −0.0002 (12.2)

1.79: $^1$H-NMR(400.0 MHz, CDCl3):
δ = 8.2853 (1.0); 7.2586 (61.9); 7.0982 (1.8); 7.0792 (3.0); 7.0449 (2.9); 7.0290 (2.6); 7.0097 (1.4); 5.2973 (1.0); 5.2539 (2.0); 3.0791 (1.1); 3.0597 (1.2); 3.0404 (1.3); 3.0213 (1.4); 2.6089 (16.0); 2.5572 (1.0); 2.5345 (1.2); 2.5187 (0.8); 2.4962 (1.0); 2.3617 (2.6); 2.3178 (0.5); 2.2965 (15.2); 2.2736 (0.8); 2.2707 (0.9); 2.2537 (0.6); 2.2512 (0.6); 1.8448 (11.7); 1.5654 (2.0); 1.2863 (12.0); 1.2695 (11.6); 1.2556 (0.6); 0.0080 (1.2); −0.0002 (36.9); −0.0085 (1.3)

1.81: $^1$H-NMR(400.0 MHz, CDCl3):
δ = 7.2592 (45.7); 7.1515 (0.7); 7.1454 (0.7); 7.1317 (1.6); 7.1258 (1.4); 7.1118 (0.9); 7.1059 (0.9); 6.9873 (1.0); 6.9678 (0.8); 6.9461 (1.4); 6.9266 (1.2); 6.7551 (1.4); 6.7402 (1.3); 6.7356 (1.3); 6.7216 (1.0); 3.8317 (16.0); 3.8274 (14.0); 2.7119 (1.0); 2.6962 (1.0); 2.6680 (1.1); 2.6525 (1.2); 2.6362 (0.7); 2.6125 (1.7); 2.5909 (2.9); 2.5081 (1.8); 2.4837 (1.0); 2.3920 (1.2); 2.0629 (0.6); 2.0514 (0.7); 2.0427 (0.6); 2.0393 (0.7); 1.9136 (0.7); 1.8990 (1.2); 1.8832 (1.8); 1.8741 (2.1); 1.8598 (1.4); 1.8442 (0.6); 1.8289 (5.0); 1.8273 (5.0); 1.5720 (3.4); 1.2650 (1.2); 0.8986 (0.6); 0.8818 (1.9); 0.8641 (0.8); 0.0078 (0.5); −0.0002 (16.8); −0.0084 (0.7)

1.82: $^1$H-NMR(400.0 MHz, CDCl3):
δ = 8.4321 (2.9); 7.7582 (0.7); 7.7553 (0.8); 7.7394 (0.8); 7.7360 (0.8); 7.5572 (0.7); 7.5372 (0.7); 7.2595 (92.5); 7.2222 (0.7); 7.2029 (1.1); 7.1835 (0.5); 6.9955 (0.5); 3.8876 (11.2); 3.8742 (0.7); 1.8994 (0.6); 1.8876 (0.8); 1.8772 (0.7); 1.6640 (2.9); 1.6111 (0.5); 1.5908 (16.0); 1.5441 (4.3); 0.0080 (1.0); −0.0002 (32.9); −0.0085 (1.2)

1.84: $^1$H-NMR(400.0 MHz, CDCl3):
δ = 8.4265 (0.6); 7.7646 (1.1); 7.7614 (1.1); 7.7454 (1.2); 7.7422 (1.2); 7.5454 (1.0); 7.5265 (1.2); 7.5184 (0.7); 7.2595 (102.1); 7.2351 (1.0); 7.2154 (1.8); 7.1961 (0.7); 6.9955 (0.6); 5.3360 (0.5); 5.3160 (0.5); 3.8910 (16.0); 3.0571 (0.7); 2.4379 (1.6); 2.4197 (1.6); 2.0814 (0.6); 1.9311 (0.5); 1.9146 (0.5); 1.8871 (1.2); 1.8775 (1.0); 1.8598 (0.6); 1.7663 (6.1); 1.5446 (4.5); 0.0079 (1.1); −0.0002 (39.0); −0.0085 (1.7)

1.96: $^1$H-NMR(400.0 MHz, CDCl3):
δ = 8.2866 (1.2); 7.2577 (19.8); 7.1700 (5.2); 7.1621 (4.4); 7.0905 (3.2); 7.0710 (2.0); 5.5900 (1.0); 5.5722 (1.1); 5.3875 (1.6); 5.3663 (1.3); 2.9969 (0.6); 2.9882 (0.7); 2.9750 (0.7); 2.9660 (0.8); 2.9577 (1.3); 2.9489 (1.3); 2.9359 (1.3); 2.9274 (1.3); 2.8877 (1.0); 2.8675 (2.0); 2.8475 (1.5); 2.8282 (1.0); 2.8077 (0.6); 2.7111 (0.8); 2.7023 (0.9); 2.6922 (1.3); 2.6833 (1.4); 2.6799 (1.3); 2.6708 (1.3); 2.6607 (1.7); 2.6485 (2.6); 2.6420 (1.7); 2.6290 (6.1); 2.6075 (15.6); 2.5916 (2.7); 2.5241 (2.9); 1.9041 (0.7); 1.8830 (1.6); 1.8725 (1.0); 1.8634 (1.8); 1.8511 (2.3); 1.8345 (16.0); 1.8106 (0.6); 1.6081 (1.0); 1.2547 (0.6); 1.2279 (7.8); 1.2090 (15.3); 1.1899 (7.2); −0.0002 (11.6)

1.95: $^1$H-NMR(400.0 MHz, CDCl3):
δ = 8.2717 (0.8); 7.3554 (2.2); 7.3374 (2.7); 7.2582 (50.7); 7.1950 (0.7); 7.1910 (0.9); 7.1772 (2.7); 7.1728 (2.9); 7.1597 (5.8); 7.1540 (5.8); 7.1403 (2.4); 7.1356 (3.1); 7.1167 (3.8); 7.1116 (2.9); 7.0975 (1.8); 7.0947 (1.8); 5.3726 (1.3); 5.2963 (2.2); 2.8735 (0.7); 2.8469 (1.8); 2.8313 (2.2); 2.8136 (1.7); 2.7972 (2.0); 2.7808 (1.3); 2.7553 (0.6); 2.5914 (10.6); 2.4817 (1.9); 2.4653 (2.0); 2.1688 (0.9); 2.1340 (0.9); 2.1209 (0.8); 2.1113 (1.2); 2.1001 (1.7); 2.0888 (1.1); 2.0739 (0.8); 2.0024 (1.3); 1.9421 (1.1); 1.9379 (1.2); 1.9316 (1.2); 1.9224 (2.0); 1.9151 (2.2); 1.9066 (3.1); 1.9014 (2.1); 1.8903 (4.0); 1.8756 (3.9); 1.8693 (2.0); 1.8594 (1.5); 1.8518 (1.2); 1.8271 (16.0); 1.5945 (1.5); 1.2547 (0.6); 0.0080 (1.2); −0.0002 (29.7); −0.0085 (1.0)

1.93: ¹H-NMR(400.0 MHz, CDCl3):
δ = 7.2575 (20.8); 7.2312 (0.9); 7.2214 (1.3); 7.2085 (1.1); 7.0725 (3.5); 7.0686 (3.2); 7.0590 (6.8); 5.3867 (0.7); 5.3663 (0.9); 5.2957 (1.8); 5.2861 (0.6); 2.6961 (0.5); 2.6800 (1.0); 2.6655 (0.6); 2.6492 (0.6); 2.6344 (1.1); 2.6179 (0.9); 2.5864 (5.4); 2.5239 (1.7); 2.2393 (16.0); 2.0584 (0.7); 2.0470 (0.8); 2.0322 (0.6); 2.0020 (1.6); 1.9651 (0.6); 1.9507 (0.7); 1.9480 (0.8); 1.9429 (0.5); 1.9346 (1.1); 1.9236 (1.7); 1.9185 (1.7); 1.9081 (2.2); 1.8923 (1.3); 1.8871 (0.9); 1.8803 (0.9); 1.8234 (9.2); 1.8217 (9.1); 1.6095 (0.6); −0.0002 (12.5)

1.92: ¹H-NMR(400.0 MHz, CDCl3):
δ = 8.2777 (0.5); 7.2581 (38.1); 7.1614 (3.0); 6.9971 (9.1); 5.3790 (0.8); 5.3592 (1.0); 5.2965 (3.6); 5.2446 (0.7); 2.7975 (0.8); 2.7818 (1.3); 2.7643 (0.9); 2.7469 (1.2); 2.7304 (0.8); 2.5942 (6.6); 2.4670 (1.6); 2.2673 (16.0); 2.1029 (0.5); 2.0923 (0.7); 2.0816 (1.0); 2.0705 (0.7); 2.0616 (0.6); 2.0540 (0.5); 1.9188 (0.8); 1.9054 (1.2); 1.8986 (1.2); 1.8834 (1.7); 1.8701 (1.8); 1.8660 (2.2); 1.8598 (1.5); 1.8503 (1.9); 1.8438 (1.4); 1.8302 (11.5); 1.5907 (1.2); 1.2549 (0.5); 0.0080 (0.8); −0.0002 (20.4); −0.0085 (0.6)

1.89: ¹H-NMR(400.0 MHz, CDCl3):
δ = 8.2942 (1.1); 7.2585 (39.3); 7.1425 (3.7); 7.1324 (3.3); 7.0596 (2.4); 7.0404 (1.6); 5.5871 (0.8); 5.5678 (0.8); 5.3496 (1.0); 5.3294 (0.8); 5.2971 (1.3); 2.9603 (0.6); 2.9516 (0.9); 2.9429 (1.0); 2.9298 (0.9); 2.9214 (1.0); 2.8815 (0.7); 2.8613 (1.4); 2.8412 (1.1); 2.8224 (0.7); 2.7018 (0.6); 2.6931 (0.6); 2.6832 (1.0); 2.6744 (1.0); 2.6704 (0.9); 2.6639 (0.8); 2.6615 (0.9); 2.6516 (1.2); 2.6428 (1.1); 2.6325 (0.9); 2.6234 (1.2); 2.6085 (10.8); 2.3882 (2.4); 2.3204 (16.0); 1.9007 (0.6); 1.8795 (1.3); 1.8690 (0.7); 1.8599 (1.5); 1.8386 (13.0); 1.8289 (1.9); 1.5735 (1.5); 1.2553 (0.5); 0.0078 (1.0); −0.0002 (22.4); −0.0084 (1.0)

1.90: ¹H-NMR(400.0 MHz, CDCl3):
δ = 8.2134 (1.8); 7.2588 (25.6); 7.0921 (0.9); 7.0731 (1.4); 7.0513 (1.5); 7.0183 (1.1); 6.9994 (0.7); 6.9951 (0.5); 5.2603 (0.7); 4.4168 (1.3); 4.4005 (1.4); 3.2759 (14.6); 3.2652 (0.6); 3.0698 (0.5); 3.0508 (0.6); 3.0314 (0.6); 3.0123 (0.6); 2.5304 (0.5); 2.3847 (16.0); 2.2894 (6.7); 2.2610 (0.6); 2.2591 (0.6); 1.4700 (7.0); 1.4537 (7.1); 1.2908 (4.0); 1.2874 (4.1); 1.2740 (4.1); 1.2706 (4.3); 0.8819 (1.6); 0.8641 (0.6); −0.0002 (12.7); −0.0084 (0.6)

1.88: ¹H-NMR(400.0 MHz, CDCl3):
δ = 8.2466 (1.8); 7.2586 (35.2); 7.0930 (1.1); 7.0740 (1.8); 7.0580 (1.9); 7.0191 (1.3); 7.0002 (0.8); 5.2583 (0.9); 5.2364 (0.6); 5.1411 (0.6); 4.9643 (1.6); 4.9033 (1.6); 4.5412 (1.5); 4.5249 (1.6); 3.8669 (0.7); 3.8357 (1.3); 3.7633 (1.5); 3.7316 (0.8); 3.0718 (0.6); 3.0527 (0.7); 3.0334 (0.7); 3.0143 (0.8); 2.5534 (0.5); 2.5312 (0.7); 2.4927 (0.5); 2.3741 (16.0); 2.2914 (8.4); 2.2638 (0.6); 1.7548 (7.4); 1.5715 (0.5); 1.4831 (7.4); 1.4668 (7.3); 1.2932 (4.6); 1.2905 (4.5); 1.2764 (4.6); 1.2737 (4.4); 0.0080 (0.5); −0.0002 (16.6); −0.0085 (0.7)

1.87: ¹H-NMR(400.0 MHz, CDCl3):
δ = 8.4043 (8.7); 8.4014 (8.8); 7.5182 (0.9); 7.2593 (165.4); 7.1029 (1.7); 7.0839 (2.8); 7.0439 (3.2); 7.0311 (2.7); 7.0113 (1.4); 6.9953 (1.0); 5.2498 (2.3); 5.2392 (2.9); 4.0461 (0.9); 4.0408 (1.2); 4.0335 (1.1); 4.0294 (1.1); 4.0241 (1.2); 4.0170 (1.0); 3.0826 (1.0); 3.0634 (1.1); 3.0438 (1.2); 3.0246 (1.4); 2.5629 (1.0); 2.5401 (1.1); 2.5258 (0.8); 2.5019 (1.0); 2.3481 (3.8); 2.3468 (4.0); 2.3431 (4.0); 2.3418 (3.8); 2.2945 (14.8); 1.6720 (9.4); 1.6685 (9.6); 1.6356 (0.6); 1.5680 (16.0); 1.5465 (15.5); 1.3971 (7.4); 1.3918 (7.5); 1.3805 (7.4); 1.3752 (7.4); 1.2967 (9.9); 1.2800 (9.8); 1.2568 (1.2); 0.0079 (2.4); −0.0002 (82.5); −0.0085 (3.1)

1.86: ¹H-NMR(400.0 MHz, CDCl3):
δ = 8.3711 (6.1); 7.2594 (25.2); 7.1036 (0.7); 7.0846 (1.2); 7.0458 (1.4); 7.0322 (1.0); 7.0131 (0.5); 5.2767 (0.6); 5.2611 (0.7); 5.2409 (0.7); 3.8963 (1.0); 3.8904 (2.9); 3.8845 (3.0); 3.8787 (1.0); 3.0452 (0.5); 3.0258 (0.5); 2.2975 (5.9); 1.8337 (3.2); 1.8278 (6.6); 1.8219 (3.2); 1.5706 (16.0); 1.2963 (4.9); 1.2795 (4.8); −0.0002 (13.0)

1.85: ¹H-NMR(599.7 MHz, CDCl3):
δ = 8.3656 (2.8); 8.3529 (9.8); 7.2594 (23.1); 7.0994 (3.3); 7.0867 (4.6); 7.0508 (4.6); 7.0271 (3.5); 7.0144 (2.4); 5.7274 (0.3); 5.7166 (1.0); 5.7146 (0.6); 5.7058 (1.1); 5.7038 (0.8); 5.6932 (1.0); 5.6912 (1.5); 5.6893 (0.8); 5.6823 (0.8); 5.6804 (1.5); 5.6785 (0.8); 5.6697 (0.5); 5.6026 (0.5); 5.6005 (0.4); 5.5914 (0.6); 5.5797 (0.8); 5.5770 (0.8); 5.5742 (0.4); 5.5719 (0.6); 5.5694 (1.5); 5.5667 (1.6); 5.5645 (0.8); 5.5622 (0.6); 5.5592 (0.8); 5.5565 (1.1); 5.5543 (1.2); 5.5516 (1.0); 5.5488 (0.5); 5.5465 (0.6); 5.5440 (1.3); 5.5413 (1.2); 5.5386 (0.6); 5.5362 (0.5); 5.5336 (0.8); 5.5310 (0.6); 5.2978 (1.4); 5.2823 (2.3); 5.2555 (2.1); 5.2414 (2.8); 5.2265 (1.1); 3.8280 (1.5); 3.8173 (1.6); 3.7020 (4.1); 3.6918 (4.1); 3.6910 (4.1); 3.0713 (1.9); 3.0585 (2.0); 3.0457 (2.1); 3.0329 (2.1); 2.5529 (1.5); 2.5376 (1.7); 2.5273 (1.4); 2.5121 (1.5); 2.3248 (0.4); 2.3082 (0.8); 2.2956 (20.5); 2.2820 (2.0); 2.2705 (1.3); 2.2688 (1.3); 2.2556 (0.7); 1.7030 (6.9); 1.7007 (7.1); 1.6922 (7.0); 1.6900 (7.0); 1.6044 (2.3); 1.6033 (2.3); 1.6020 (2.2); 1.5931 (2.5); 1.5920 (2.4); 1.5907 (2.6); 1.5848 (6.4); 1.5656 (13.7); 1.5493 (50.0); 1.2958 (15.8); 1.2846 (15.7); 1.2549 (0.4); 0.0698 (0.5); 0.0053 (0.7); −0.0001 (24.1); −0.0056 (0.9)

1.91: ¹H-NMR(400.0 MHz, CDCl3):
δ = 8.2461 (0.8); 8.2340 (2.2); 7.2589 (38.9); 7.0923 (1.5); 7.0733 (2.5); 7.0536 (2.6); 7.0186 (1.9); 6.9996 (1.2); 5.7079 (0.5); 5.6855 (0.9); 5.6698 (1.0); 5.6233 (0.5); 5.6202 (0.5); 5.6072 (0.9); 5.5929 (0.6); 5.5892 (0.6); 5.2808 (0.6); 5.2583 (1.2); 5.2365 (0.8); 5.1413 (1.0); 5.1194 (0.7); 4.5724 (0.9); 4.5560 (2.0); 4.5399 (1.7); 4.5236 (0.5); 3.9714 (0.7); 3.9549 (0.7); 3.8641 (0.8); 3.8611 (0.8); 3.8498 (0.8); 3.8470 (0.8); 3.8105 (0.8); 3.8081 (0.9); 3.7939 (0.9); 3.7917 (0.9); 3.0698 (0.8); 3.0507 (0.9); 3.0314 (1.0); 3.0122 (1.0); 2.5535 (0.8); 2.5302 (1.0); 2.5150 (0.7); 2.4921 (0.8); 2.3851 (4.3); 2.3729 (16.0); 2.3623 (1.5); 2.2906 (11.2); 2.2604 (0.9); 2.2416 (0.7); 1.7209 (3.9); 1.7184 (3.9); 1.7055 (3.9); 1.7027 (3.8); 1.6196 (1.0); 1.6041 (1.1); 1.5744 (0.7); 1.4805 (2.0); 1.4704 (7.3); 1.4643 (2.7); 1.4541 (7.2); 1.4334 (0.6); 1.2913 (6.0); 1.2887 (6.1); 1.2745 (6.4); 1.2719 (6.1); 1.2595 (1.4); 0.8817 (0.6); 0.0079 (0.8); −0.0002 (18.9); −0.0084 (0.9)

1.97: ¹H-NMR(400.0 MHz, CDCl3):
δ = 8.2579 (0.8); 7.5205 (0.7); 7.2617 (126.1); 7.2113 (0.6); 7.0870 (1.8); 7.0676 (3.0); 7.0149 (3.5); 6.9975 (2.8); 5.2395 (1.0); 3.7098 (16.0); 3.6994 (5.7); 3.0617 (1.4); 3.0424 (1.4); 3.0233 (1.5); 3.0040 (1.4); 2.7935 (0.7); 2.7540 (0.6); 2.6102 (15.7); 2.5436 (0.9); 2.5201 (1.1); 2.5040 (0.8); 2.4807 (0.9); 2.2834 (12.3); 2.2556 (1.1); 2.2364 (0.9); 2.0474 (1.6); 1.5948 (2.4); 1.5690 (4.9); 1.2606 (5.9); 0.8986 (1.2); 0.8819 (3.9); 0.8642 (1.6); 0.0080 (1.9); −0.0002 (66.7); −0.0084 (2.8)

1.83: $^1$H-NMR(400.0 MHz, CDCl3):
δ = 7.75 (1.5); 7.73 (1.1); 7.55 0.8); 7.53 (1.0); 3.89 (15.9); 3.16 (0.5); 3.14 (0.7); 3.06 (0.7); 2.63 (0.5); 2.60 (3.0); 2.51 (1.1); 2.375 (1.05); 2.37 (1.05); 1.84 (6.1)

B. Formulation Examples

A dusting product is obtained by mixing 10 parts by weight of a compound of the formula (I) and/or salts thereof and 90 parts by weight of talc as an inert substance, and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
 75 parts by weight of a compound of the formula (I) and/or salts thereof,
 10 parts by weight of calcium lignosulfonate,
 5 parts by weight of sodium lauryl sulfate,
 3 parts by weight of polyvinyl alcohol and
 7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting, in a colloid mill,
 25 parts by weight of a compound of the formula (I) and/or salts thereof,
 5 parts by weight of sodium 2,2'-dinaphthylmethane-6,6'-disulfonate
 2 parts by weight of sodium oleoylmethyltaurate,
 1 part by weight of polyvinyl alcohol,
 17 parts by weight of calcium carbonate and
 50 parts by weight of water,
then grinding the mixture in a bead mill and atomizing and drying the resulting suspension in a spray tower by means of a one-phase nozzle.

C. Biological Examples

Test Description

1. Pre-Emergence Herbicidal Effect and Crop Plant Compatibility

Seeds of monocotyledonous and dicotyledonous weed plants and crop plants are placed in plastic or wood fiber pots and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600 l/ha (converted).

After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

In the tables below, the following abbreviations are used:
Undesired plants/weeds:

| | |
|---|---|
| ABUTH: *Abutilon theophrasti* | ALOMY: *Alopecurus myosuroides* |
| AMARE: *Amaranthus retroflexus* | AVEFA: *Avena fatua* |
| ECHCG: *Echinochloa crus-galli* | HORMU: *Hordeum murinum* |
| LOLRI: *Lolium rigidum* | MATIN: *Matricaria inodora* |
| PHBPU: *Ipomoea purpurea* | POLCO: *Polygonum convolvulus* |
| SETVI: *Setaria viridis* | STEME: *Stellaria media* |
| VERPE: *Veronica persica* | VIOTR: *Viola tricolor* |

TABLE 6

Pre-emergence activity (herbicidal action against [%])

| Example number | Dosage | ALOMY | AVEFA | ECHCG | LOLRI | SETVI | ABUTH | AMARE |
|---|---|---|---|---|---|---|---|---|
| 1.4 | 320 | 100 | 100 | 100 | 100 | 100 | 100 | 100 |
| 1.53 | 320 | 100 | 100 | 100 | 90 | 100 | 100 | 100 |
| 1.5 | 320 | 100 | 100 | 100 | 100 | 100 | 100 | 100 |
| 1.57 | 320 | 100 | 100 | 100 | 100 | 100 | 100 | 100 |
| 1.55 | 320 | 90 | 100 | 100 | 100 | 100 | 100 | 100 |
| 1.61 | 320 | 100 | 80 | 100 | 100 | 100 | 100 | 100 |
| 1.24 | 320 | 100 | 100 | 100 | 100 | 100 | 100 | 100 |
| 1.54 | 320 | 100 | 80 | 100 | 100 | 100 | 100 | 100 |
| 1.48 | 320 | 100 | 90 | 100 | 100 | 100 | 100 | 100 |
| 1.63 | 320 | 100 | 90 | 100 | 100 | 100 | 100 | 100 |
| 1.14 | 320 | 100 | 100 | 100 | 100 | 100 | 100 | 100 |
| 1.15 | 320 | 100 | 100 | 100 | 100 | 100 | 100 | 100 |
| 1.31 | 320 | 100 | 100 | 100 | 100 | 100 | 100 | 100 |
| 1.50 | 320 | 100 | 100 | 100 | 100 | 100 | 100 | 100 |

TABLE 6-continued

Pre-emergence activity (herbicidal action against [%])

| | | | | | | | | |
|---|---|---|---|---|---|---|---|---|
| 1.18 | 320 | 100 | 100 | 100 | 100 | 100 | 100 | 100 |
| 1.43 | 320 | 100 | 100 | 100 | 100 | 100 | 100 | 100 |
| 1.51 | 320 | 100 | 80 | 100 | 100 | 100 | 100 | 100 |
| 1.52 | 320 | 100 | 100 | 100 | 100 | 100 | 100 | 100 |
| 1.6 | 320 | 100 | 100 | 100 | 100 | 100 | 100 | 100 |
| 1.7 | 320 | 100 | 90 | 100 | 100 | 100 | 100 | 100 |
| 1.8 | 320 | 100 | 100 | 100 | 100 | 100 | 100 | 100 |
| 1.22 | 320 | 100 | 100 | 100 | 100 | 100 | 100 | 100 |
| 1.11 | 320 | 100 | 100 | 100 | 100 | 100 | 100 | 100 |
| 1.10 | 320 | 100 | 100 | 100 | 100 | 100 | 100 | 100 |
| 1.12 | 320 | 100 | 100 | 100 | 100 | 100 | 100 | 100 |
| 1.13 | 320 | 100 | 100 | 100 | 100 | 100 | 100 | 100 |
| 1.17 | 320 | 100 | 100 | 100 | 100 | 100 | 100 | 100 |
| 1.23 | 320 | 100 | 100 | 100 | 100 | 100 | 100 | 100 |
| 1.20 | 320 | 100 | 100 | 100 | 100 | 100 | 100 | 100 |

| Example number | MATIN | PHBPU | POLCO | STEME | VIOTR | VERPE | HORMU |
|---|---|---|---|---|---|---|---|
| 1.4 | 100 | 100 | 100 | 100 | 100 | 100 | 100 |
| 1.53 | 100 | 100 | 100 | 100 | 100 | 100 | 100 |
| 1.5 | 100 | 100 | 100 | 100 | 100 | 100 | 100 |
| 1.57 | 100 | 100 | 100 | 100 | 100 | 100 | 100 |
| 1.55 | 100 | 90 | 100 | 100 | 100 | 100 | 100 |
| 1.61 | 100 | 90 | 100 | 100 | 100 | 100 | 100 |
| 1.24 | 100 | 90 | 100 | 100 | 100 | 100 | 100 |
| 1.54 | 100 | 100 | 100 | 100 | 100 | 100 | 100 |
| 1.48 | 100 | 90 | 100 | 100 | 100 | 100 | 100 |
| 1.63 | 100 | 100 | 100 | 100 | 100 | 100 | 90 |
| 1.14 | 100 | 100 | 100 | 100 | 100 | 100 | 100 |
| 1.15 | 100 | 100 | 100 | 100 | 100 | 100 | 100 |
| 1.31 | 100 | 100 | 100 | 100 | 100 | 100 | 100 |
| 1.50 | 100 | 100 | 100 | 100 | 100 | 100 | 90 |
| 1.18 | 100 | 100 | 100 | 100 | 100 | 100 | 100 |
| 1.43 | 100 | 100 | 100 | 100 | 100 | 100 | 100 |
| 1.51 | 100 | 100 | 100 | 100 | 100 | 100 | 90 |
| 1.52 | 100 | 100 | 100 | 100 | 100 | 100 | 100 |
| 1.6 | 100 | 100 | 100 | 100 | 100 | 100 | 100 |
| 1.7 | 100 | 80 | 100 | 100 | 100 | 100 | 100 |
| 1.8 | 100 | 100 | 100 | 100 | 100 | 100 | 100 |
| 1.22 | 100 | 100 | 100 | 100 | 100 | 100 | 100 |
| 1.11 | 100 | 80 | 100 | 100 | 100 | 100 | 100 |
| 1.10 | 100 | 80 | 100 | 100 | 100 | 100 | 100 |
| 1.12 | 100 | 100 | 100 | 100 | 100 | 100 | 100 |
| 1.13 | 100 | 100 | 100 | 100 | 100 | 100 | 100 |
| 1.17 | 100 | 80 | 100 | 100 | 100 | 100 | 100 |
| 1.23 | 100 | 100 | 100 | 100 | 100 | 100 | 80 |
| 1.20 | 100 | 100 | 100 | 100 | 100 | 100 | 100 |

TABLE 7

Pre-emergence activity (herbicidal action against [%])

| Example number | Dosage | AMARE | MATIN | POLCO | VIOTR | VERPE |
|---|---|---|---|---|---|---|
| 1.58 | 320 | 100 | 100 | 100 | 100 | 100 |
| 1.38 | 320 | 100 | 100 | 100 | 100 | 100 |
| 1.30 | 320 | 100 | 100 | 100 | 100 | 100 |
| 1.16 | 320 | 100 | 100 | 100 | 100 | 100 |
| 1.19 | 320 | 100 | 100 | 100 | 100 | 100 |
| 1.27 | 320 | 100 | 100 | 100 | 100 | 100 |
| 1.25 | 320 | 100 | 100 | 100 | 100 | 100 |
| 1.49 | 320 | 100 | 100 | 100 | 100 | 100 |
| 1.41 | 320 | 100 | 100 | 100 | 100 | 100 |
| 1.28 | 320 | 100 | 100 | 100 | 100 | 100 |
| 1.21 | 320 | 100 | 100 | 100 | 100 | 100 |
| 1.44 | 320 | 100 | 100 | 100 | 100 | 100 |
| 1.9 | 320 | 100 | 100 | 100 | 100 | 100 |
| 1.26 | 320 | 100 | 100 | 100 | 100 | 100 |
| 1.2 | 320 | 100 | 100 | 100 | 100 | 100 |
| 1.3 | 320 | 100 | 100 | 80 | 100 | 100 |
| 1.47 | 320 | 100 | 100 | 100 | 100 | 100 |

As the results show, the compounds according to the invention of Table 6 and Table 7, in pre-emergence applications, have good herbicidal activity against harmful plants.

The compounds according to the invention, applied by the pre-emergence method, have very good activity (80% to 100% herbicidal activity) against harmful plants such as, for example, *Abutilon theophrasti, Alopecurus myosuroides, Amaranthus retroflexus, Avena fatua, Echinochloa crusgalli, Hordeum murinum, Lolium rigidum, Matricaria inodora, Ipomoea purpurea, Polygonum convolvulus, Setaria viridis, Stellaria media, Veronica persica* and *Viola tricolor* at an application rate of 0.32 kg of active substance or less per hectare. At the same time, inventive compounds leave Gramineae crops such as barley, wheat, rye, millet/sorghum, corn or rice virtually undamaged when applied pre-emergence, even at high active ingredient dosages. In addition, some substances are also harmless to dicotyledonous crops such as soya, cotton, oilseed rape, sugar beet or potatoes.

Some of the compounds according to the invention exhibit high selectivity and are therefore suitable for controlling unwanted vegetation in agricultural crops by the pre-emergence method.

2. Post-Emergence Herbicidal Effect and Crop Plant Compatibility

Seeds of monocotyledonous and dicotyledonous weeds and crop plants are placed in sandy loam in plastic or wood-fiber pots, covered with soil and cultivated in a greenhouse under controlled growth conditions, 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion with addition of 0.5% additive at a water application rate of 600 l/ha (converted). After the test plants had been kept in the greenhouse under optimum growth conditions for about 3 weeks, the activity of the preparations is rated visually in comparison to untreated controls. For example, 100% activity=the plants have died, 0% activity=like control plants.

nochloa crusgalli, Hordeum murinum, Lolium rigidum, Matricaria inodora, Ipomoea purpurea, Polygonum convolvulus, Setaria viridis, Stellaria media, Veronica persica and Viola tricolor at an application rate of 0.32 kg of active substance or less per hectare. At the same time, inventive compounds leave Gramineae crops such as barley, wheat, rye, millet/sorghum, corn or rice virtually undamaged when applied post-emergence, even at high active ingredient dosages. In addition, some substances are also harmless to dicotyledonous crops such as soya, cotton, oilseed rape, sugar beet or potatoes. Some of the compounds according to the invention have high selectivity and are therefore suitable for controlling unwanted vegetation in agricultural crops by the post-emergence method.

TABLE 8

Post-emergence activity (herbicidal action against [%])

| Example number | Dosage | ECHCG | SETVI | ABUTH | AMARE | STEME | VIOTR | VERPE |
|---|---|---|---|---|---|---|---|---|
| 1.31 | 320 | 100 | 90 | 90 | 100 | 100 | 90 | 90 |
| 1.57 | 320 | 100 | 90 | 90 | 100 | 90 | 90 | 90 |
| 1.12 | 320 | 100 | 100 | 90 | 90 | 100 | 80 | 90 |
| 1.5 | 320 | 100 | 90 | 100 | 100 | 100 | 90 | 90 |
| 1.55 | 320 | 100 | 100 | 90 | 90 | 90 | 90 | 90 |
| 1.14 | 320 | 100 | 90 | 90 | 100 | 100 | 90 | 90 |
| 1.43 | 320 | 100 | 90 | 90 | 90 | 100 | 90 | 90 |
| 1.52 | 320 | 100 | 80 | 90 | 90 | 100 | 90 | 90 |
| 1.50 | 320 | 100 | 90 | 80 | 90 | 100 | 90 | 90 |
| 1.6 | 320 | 100 | 100 | 90 | 100 | 100 | 90 | 80 |
| 1.7 | 320 | 100 | 100 | 80 | 100 | 100 | 90 | 90 |
| 1.8 | 320 | 100 | 100 | 90 | 100 | 100 | 90 | 90 |
| 1.48 | 320 | 100 | 90 | 80 | 90 | 90 | 80 | 90 |
| 1.11 | 320 | 100 | 100 | 90 | 100 | 100 | 90 | 90 |
| 1.18 | 320 | 100 | 90 | 90 | 90 | 100 | 90 | 100 |
| 1.63 | 320 | 100 | 100 | 90 | 100 | 90 | 90 | 90 |
| 1.15 | 320 | 100 | 80 | 90 | 90 | 100 | 80 | 90 |
| 1.10 | 320 | 100 | 80 | 90 | 90 | 100 | 90 | 90 |
| 1.38 | 320 | 100 | 90 | 90 | 100 | 100 | 90 | 90 |
| 1.2 | 320 | 100 | 90 | 80 | 100 | 100 | 80 | 90 |
| 1.54 | 320 | 100 | 80 | 80 | 90 | 90 | 90 | 90 |
| 1.58 | 320 | 100 | 90 | 90 | 90 | 90 | 90 | 90 |
| 1.24 | 320 | 100 | 90 | 90 | 90 | 100 | 90 | 90 |
| 1.30 | 320 | 100 | 90 | 90 | 100 | 100 | 90 | 80 |
| 1.22 | 320 | 100 | 100 | 90 | 90 | 90 | 90 | 90 |

TABLE 9

Post-emergence activity (herbicidal action against [%])

| Example number | Dosage | ECHCG | ABUTH | AMARE | STEME |
|---|---|---|---|---|---|
| 1.13 | 320 | 100 | 80 | 90 | 90 |
| 1.4 | 320 | 90 | 90 | 100 | 90 |
| 1.53 | 320 | 100 | 90 | 90 | 90 |
| 1.61 | 320 | 100 | 90 | 90 | 90 |
| 1.22 | 320 | 100 | 90 | 90 | 90 |
| 1.20 | 320 | 100 | 90 | 90 | 100 |
| 1.49 | 320 | 80 | 80 | 90 | 90 |
| 1.17 | 320 | 80 | 90 | 80 | 100 |

As the results show, the compounds according to the invention of Table 8 and Table 9, in post-emergence applications, have good herbicidal activity against harmful plants.

The compounds according to the invention, applied by the post-emergence method, have very good herbicidal activity (80% to 100% herbicidal activity) against harmful plants such as, for example, Abutilon theophrasti, Alopecurus myosuroides, Amaranthus retroflexus, Avena fatua, Echi-

The invention claimed is:
1. A compound of formula (I)

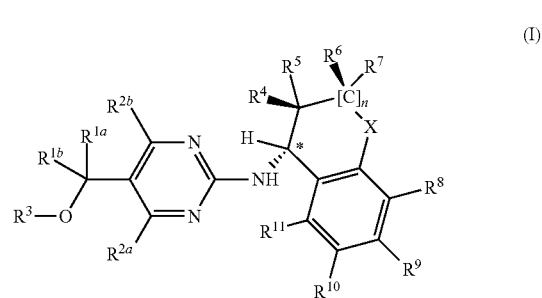

and/or an agrochemically acceptable salt thereof and/or an agrochemically acceptable quaternary nitrogen derivative thereof wherein $R^{1a}$ is selected from the group consisting of
hydrogen, cyano, C(O)OH, C(O)NH$_2$;
- ($C_1$-$C_6$)-alkyl, ($C_1$-$C_6$)-haloalkyl, ($C_1$-$C_6$)-alkylcarbonyl-($C_1$-$C_4$)-alkyl;
- ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
- ($C_2$-$C_6$)-alkenyl, ($C_2$-$C_6$)-haloalkenyl;
- ($C_2$-$C_6$)-alkynyl, ($C_2$-$C_6$)-haloalkynyl;
- ($C_6$-$C_{14}$)-aryl which may be substituted in the aryl moiety in each case by halogen, ($C_1$-$C_6$)-alkyl and/or ($C_1$-$C_6$)-haloalkyl;
- pyridyl which may in each case be substituted by halogen, ($C_1$-$C_6$)-alkyl and/or ($C_1$-$C_6$)-haloalkyl;
- thienyl which may in each case be substituted by halogen, ($C_1$-$C_6$)-alkyl and/or ($C_1$-$C_6$)-haloalkyl;
- ($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
- aminocarbonyl-($C_1$-$C_6$)-alkyl;
- ($C_1$-$C_6$)-alkoxy-($C_1$-$C_6$)-alkyl;
- ($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;
- ($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;
- hydroxy-($C_1$-$C_6$)-alkyl, amino-($C_1$-$C_6$)-alkyl, cyano-($C_1$-$C_6$)-alkyl;
- ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^{1b}$ is selected from the group consisting of
cyano, C(O)OH, C(O)NH$_2$;
- ($C_1$-$C_6$)-alkyl, ($C_1$-$C_6$)-haloalkyl, ($C_1$-$C_6$)-alkylcarbonyl-($C_1$-$C_4$)-alkyl;
- ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
- ($C_2$-$C_6$)-alkenyl, ($C_2$-$C_6$)-haloalkenyl;
- ($C_2$-$C_6$)-alkynyl, ($C_2$-$C_6$)-haloalkynyl;
- ($C_6$-$C_{14}$)-aryl which may be substituted in the aryl moiety in each case by halogen, ($C_1$-$C_6$)-alkyl and/or ($C_1$-$C_6$)-haloalkyl;
- pyridyl which may in each case be substituted by halogen, ($C_1$-$C_6$)-alkyl and/or ($C_1$-$C_6$)-haloalkyl;
- thienyl which may in each case be substituted by halogen, ($C_1$-$C_6$)-alkyl and/or ($C_1$-$C_6$)-haloalkyl;
- ($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
- aminocarbonyl-($C_1$-$C_6$)-alkyl;
- ($C_1$-$C_6$)-alkoxy-($C_1$-$C_6$)-alkyl;
- ($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;
- ($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;
- hydroxy-($C_1$-$C_6$)-alkyl, amino-($C_1$-$C_6$)-alkyl, cyano-($C_1$-$C_6$)-alkyl;
- ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^{2a}$ and $R^{2b}$ are in each case independently of one another selected from the group consisting of
hydrogen, halogen, hydroxyl, cyano, C(O)OH, C(O)NH$_2$;
- ($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;
- ($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
- ($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;
- ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;
- ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;
- ($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;
- aminocarbonyl-($C_1$-$C_6$)-alkyl, di-($C_1$-$C_6$)-alkylaminocarbonyl-($C_1$-$C_6$)-alkyl;
- N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;
- ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;
- ($C_3$-$C_8$)-cycloalkyl which is unsubstituted or mono- or polysubstituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio and ($C_3$-$C_6$)-alkynylthio;

$R^3$ is selected from the group consisting of hydrogen;

($C_1$-$C_6$)-alkylcarbonyl, ($C_1$-$C_6$)-haloalkylcarbonyl;

($C_2$-$C_6$)-alkenylcarbonyl, ($C_2$-$C_6$)-haloalkenylcarbonyl;

($C_2$-$C_6$)-alkynylcarbonyl, ($C_2$-$C_6$)-haloalkynylcarbonyl;

($C_6$-$C_{14}$)-arylcarbonyl which may in each case be substituted in the aryl moiety by halogen, ($C_1$-$C_6$)-alkyl and/or ($C_1$-$C_6$)-haloalkyl;

aminocarbonyl, [($C_1$-$C_6$)-alkylamino]carbonyl, [di-($C_1$-$C_6$)-alkylamino]carbonyl:

($C_1$-$C_6$)-alkoxycarbonyl, ($C_2$-$C_6$)-alkenyloxycarbonyl, ($C_2$-$C_6$)-alkynyloxycarbonyl;

($C_1$-$C_6$)-trialkylsilyl;

($C_1$-$C_6$)-alkylsulfonyl, ($C_1$-$C_6$)-haloalkylsulfonyl;

($C_6$-$C_{14}$)-arylsulfonyl which may in each case be substituted in the aryl moiety by halogen, ($C_1$-$C_6$)-alkyl and/or ($C_1$-$C_6$)-haloalkyl;

($C_1$-$C_6$)-alkyl, ($C_1$-$C_6$)-haloalkyl, ($C_1$-$C_6$)-alkylcarbonyl-($C_1$-$C_4$)-alkyl;

($C_2$-$C_6$)-alkenyl, ($C_2$-$C_6$)-haloalkenyl;

($C_2$-$C_6$)-alkynyl, ($C_2$-$C_6$)-haloalkynyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_6$-$C_{14}$)-aryl which may be substituted in the aryl moiety in each case by halogen, ($C_1$-$C_6$)-alkyl and/or ($C_1$-$C_6$)-haloalkyl;

($C_2$-$C_{14}$)-Het-aryl which may in each case be substituted in the Het-aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be mono- or polysubstituted in the cycloalkyl radical by ($C_1$-$C_6$)-alkyl and/or halogen;

($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl-($C_1$-$C_6$)-alkyl, ($C_3$-$C_8$)-cycloalkenyl-($C_1$-$C_6$)-haloalkyl, hydroxy-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^4$ and $R^5$ are each independently of one another selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or the radicals $R^4$ and $R^5$ together with the carbon atom to which they are attached form a three- to seven-membered ring;

$R^6$ and $R^7$ are each independently of one another selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the radicals $R^6$ and $R^7$ together form a ($C_1$-$C_7$)-alkylene group which may contain one or more oxygen and/or sulfur atoms, where the ($C_1$-$C_7$)-alkylene group may be mono- or polysubstituted by halogen and the respective halogen substituents may be identical or different;

n represents the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)- dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl, $(C_6-C_{14})$-aryl and nitro, where the $R^9$ and $R^{10}$ radicals may be attached to one another via an —O—CH$_2$—O— group forming a ring;

X represents a bond, CH$_2$, O, S, carbonyl, NH, $CR^{12}R^{13}$, $NR^{14}$, CH$_2$O or CH$_2$S, wherein with respect to CH$_2$O and CH$_2$S, the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl.

2. The compound according to claim 1, wherein
$R^{1a}$ is selected from the group consisting of
hydrogen, cyano;
$(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, and
$(C_3-C_8)$-cycloalkyl which may be unsubstituted or mono- or polysubstituted in the cycloalkyl radical by $(C_1-C_6)$-alkyl and/or halogen, $R^{1b}$ is selected from the group consisting of
cyano, C(O)OH, C(O)NH$_2$;
$(C_1-C_6)$-alkyl, $(C_1-C_6)$-haloalkyl, $(C_1-C_6)$-alkylcarbonyl-$(C_1-C_4)$-alkyl;
$(C_1-C_6)$-alkoxycarbonyl-$(C_1-C_6)$-alkyl, $(C_2-C_6)$-alkenyl, $(C_2-C_6)$-haloalkenyl;
$(C_2-C_6)$-alkynyl, $(C_2-C_6)$-haloalkynyl;
$(C_6-C_{14})$-aryl which may be substituted in the aryl moiety in each case by halogen, $(C_1-C_6)$-alkyl and/or $(C_1-C_6)$-haloalkyl;
pyridyl which may in each case be substituted by halogen, $(C_1-C_6)$-alkyl and/or $(C_1-C_6)$-haloalkyl;
thienyl which may in each case be substituted by halogen, $(C_1-C_6)$-alkyl and/or $(C_1-C_6)$-haloalkyl;
$(C_6-C_{14})$-aryl-$(C_1-C_6)$-alkyl which may in each case be substituted in the aryl moiety by halogen, $(C_1-C_6)$-alkyl and/or $(C_1-C_6)$-haloalkyl;
$(C_3-C_8)$-cycloalkyl which may be unsubstituted or mono- or polysubstituted in the cycloalkyl radical by $(C_1-C_6)$-alkyl and/or halogen; $(C_3-C_8)$-cycloalkyl-$(C_1-C_6)$-alkyl, $(C_3-C_8)$-cycloalkyl-$(C_1-C_6)$-haloalkyl;
$(C_3-C_8)$-cycloalkenyl, $(C_3-C_8)$-cycloalkenyl-$(C_1-C_6)$-alkyl, $(C_3-C_8)$-cycloalkenyl-$(C_1-C_6)$-haloalkyl;
cyano-$(C_1-C_6)$-alkyl;
$(C_1-C_6)$-alkylsulfonyl-$(C_1-C_6)$-alkyl, $(C_1-C_6)$-alkylthio-$(C_1-C_6)$-alkyl, and $(C_1-C_6)$-alkylsulfinyl-$(C_1-C_6)$-alkyl.

3. The compound according to claim 1, wherein
$R^{1a}$ is selected from the group consisting of
hydrogen;
$(C_1-C_3)$-alkyl, $(C_1-C_3)$-haloalkyl, $(C_2-C_3)$-alkenyl, and $(C_2-C_3)$-alkynyl,
$R^{1b}$ is selected from the group consisting of
cyano;
$(C_1-C_4)$-alkyl, $(C_1-C_4)$-haloalkyl;
$(C_1-C_3)$-alkoxycarbonylmethyl, $(C_2-C_4)$-alkenyl, $(C_2-C_4)$-haloalkenyl;
$(C_2-C_4)$-alkynyl, $(C_2-C_4)$-haloalkynyl;
phenyl which may be substituted in the aryl moiety by halogen and/or methyl;
CH$_2$-phenyl (benzyl) which may be substituted in the aryl moiety by halogen and/or methyl; and
$(C_3-C_6)$-cycloalkyl which may be unsubstituted or mono- or polysubstituted in the cycloalkyl radical by methyl and/or halogen.

4. The compound according to claim 1, wherein, if $R^{1a}$ does not represent hydrogen, $R^{1a}$ is linked to $R^{1b}$ via a bond so that, together with the carbon to which these two radicals are attached, a saturated 3- to 6-membered carbocycle is formed which is unsubstituted or is substituted by one or more substituents selected from the group consisting of methyl, trifluoromethyl, and cyclopropyl.

5. The compound according to claim 1, wherein $R^{2a}$ and $R^{2b}$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-alkoxy-$(C_1-C_6)$-alkyl, $(C_3-C_8)$-cycloalkyl, $(C_3-C_8)$-cycloalkyl-$(C_1-C_6)$-alkyl and $(C_3-C_8)$-cycloalkyl-$(C_1-C_6)$-haloalkyl, where the cycloalkyl radical is in each case unsubstituted or is substituted by $(C_1-C_6)$-alkyl and/or halogen.

6. The compound according to claim 1, wherein $R^3$ is selected from the group consisting of hydrogen, $(C_1-C_4)$-alkylcarbonyl, phenylcarbonyl (benzoyl), $(C_1-C_3)$-alkyl, CH$_2(C_2-C_3)$-alkenyl, CH(CH$_3$)(C$_2$-C$_3$)-alkenyl, CH$_2(C_2-C_3)$-alkynyl, CH(CH$_3$)(C$_2$-C$_3$)-alkynyl, $(C_1-C_3)$-alkoxycarbonylmethyl, CH$_2$-phenyl (benzyl), CH$_2$(4-F-phenyl) and Si(CH$_3$)$_3$.

7. The compound according to claim 1, wherein $R^3$ is selected from the group consisting of hydrogen, CH$_3$, CH$_2$CH$_3$, CH$_2$CH=CH$_2$, CH$_2$C(CH$_3$)=CH$_2$, CH$_2$CH=CHCH$_3$, CH$_2$C≡CH, CH$_2$C≡CCH$_3$, CH(CH$_3$)CH=CH$_2$, CH(CH$_3$)C≡CH and CH$_2$C(O)OCH$_3$.

8. The compound according to claim 1, wherein $R^4$ and $R^5$ are each independently of one another selected from the group consisting of hydrogen, hydroxy, $(C_1-C_6)$-alkyl, $(C_1-C_6)$-alkylphenyl and $(C_1-C_6)$-alkoxy.

9. The compound according to claim 1, wherein $R^6$ and $R^7$ are independently of one another selected from the group consisting of hydrogen, $(C_1-C_6)$-alkyl and $(C_6-C_{14})$-aryl.

10. The compound according to claim 1, wherein $R^8$ is selected from the group consisting of hydrogen, halogen, cyano, C(O)OH, $(C_1-C_6)$-alkyl, $(C_1-C_6)$-alkoxy, $(C_1-C_6)$-alkyloxycarbonyl and $(C_6-C_{14})$-aryl.

11. The compound according to claim 1, wherein $R^9$ is selected from the group consisting of hydrogen, halogen, $(C_1-C_6)$-alkyl and $(C_1-C_6)$-alkoxy.

12. The compound according to claim 1, wherein $R^{10}$ is selected from the group consisting of hydrogen, halogen, cyano, aminocarbonyl, hydroxycarbonyl, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl.

13. The compound according to claim 1, wherein $R^{11}$ is selected from the group consisting of hydrogen and $(C_1-C_6)$-alkyl.

14. The compound according to claim 1, wherein X is selected from the group consisting of a chemical bond, CH$_2$, o, S, carbonyl, NH, CH($C_1-C_6$)-alkyl, N($C_1-C_6$)-alkyl, OCH$_2$ and SCH$_2$, wherein with respect to OCH$_2$ and SCH$_2$, the carbon atom is attached to an aromatic moiety and the heteroatom O or S is attached to a partially hydrogenated moiety of the amine.

15. The compound according to claim 1, wherein $R^9$ and $R^{10}$ are linked via an —O—CH$_2$—O— group to form a ring.

16. The compound according to claim 1, wherein the running number n is 0 or 1.

17. The compound of formula (I)

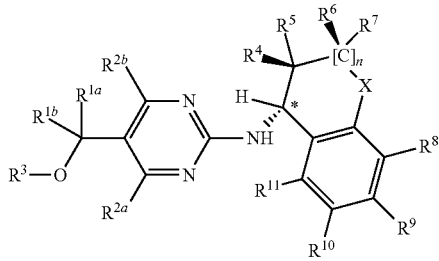
(I)

according to claim 1, wherein the chiral carbon atom marked by (*) has an (R) configuration.

18. The compound of formula (I)

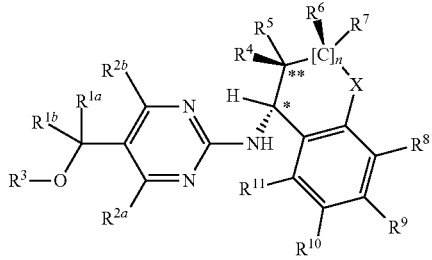
(I)

according to claim 1, wherein the chiral carbon atom marked by (*) has an (R) configuration and the chiral carbon atom marked by (**) has an (S) configuration.

19. A process for preparing a compound of formula (I) and/or an agrochemically acceptable salt thereof and/or an agrochemically acceptable quaternized nitrogen derivative thereof

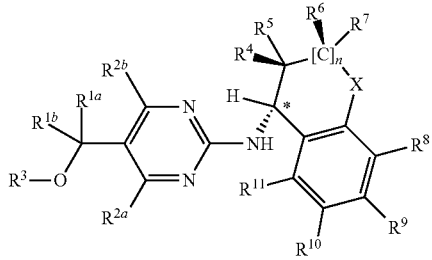
(I)

wherein
$R^{1a}$ is selected from the group consisting of
hydrogen, cyano, C(O)OH, C(O)NH$_2$;
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl;
($C_2$-$C_6$)-alkynyl, ($C_2$-$C_6$)-haloalkynyl;
($C_6$-$C_{14}$)-aryl which may be substituted in the aryl moiety in each case by halogen, ($C_1$-$C_6$)-alkyl and/or ($C_1$-$C_6$)-haloalkyl;
pyridyl which may in each case be substituted by halogen, ($C_1$-$C_6$)-alkyl and/or ($C_1$-$C_6$)-haloalkyl;
thienyl which may in each case be substituted by halogen, ($C_1$-$C_6$)-alkyl and/or ($C_1$-$C_6$)-haloalkyl;
($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
aminocarbonyl-($C_1$-$C_6$)-alkyl;
($C_1$-$C_6$)-alkoxy-($C_1$-$C_6$)-alkyl;
($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;
($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;
hydroxy-($C_1$-$C_6$)-alkyl, amino-($C_1$-$C_6$)-alkyl, cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;
$R^{1b}$ is selected from the group consisting of
cyano, C(O)OH, C(O)NH$_2$;
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl;
($C_2$-$C_6$)-alkynyl, ($C_2$-$C_6$)-haloalkynyl;
($C_6$-$C_{14}$)-aryl which may be substituted in the aryl moiety in each case by halogen, ($C_1$-$C_6$)-alkyl and/or ($C_1$-$C_6$)-haloalkyl;
pyridyl which may in each case be substituted by halogen, ($C_1$-$C_6$)-alkyl and/or ($C_1$-$C_6$)-haloalkyl;
thienyl which may in each case be substituted by halogen, ($C_1$-$C_6$)-alkyl and/or ($C_1$-$C_6$)-haloalkyl;
($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
aminocarbonyl-($C_1$-$C_6$)-alkyl;
($C_1$-$C_6$)-alkoxy-($C_1$-$C_6$)-alkyl;
($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;
($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;
hydroxy-($C_1$-$C_6$)-alkyl, amino-($C_1$-$C_6$)-alkyl, cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)- haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^{2a}$ and $R^{2b}$ are in each case independently of one another selected from the group consisting of hydrogen, halogen, hydroxyl, cyano, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

aminocarbonyl-($C_1$-$C_6$)-alkyl, di-($C_1$-$C_6$)-alkylaminocarbonyl-($C_1$-$C_6$)-alkyl;

N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which is unsubstituted or mono- or polysubstituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio and ($C_3$-$C_6$)-alkynylthio;

$R^3$ is selected from the group consisting of hydrogen;

($C_1$-$C_6$)-alkylcarbonyl, ($C_1$-$C_6$)-haloalkylcarbonyl;

($C_2$-$C_6$)-alkenylcarbonyl, ($C_2$-$C_6$)-haloalkenylcarbonyl;

($C_2$-$C_6$)-alkynylcarbonyl, ($C_2$-$C_6$)-haloalkynylcarbonyl;

($C_6$-$C_{14}$)-arylcarbonyl which may in each case be substituted in the aryl moiety by halogen, ($C_1$-$C_6$)-alkyl and/or ($C_1$-$C_6$)-haloalkyl;

aminocarbonyl, [($C_1$-$C_6$)-alkylamino]carbonyl, [di-($C_1$-$C_6$)-alkylamino]carbonyl:

($C_1$-$C_6$)-alkoxycarbonyl, ($C_2$-$C_6$)-alkenyloxycarbonyl, ($C_2$-$C_6$)-alkynyloxycarbonyl;

($C_1$-$C_6$)-trialkylsilyl;

($C_1$-$C_6$)-alkylsulfonyl, ($C_1$-$C_6$)-haloalkylsulfonyl;

($C_6$-$C_{14}$)-arylsulfonyl which may in each case be substituted in the aryl moiety by halogen, ($C_1$-$C_6$)-alkyl and/or ($C_1$-$C_6$)-haloalkyl;

($C_1$-$C_6$)-alkyl, ($C_1$-$C_6$)-haloalkyl, ($C_1$-$C_6$)-alkylcarbonyl-($C_1$-$C_4$)-alkyl;

($C_2$-$C_6$)-alkenyl, ($C_2$-$C_6$)-haloalkenyl;

($C_2$-$C_6$)-alkynyl, ($C_2$-$C_6$)-haloalkynyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_6$-$C_{14}$)-aryl which may be substituted in the aryl moiety in each case by halogen, ($C_1$-$C_6$)-alkyl and/or ($C_1$-$C_6$)-haloalkyl;

($C_2$-$C_{14}$)-Het-aryl which may in each case be substituted in the Het-aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;
aminocarbonyl-($C_1$-$C_6$)-alkyl;
($C_1$-$C_6$)-alkoxy-($C_1$-$C_6$)-alkyl;
($C_3$-$C_8$)-cycloalkyl which may be mono- or polysubstituted in the cycloalkyl radical by ($C_1$-$C_6$)-alkyl and/or halogen;
($C_3$-$C_8$)-cycloalkyl-($C_1$-$C_6$)-alkyl, ($C_3$-$C_8$)-cycloalkyl-($C_1$-$C_6$)-haloalkyl;
($C_3$-$C_8$)-cycloalkenyl-($C_1$-$C_6$)-alkyl, ($C_3$-$C_8$)-cycloalkenyl-($C_1$-$C_6$)-haloalkyl, hydroxy-($C_1$-$C_6$)-alkyl, cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;
$R^4$ and $R^5$ are each independently of one another selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or
the radicals $R^4$ and $R^5$ together with the carbon atom to which they are attached form a three- to seven-membered ring;
$R^6$ and $R^7$ are each independently of one another selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or
the radicals $R^6$ and $R^7$ together form a ($C_1$-$C_7$)-alkylene group which may contain one or more oxygen and/or sulfur atoms, where the ($C_1$-$C_7$)-alkylene group may be mono- or polysubstituted by halogen and the respective halogen substituents may be identical or different;
n represents the running number 0, 1 or 2;
$R^8$, $R^9$, $R^{10}$ and $R^{11}$ are each independently of one another selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-dialkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl, ($C_6$-$C_{14}$)-aryl and nitro, where the $R^9$ and $R^{10}$ radicals may be attached to one another via an —O—CH$_2$—O— group forming a ring;
X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;
$R^{12}$ and $R^{13}$ are each independently of one another selected from the group consisting of hydrogen, ($C_1$-$C_6$)-alkyl and ($C_1$-$C_6$)-haloalkyl; and
$R^{14}$ is selected from the group consisting of hydrogen, ($C_1$-$C_6$)-alkyl and ($C_1$-$C_6$)-haloalkyl,
said process comprising reacting a compound of formula (II)

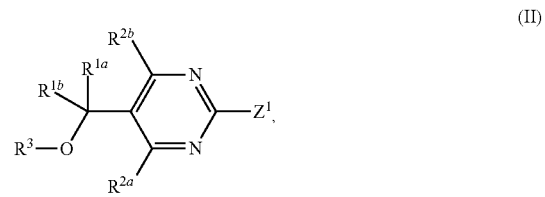

wherein $Z^1$ represents an exchangeable radical or a leaving group selected from the group consisting of fluorine, chlorine, bromine, iodine, ($C_1$-$C_4$)-alkylsulfanyl, ($C_1$-$C_4$)-alkylsulfinyl, ($C_1$-$C_4$)-alkylsulfonyl, unsubstituted phenyl-($C_1$-$C_4$)-alkylsulfonyl or phenyl-($C_1$-$C_4$)-alkylsulfonyl which is mono- or polysubstituted by fluorine, chlorine, bromine or ($C_1$-$C_4$)-alkyl or ($C_1$-$C_4$)-alkoxy, and ($C_1$-$C_4$)-alkylphenylsulfonyl;
with an amine of formula (III) and/or with an acid addition salt of an amine of formula (III)

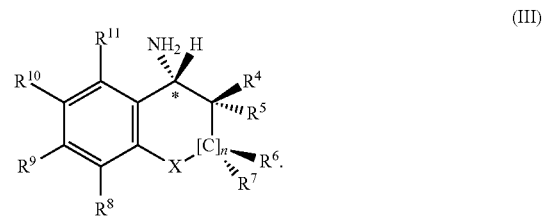

20. A process for preparing a compound of formula (I) and/or an agrochemically acceptable salt thereof and/or an agrochemically acceptable quaternized nitrogen derivative thereof

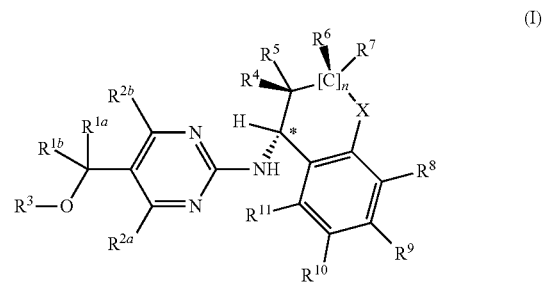

wherein
$R^{1a}$ is selected from the group consisting of
hydrogen, cyano, C(O)OH, C(O)NH$_2$;
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl;
($C_2$-$C_6$)-alkynyl, ($C_2$-$C_6$)-haloalkynyl;
($C_6$-$C_{14}$)-aryl which may be substituted in the aryl moiety in each case by halogen, ($C_1$-$C_6$)-alkyl and/or ($C_1$-$C_6$)-haloalkyl;

pyridyl which may in each case be substituted by halogen, $(C_1-C_6)$-alkyl and/or $(C_1-C_6)$-haloalkyl;
thienyl which may in each case be substituted by halogen, $(C_1-C_6)$-alkyl and/or $(C_1-C_6)$-haloalkyl;
$(C_6-C_{14})$-aryl-$(C_1-C_6)$-alkyl which may in each case be substituted in the aryl moiety by halogen, $(C_1-C_6)$-alkyl and/or $(C_1-C_6)$-haloalkyl;
aminocarbonyl-$(C_1-C_6)$-alkyl;
$(C_1-C_6)$-alkoxy-$(C_1-C_6)$-alkyl;
$(C_3-C_8)$-cycloalkyl which may be unsubstituted or mono- or polysubstituted in the cycloalkyl radical by $(C_1-C_6)$-alkyl and/or halogen; $(C_3-C_8)$-cycloalkyl-$(C_1-C_6)$-alkyl, $(C_3-C_8)$-cycloalkyl-$(C_1-C_6)$-haloalkyl;
$(C_3-C_8)$-cycloalkenyl, $(C_3-C_8)$-cycloalkenyl-$(C_1-C_6)$-alkyl, $(C_3-C_8)$-cycloalkenyl-$(C_1-C_6)$-haloalkyl;
hydroxy-$(C_1-C_6)$-alkyl, amino-$(C_1-C_6)$-alkyl, cyano-$(C_1-C_6)$-alkyl;
$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl;

$R^{1b}$ is selected from the group consisting of
cyano, $C(O)OH$, $C(O)NH_2$;
$(C_1-C_6)$-alkyl, $(C_1-C_6)$-haloalkyl, $(C_1-C_6)$-alkylcarbonyl-$(C_1-C_4)$-alkyl;
$(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
$(C_2-C_6)$-alkenyl, $(C_2-C_6)$-haloalkenyl;
$(C_2-C_6)$-alkynyl, $(C_2-C_6)$-haloalkynyl;
$(C_6-C_{14})$-aryl which may be substituted in the aryl moiety in each case by halogen, $(C_1-C_6)$-alkyl and/or $(C_1-C_6)$-haloalkyl;
pyridyl which may in each case be substituted by halogen, $(C_1-C_6)$-alkyl and/or $(C_1-C_6)$-haloalkyl;
thienyl which may in each case be substituted by halogen, $(C_1-C_6)$-alkyl and/or $(C_1-C_6)$-haloalkyl;
$(C_6-C_{14})$-aryl-$(C_1-C_6)$-alkyl which may in each case be substituted in the aryl moiety by halogen, $(C_1-C_6)$-alkyl and/or $(C_1-C_6)$-haloalkyl;
aminocarbonyl-$(C_1-C_6)$-alkyl;
$(C_1-C_6)$-alkoxy-$(C_1-C_6)$-alkyl;
$(C_3-C_8)$-cycloalkyl which may be unsubstituted or mono- or polysubstituted in the cycloalkyl radical by $(C_1-C_6)$-alkyl and/or halogen; $(C_3-C_8)$-cycloalkyl-$(C_1-C_6)$-alkyl, $(C_3-C_8)$-cycloalkyl-$(C_1-C_6)$-haloalkyl;
$(C_3-C_8)$-cycloalkenyl, $(C_3-C_8)$-cycloalkenyl-$(C_1-C_6)$-alkyl, $(C_3-C_8)$-cycloalkenyl-$(C_1-C_6)$-haloalkyl;
hydroxy-$(C_1-C_6)$-alkyl, amino-$(C_1-C_6)$-alkyl, cyano-$(C_1-C_6)$-alkyl;
$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl;

$R^{2a}$ and $R^{2b}$ are in each case independently of one another selected from the group consisting of
hydrogen, halogen, hydroxyl, cyano, $C(O)OH$, $C(O)NH_2$;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl;
$(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
$(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl, $(C_2-C_6)$-haloalkenyloxycarbonyl;
$(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl; tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;
$(C_6-C_{14})$-aryl, $(C_6-C_{14})$-aryloxy, $(C_6-C_{14})$-arylcarbonyl and $(C_6-C_{14})$-aryloxycarbonyl, each of which may be substituted in the aryl moiety by halogen, $(C_1-C_6)$-alkyl and/or $(C_1-C_6)$-haloalkyl;
$(C_6-C_{14})$-aryl-$(C_1-C_6)$-alkyl, $(C_6-C_{14})$-aryl-$(C_1-C_6)$-alkoxy, $(C_6-C_{14})$-aryl-$(C_1-C_6)$-alkylcarbonyl, $(C_6-C_{14})$-aryl-$(C_1-C_6)$-alkylcarbonyloxy, $(C_6-C_{14})$-aryl-$(C_1-C_6)$-alkoxycarbonyl, $(C_6-C_{14})$-aryl-$(C_1-C_6)$-alkoxycarbonyloxy;
aminocarbonyl-$(C_1-C_6)$-alkyl, di-$(C_1-C_6)$-alkylaminocarbonyl-$(C_1-C_6)$-alkyl;
N—(($(C_1-C_6)$-haloalkanoyl)-aminocarbonyl, mono-(($(C_6-C_{14})$-aryl)-aminocarbonyl, di-(($(C_6-C_{14})$-aryl)-aminocarbonyl;
$(C_1-C_6)$-alkoxy-$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy;
$(C_3-C_8)$-cycloalkyl which is unsubstituted or mono- or polysubstituted in the cycloalkyl radical by $(C_1-C_6)$-alkyl and/or halogen; $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy;
$(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;

hydroxy-$(C_1-C_6)$-alkyl, hydroxy-$(C_1-C_6)$-alkoxy, cyano-$(C_1-C_6)$-alkoxy, cyano-$(C_1-C_6)$-alkyl;

$(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy; $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio and $(C_3-C_6)$-alkynylthio;

$R^3$ is selected from the group consisting of
hydrogen;
$(C_1-C_6)$-alkylcarbonyl, $(C_1-C_6)$-haloalkylcarbonyl;
$(C_2-C_6)$-alkenylcarbonyl, $(C_2-C_6)$-haloalkenylcarbonyl;
$(C_2-C_6)$-alkynylcarbonyl, $(C_2-C_6)$-haloalkynylcarbonyl;
$(C_6-C_{14})$-arylcarbonyl which may in each case be substituted in the aryl moiety by halogen, $(C_1-C_6)$-alkyl and/or $(C_1-C_6)$-haloalkyl;
aminocarbonyl, [$(C_1-C_6)$-alkylamino]carbonyl, [di-$(C_1-C_6)$-alkylamino]carbonyl:
$(C_1-C_6)$-alkoxycarbonyl, $(C_2-C_6)$-alkenyloxycarbonyl, $(C_2-C_6)$-alkynyloxycarbonyl;
$(C_1-C_6)$-trialkylsilyl;
$(C_1-C_6)$-alkylsulfonyl, $(C_1-C_6)$-haloalkylsulfonyl;
$(C_6-C_{14})$-arylsulfonyl which may in each case be substituted in the aryl moiety by halogen, $(C_1-C_6)$-alkyl and/or $(C_1-C_6)$-haloalkyl;
$(C_1-C_6)$-alkyl, $(C_1-C_6)$-haloalkyl, $(C_1-C_6)$-alkylcarbonyl-$(C_1-C_4)$-alkyl;
$(C_2-C_6)$-alkenyl, $(C_2-C_6)$-haloalkenyl;
$(C_2-C_6)$-alkynyl, $(C_2-C_6)$-haloalkynyl; tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;
$(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
$(C_6-C_{14})$-aryl which may be substituted in the aryl moiety in each case by halogen, $(C_1-C_6)$-alkyl and/or $(C_1-C_6)$-haloalkyl;
$(C_2-C_{14})$-Het-aryl which may in each case be substituted in the Het-aryl moiety by halogen, $(C_1-C_6)$-alkyl and/or $(C_1-C_6)$-haloalkyl;
$(C_6-C_{14})$-aryl-$(C_1-C_6)$-alkyl which may in each case be substituted in the aryl moiety by halogen, $(C_1-C_6)$-alkyl and/or $(C_1-C_6)$-haloalkyl;
aminocarbonyl-$(C_1-C_6)$-alkyl;
$(C_1-C_6)$-alkoxy-$(C_1-C_6)$-alkyl;
$(C_3-C_8)$-cycloalkyl which may be mono- or polysubstituted in the cycloalkyl radical by $(C_1-C_6)$-alkyl and/or halogen;
$(C_3-C_8)$-cycloalkyl-$(C_1-C_6)$-alkyl, $(C_3-C_8)$-cycloalkyl-$(C_1-C_6)$-haloalkyl;
$(C_3-C_8)$-cycloalkenyl-$(C_1-C_6)$-alkyl, $(C_3-C_8)$-cycloalkenyl-$(C_1-C_6)$-haloalkyl, hydroxy-$(C_1-C_6)$-alkyl, cyano-$(C_1-C_6)$-alkyl;
$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl;

$R^4$ and $R^5$ are each independently of one another selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or
the radicals $R^4$ and $R^5$ together with the carbon atom to which they are attached form a three- to seven-membered ring;

$R^6$ and $R^7$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or
the radicals $R^6$ and $R^7$ together form a $(C_1-C_7)$-alkylene group which may contain one or more oxygen and/or sulfur atoms, where the $(C_1-C_7)$-alkylene group may be mono- or polysubstituted by halogen and the respective halogen substituents may be identical or different;

n represents the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl, $(C_6-C_{14})$-aryl and nitro, where the $R^9$ and $R^{10}$ radicals may be attached to one another via an —O—CH$_2$—O— group forming a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl, said process comprising reacting a compound of formula (IIa)

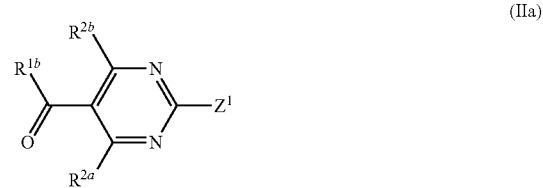

(IIa)

in which $Z^1$ represents an exchangeable radical or a leaving group selected from the group consisting of fluorine, chlorine, bromine, iodine, $(C_1\text{-}C_4)$-alkylsulfanyl, $(C_1\text{-}C_4)$-alkylsulfinyl, $(C_1\text{-}C_4)$-alkylsulfonyl, unsubstituted or substituted phenyl-$(C_1\text{-}C_4)$-alkylsulfonyl, and $(C_1\text{-}C_4)$-alkylphenylsulfonyl, with an amine of formula (III) and/or an acid addition salt of an amine of formula (III)

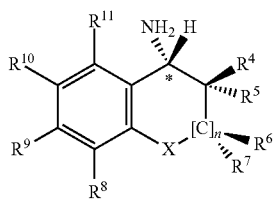

(III)

and final reduction of a keto group or final reaction of a keto group with one or more carbon nucleophiles to give a compound of formula (I) where $R^3$ represents hydrogen.

21. A process for preparing a compound of formula (I) and/or an agrochemically acceptable salt thereof and/or an agrochemically acceptable quaternized nitrogen derivative thereof

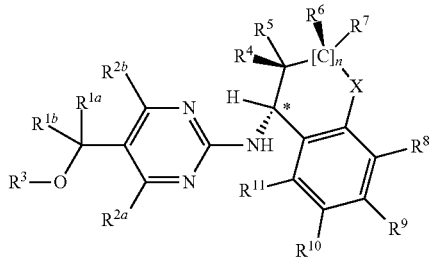

(I)

wherein $R^{1a}$ is selected from the group consisting of
hydrogen, cyano, C(O)OH, C(O)NH$_2$;
$(C_1\text{-}C_6)$-alkyl, $(C_1\text{-}C_6)$-haloalkyl, $(C_1\text{-}C_6)$-alkylcarbonyl-$(C_1\text{-}C_4)$-alkyl;
$(C_1\text{-}C_6)$-alkoxycarbonyl-$(C_1\text{-}C_6)$-alkyl, $(C_1\text{-}C_6)$-haloalkoxycarbonyl-$(C_1\text{-}C_6)$-alkyl, $(C_1\text{-}C_6)$-alkoxycarbonyl-$(C_1\text{-}C_6)$-haloalkyl, $(C_1\text{-}C_6)$-haloalkoxycarbonyl-$(C_1\text{-}C_6)$-haloalkyl;
$(C_2\text{-}C_6)$-alkenyl, $(C_2\text{-}C_6)$-haloalkenyl;
$(C_2\text{-}C_6)$-alkynyl, $(C_2\text{-}C_6)$-haloalkynyl;
$(C_6\text{-}C_{14})$-aryl which may be substituted in the aryl moiety in each case by halogen, $(C_1\text{-}C_6)$-alkyl and/or $(C_1\text{-}C_6)$-haloalkyl;
pyridyl which may in each case be substituted by halogen, $(C_1\text{-}C_6)$-alkyl and/or $(C_1\text{-}C_6)$-haloalkyl;
thienyl which may in each case be substituted by halogen, $(C_1\text{-}C_6)$-alkyl and/or $(C_1\text{-}C_6)$-haloalkyl;
$(C_6\text{-}C_{14})$-aryl-$(C_1\text{-}C_6)$-alkyl which may in each case be substituted in the aryl moiety by halogen, $(C_1\text{-}C_6)$-alkyl and/or $(C_1\text{-}C_6)$-haloalkyl;
aminocarbonyl-$(C_1\text{-}C_6)$-alkyl;
$(C_1\text{-}C_6)$-alkoxy-$(C_1\text{-}C_6)$-alkyl;
$(C_3\text{-}C_8)$-cycloalkyl which may be unsubstituted or mono- or polysubstituted in the cycloalkyl radical by $(C_1\text{-}C_6)$-alkyl and/or halogen; $(C_3\text{-}C_8)$-cycloalkyl-$(C_1\text{-}C_6)$-alkyl, $(C_3\text{-}C_8)$-cycloalkyl-$(C_1\text{-}C_6)$-haloalkyl;
$(C_3\text{-}C_8)$-cycloalkenyl, $(C_3\text{-}C_8)$-cycloalkenyl-$(C_1\text{-}C_6)$-alkyl, $(C_3\text{-}C_8)$-cycloalkenyl-$(C_1\text{-}C_6)$-haloalkyl;
hydroxy-$(C_1\text{-}C_6)$-alkyl, amino-$(C_1\text{-}C_6)$-alkyl, cyano-$(C_1\text{-}C_6)$-alkyl;
$(C_1\text{-}C_6)$-alkylsulfonyl-$(C_1\text{-}C_6)$-alkyl, $(C_1\text{-}C_6)$-alkylthio-$(C_1\text{-}C_6)$-alkyl, $(C_1\text{-}C_6)$-alkylsulfinyl-$(C_1\text{-}C_6)$-alkyl, $(C_1\text{-}C_6)$-haloalkylsulfonyl-$(C_1\text{-}C_6)$-alkyl, $(C_1\text{-}C_6)$-haloalkylthio-$(C_1\text{-}C_6)$-alkyl, $(C_1\text{-}C_6)$-haloalkylsulfinyl-$(C_1\text{-}C_6)$-alkyl, $(C_1\text{-}C_6)$-alkylsulfonyl-$(C_1\text{-}C_6)$-haloalkyl, $(C_1\text{-}C_6)$-alkylthio-$(C_1\text{-}C_6)$-haloalkyl, $(C_1\text{-}C_6)$-alkylsulfinyl-$(C_1\text{-}C_6)$-haloalkyl, $(C_1\text{-}C_6)$-haloalkylsulfonyl-$(C_1\text{-}C_6)$-haloalkyl, $(C_1\text{-}C_6)$-haloalkylthio-$(C_1\text{-}C_6)$-haloalkyl, and $(C_1\text{-}C_6)$-haloalkylsulfinyl-$(C_1\text{-}C_6)$-haloalkyl;

$R^{1b}$ is selected from the group consisting of
cyano, C(O)OH, C(O)NH$_2$;
$(C_1\text{-}C_6)$-alkyl, $(C_1\text{-}C_6)$-haloalkyl, $(C_1\text{-}C_6)$-alkylcarbonyl-$(C_1\text{-}C_4)$-alkyl;
$(C_1\text{-}C_6)$-alkoxycarbonyl-$(C_1\text{-}C_6)$-alkyl, $(C_1\text{-}C_6)$-haloalkoxycarbonyl-$(C_1\text{-}C_6)$-alkyl, $(C_1\text{-}C_6)$-alkoxycarbonyl-$(C_1\text{-}C_6)$-haloalkyl, $(C_1\text{-}C_6)$-haloalkoxycarbonyl-$(C_1\text{-}C_6)$-haloalkyl;
$(C_2\text{-}C_6)$-alkenyl, $(C_2\text{-}C_6)$-haloalkenyl;
$(C_2\text{-}C_6)$-alkynyl, $(C_2\text{-}C_6)$-haloalkynyl;
$(C_6\text{-}C_{14})$-aryl which may be substituted in the aryl moiety in each case by halogen, $(C_1\text{-}C_6)$-alkyl and/or $(C_1\text{-}C_6)$-haloalkyl;
pyridyl which may in each case be substituted by halogen, $(C_1\text{-}C_6)$-alkyl and/or $(C_1\text{-}C_6)$-haloalkyl;
thienyl which may in each case be substituted by halogen, $(C_1\text{-}C_6)$-alkyl and/or $(C_1\text{-}C_6)$-haloalkyl;
$(C_6\text{-}C_{14})$-aryl-$(C_1\text{-}C_6)$-alkyl which may in each case be substituted in the aryl moiety by halogen, $(C_1\text{-}C_6)$-alkyl and/or $(C_1\text{-}C_6)$-haloalkyl;
aminocarbonyl-$(C_1\text{-}C_6)$-alkyl;
$(C_1\text{-}C_6)$-alkoxy-$(C_1\text{-}C_6)$-alkyl;
$(C_3\text{-}C_8)$-cycloalkyl which may be unsubstituted or mono- or polysubstituted in the cycloalkyl radical by $(C_1\text{-}C_6)$-alkyl and/or halogen; $(C_3\text{-}C_8)$-cycloalkyl-$(C_1\text{-}C_6)$-alkyl, $(C_3\text{-}C_8)$-cycloalkyl-$(C_1\text{-}C_6)$-haloalkyl;
$(C_3\text{-}C_8)$-cycloalkenyl, $(C_3\text{-}C_8)$-cycloalkenyl-$(C_1\text{-}C_6)$-alkyl, $(C_3\text{-}C_8)$-cycloalkenyl-$(C_1\text{-}C_6)$-haloalkyl;
hydroxy-$(C_1\text{-}C_6)$-alkyl, amino-$(C_1\text{-}C_6)$-alkyl, cyano-$(C_1\text{-}C_6)$-alkyl;
$(C_1\text{-}C_6)$-alkylsulfonyl-$(C_1\text{-}C_6)$-alkyl, $(C_1\text{-}C_6)$-alkylthio-$(C_1\text{-}C_6)$-alkyl, $(C_1\text{-}C_6)$-alkylsulfinyl-$(C_1\text{-}C_6)$-alkyl, $(C_1\text{-}C_6)$-haloalkylsulfonyl-$(C_1\text{-}C_6)$-alkyl, $(C_1\text{-}C_6)$-haloalkylthio-$(C_1\text{-}C_6)$-alkyl, $(C_1\text{-}C_6)$-haloalkylsulfinyl-$(C_1\text{-}C_6)$-alkyl, $(C_1\text{-}C_6)$-alkylsulfonyl-$(C_1\text{-}C_6)$-haloalkyl, $(C_1\text{-}C_6)$-alkylthio-$(C_1\text{-}C_6)$-haloalkyl, $(C_1\text{-}C_6)$-alkylsulfinyl-$(C_1\text{-}C_6)$-haloalkyl, $(C_1\text{-}C_6)$-haloalkylsulfonyl-$(C_1\text{-}C_6)$-haloalkyl, $(C_1\text{-}C_6)$-haloalkylthio-$(C_1\text{-}C_6)$-haloalkyl, and $(C_1\text{-}C_6)$-haloalkylsulfinyl-$(C_1\text{-}C_6)$-haloalkyl;

$R^{2a}$ and $R^{2b}$ are in each case independently of one another selected from the group consisting of
hydrogen, halogen, hydroxyl, cyano, C(O)OH, C(O)NH$_2$;
$(C_1\text{-}C_6)$-alkyl, $(C_1\text{-}C_6)$-haloalkyl, $(C_1\text{-}C_6)$-alkylcarbonyl, $(C_1\text{-}C_6)$-haloalkylcarbonyl, $(C_1\text{-}C_6)$-alkylcarbonyloxy, $(C_1\text{-}C_6)$-haloalkylcarbonyloxy, $(C_1\text{-}C_6)$-alkylcarbonyl-$(C_1\text{-}C_4)$-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

aminocarbonyl-($C_1$-$C_6$)-alkyl, di-($C_1$-$C_6$)-alkylaminocarbonyl-($C_1$-$C_6$)-alkyl;

N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which is unsubstituted or mono- or polysubstituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;

($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;

hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;

($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio and ($C_3$-$C_6$)-alkynylthio;

$R^3$ is selected from the group consisting of hydrogen;

($C_1$-$C_6$)-alkylcarbonyl, ($C_1$-$C_6$)-haloalkylcarbonyl;

($C_2$-$C_6$)-alkenylcarbonyl, ($C_2$-$C_6$)-haloalkenylcarbonyl;

($C_2$-$C_6$)-alkynylcarbonyl, ($C_2$-$C_6$)-haloalkynylcarbonyl;

($C_6$-$C_{14}$)-arylcarbonyl which may in each case be substituted in the aryl moiety by halogen, ($C_1$-$C_6$)-alkyl and/or ($C_1$-$C_6$)-haloalkyl;

aminocarbonyl, [($C_1$-$C_6$)-alkylamino]carbonyl, [di-($C_1$-$C_6$)-alkylamino]carbonyl:

($C_1$-$C_6$)-alkoxycarbonyl, ($C_2$-$C_6$)-alkenyloxycarbonyl, ($C_2$-$C_6$)-alkynyloxycarbonyl;

($C_1$-$C_6$)-trialkylsilyl;

($C_1$-$C_6$)-alkylsulfonyl, ($C_1$-$C_6$)-haloalkylsulfonyl;

($C_6$-$C_{14}$)-arylsulfonyl which may in each case be substituted in the aryl moiety by halogen, ($C_1$-$C_6$)-alkyl and/or ($C_1$-$C_6$)-haloalkyl;

($C_1$-$C_6$)-alkyl, ($C_1$-$C_6$)-haloalkyl, ($C_1$-$C_6$)-alkylcarbonyl-($C_1$-$C_4$)-alkyl;

($C_2$-$C_6$)-alkenyl, ($C_2$-$C_6$)-haloalkenyl;

($C_2$-$C_6$)-alkynyl, ($C_2$-$C_6$)-haloalkynyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_6$-$C_{14}$)-aryl which may be substituted in the aryl moiety in each case by halogen, ($C_1$-$C_6$)-alkyl and/or ($C_1$-$C_6$)-haloalkyl;

($C_2$-$C_{14}$)-Het-aryl which may in each case be substituted in the Het-aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

$(C_1-C_6)$-alkoxy-$(C_1-C_6)$-alkyl;

$(C_3-C_8)$-cycloalkyl which may be mono- or polysubstituted in the cycloalkyl radical by $(C_1-C_6)$-alkyl and/or halogen;

$(C_3-C_8)$-cycloalkyl-$(C_1-C_6)$-alkyl, $(C_3-C_8)$-cycloalkyl-$(C_1-C_6)$-haloalkyl;

$(C_3-C_8)$-cycloalkenyl-$(C_1-C_6)$-alkyl, $(C_3-C_8)$-cycloalkenyl-$(C_1-C_6)$-haloalkyl, hydroxy-$(C_1-C_6)$-alkyl, cyano-$(C_1-C_6)$-alkyl;

$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl;

$R^4$ and $R^5$ are each independently of one another selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or the radicals $R^4$ and $R^5$ together with the carbon atom to which they are attached form a three- to seven-membered ring;

$R^6$ and $R^7$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the radicals $R^6$ and $R^7$ together form a $(C_1-C_7)$-alkylene group which may contain one or more oxygen and/or sulfur atoms, where the $(C_1-C_7)$-alkylene group may be mono- or polysubstituted by halogen and the respective halogen substituents may be identical or different;

n represents the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl, $(C_6-C_{14})$-aryl and nitro, where the $R^9$ and $R^{10}$ radicals may be attached to one another via an —O—CH$_2$—O— group forming a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl, said process comprising reacting a compound of formula (11b)

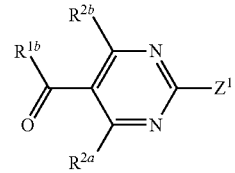

(IIb)

wherein $Z^1$ represents an exchangeable radical or a leaving group, with an amine of formula (III) and/or an acid addition salt of an amine of formula (III)

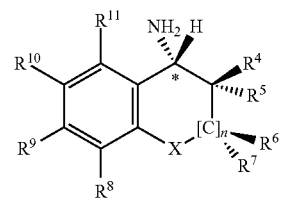

(III)

to give a 2-amino-5-ketopyrimidine derivative of formula (Ib)

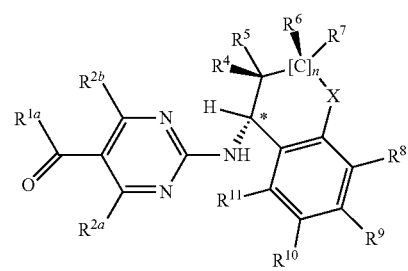

(Ib)

and final reaction of a keto group with one or more carbon nucleophiles to give a compound of formula (I) where $R^3$ represents hydrogen.

22. A process for preparing a compound of formula (I), and/or an agrochemically acceptable salt thereof and/or an agrochemically acceptable quaternized nitrogen derivative thereof

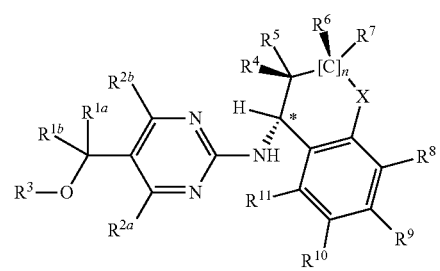

(I)

wherein $R^{1a}$ is selected from the group consisting of hydrogen, cyano, C(O)OH, C(O)NH$_2$;

($C_1$-$C_6$)-alkyl, ($C_1$-$C_6$)-haloalkyl, ($C_1$-$C_6$)-alkylcarbonyl-($C_1$-$C_4$)-alkyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl;

($C_2$-$C_6$)-alkynyl, ($C_2$-$C_6$)-haloalkynyl;

($C_6$-$C_{14}$)-aryl which may be substituted in the aryl moiety in each case by halogen, ($C_1$-$C_6$)-alkyl and/or ($C_1$-$C_6$)-haloalkyl;

pyridyl which may in each case be substituted by halogen, ($C_1$-$C_6$)-alkyl and/or ($C_1$-$C_6$)-haloalkyl;

thienyl which may in each case be substituted by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;

hydroxy-($C_1$-$C_6$)-alkyl, amino-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^{1b}$ is selected from the group consisting of cyano, C(O)OH, C(O)NH$_2$;

($C_1$-$C_6$)-alkyl, ($C_1$-$C_6$)-haloalkyl, ($C_1$-$C_6$)-alkylcarbonyl-($C_1$-$C_4$)-alkyl;

($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl;

($C_2$-$C_6$)-alkynyl, ($C_2$-$C_6$)-haloalkynyl;

($C_6$-$C_{14}$)-aryl which may be substituted in the aryl moiety in each case by halogen, ($C_1$-$C_6$)-alkyl and/or ($C_1$-$C_6$)-haloalkyl;

pyridyl which may in each case be substituted by halogen, ($C_1$-$C_6$)-alkyl and/or ($C_1$-$C_6$)-haloalkyl;

thienyl which may in each case be substituted by halogen, ($C_1$-$C_6$)-alkyl and/or ($C_1$-$C_6$)-haloalkyl;

($C_6$-$C_{14}$)-aryl-($C_1$-$C_6$)-alkyl which may in each case be substituted in the aryl moiety by halogen, ($C_1$-$C_6$)-alkyl and/or ($C_1$-$C_6$)-haloalkyl;

aminocarbonyl-($C_1$-$C_6$)-alkyl;

($C_1$-$C_6$)-alkoxy-($C_1$-$C_6$)-alkyl;

($C_3$-$C_8$)-cycloalkyl which may be unsubstituted or mono- or polysubstituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl;

($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl;

hydroxy-($C_1$-$C_6$)-alkyl, amino-($C_1$-$C_6$)-alkyl, cyano-($C_1$-$C_6$)-alkyl;

($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, and ($C_1$-$C_6$)-haloalkylsulfinyl-($C_1$-$C_6$)-haloalkyl;

$R^{2a}$ and $R^{2b}$ are in each case independently of one another selected from the group consisting of hydrogen, halogen, hydroxyl, cyano, C(O)OH, C(O)NH$_2$;

($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;

($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;

($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;

($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;

($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;

aminocarbonyl-($C_1$-$C_6$)-alkyl, di-($C_1$-$C_6$)-alkylaminocarbonyl-($C_1$-$C_6$)-alkyl;

N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;

($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;

($C_3$-$C_8$)-cycloalkyl which is unsubstituted or mono- or polysubstituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy;

$(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;

hydroxy-$(C_1-C_6)$-alkyl, hydroxy-$(C_1-C_6)$-alkoxy, cyano-$(C_1-C_6)$-alkoxy, cyano-$(C_1-C_6)$-alkyl;

$(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy; $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio and $(C_3-C_6)$-alkynylthio;

$R^3$ is selected from the group consisting of hydrogen;

$(C_1-C_6)$-alkylcarbonyl, $(C_1-C_6)$-haloalkylcarbonyl;

$(C_2-C_6)$-alkenylcarbonyl, $(C_2-C_6)$-haloalkenylcarbonyl;

$(C_2-C_6)$-alkynylcarbonyl, $(C_2-C_6)$-haloalkynylcarbonyl;

$(C_6-C_{14})$-arylcarbonyl which may in each case be substituted in the aryl moiety by halogen, $(C_1-C_6)$-alkyl and/or $(C_1-C_6)$-haloalkyl;

aminocarbonyl, [$(C_1-C_6)$-alkylamino]carbonyl, [di-$(C_1-C_6)$-alkylamino]carbonyl:

$(C_1-C_6)$-alkoxycarbonyl, $(C_2-C_6)$-alkenyloxycarbonyl, $(C_2-C_6)$-alkynyloxycarbonyl;

$(C_1-C_6)$-trialkylsilyl;

$(C_1-C_6)$-alkylsulfonyl, $(C_1-C_6)$-haloalkylsulfonyl;

$(C_6-C_{14})$-arylsulfonyl which may in each case be substituted in the aryl moiety by halogen, $(C_1-C_6)$-alkyl and/or $(C_1-C_6)$-haloalkyl;

$(C_1-C_6)$-alkyl, $(C_1-C_6)$-haloalkyl, $(C_1-C_6)$-alkylcarbonyl-$(C_1-C_4)$-alkyl;

$(C_2-C_6)$-alkenyl, $(C_2-C_6)$-haloalkenyl;

$(C_2-C_6)$-alkynyl, $(C_2-C_6)$-haloalkynyl; tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;

$(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;

$(C_6-C_{14})$-aryl which may be substituted in the aryl moiety in each case by halogen, $(C_1-C_6)$-alkyl and/or $(C_1-C_6)$-haloalkyl;

$(C_2-C_{14})$-Het-aryl which may in each case be substituted in the Het-aryl moiety by halogen, $(C_1-C_6)$-alkyl and/or $(C_1-C_6)$-haloalkyl;

$(C_6-C_{14})$-aryl-$(C_1-C_6)$-alkyl which may in each case be substituted in the aryl moiety by halogen, $(C_1-C_6)$-alkyl and/or $(C_1-C_6)$-haloalkyl;

aminocarbonyl-$(C_1-C_6)$-alkyl;

$(C_1-C_6)$-alkoxy-$(C_1-C_6)$-alkyl;

$(C_3-C_8)$-cycloalkyl which may be mono- or polysubstituted in the cycloalkyl radical by $(C_1-C_6)$-alkyl and/or halogen;

$(C_3-C_8)$-cycloalkyl-$(C_1-C_6)$-alkyl, $(C_3-C_8)$-cycloalkyl-$(C_1-C_6)$-haloalkyl;

$(C_3-C_8)$-cycloalkenyl-$(C_1-C_6)$-alkyl, $(C_3-C_8)$-cycloalkenyl-$(C_1-C_6)$-haloalkyl, hydroxy-$(C_1-C_6)$-alkyl, cyano-$(C_1-C_6)$-alkyl;

$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl;

$R^4$ and $R^5$ are each independently of one another selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or the radicals $R^4$ and $R^5$ together with the carbon atom to which they are attached form a three- to seven-membered ring;

$R^6$ and $R^7$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the radicals $R^6$ and $R^7$ together form a $(C_1-C_7)$-alkylene group which may contain one or more oxygen and/or sulfur atoms, where the $(C_1-C_7)$-alkylene group may be mono- or polysubstituted by halogen and the respective halogen substituents may be identical or different;

n represents the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$- dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl, $(C_6-C_{14})$-aryl and nitro, where the $R^9$ and $R^{10}$ radicals may be attached to one another via an —O—CH$_2$—O— group forming a ring;

X represents a bond, CH$_2$, O, S, carbonyl, NH, $CR^{12}R^{13}$, $NR^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl, said process comprising reacting a compound of formula (IIc)

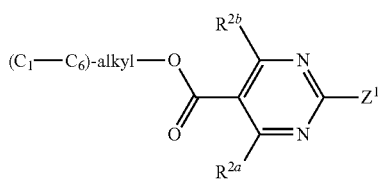

(IIc)

wherein $Z^1$ represents an exchangeable radical or a leaving group, with an amine of formula (III) and/or an acid addition salt of an amine of formula (III)

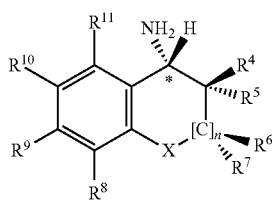

(III)

to give an intermediate of formula (Ic)

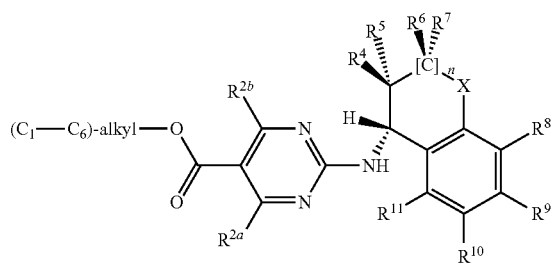

(Ic)

and reacting an ester group with one or more carbon nucleophiles to give a compound of formula (I) in which $R^{1a}=R^{1b}$ and $R^3$ represents hydrogen.

23. A process for preparing a compound according to claim 1, wherein a compound of formula (I) in which $R^3$ represents hydrogen, $R^3$ is converted by a reaction of an alkylation or acylation type into a compound of formula (I) where $R^3$ does not represent hydrogen.

24. A herbicidal composition or plant growth-regulating composition, comprising one or more compounds according to claim 1.

25. A method of controlling one or more harmful plants or for regulating the growth of one or more plants, comprising applying an effective amount of one or more compounds of according to claim 1 to the one or more plants, plant parts, plant seeds and/or an area under cultivation.

26. A product comprising one or more compounds according to claim 1 as a herbicide and/or as a plant growth regulator.

27. The method as claimed in claim 25, wherein the one or more plants comprise one or more crops of useful plants or ornamental plants.

28. The method as claimed in claim 27 wherein the one or more crops are transgenic crop plants.

29. The compound according to claim 1, wherein, if $R^{1a}$ does not represent hydrogen, $R^{1a}$ is attached to $R^{1b}$ via a bond so that, together with the carbon to which these two radicals are attached, a saturated or unsaturated 3- to 7-membered carbo- or heterocycle is formed which is unsubstituted or is substituted with one or more substituents selected from the group consisting of $(C_1-C_6)$-alkyl, $(C_1-C_6)$-haloalkyl, $(C_3-C_8)$-cycloalkyl, and spiro-$(C_3-C_6)$-cycloalkyl.

* * * * *